(12) United States Patent
Sacherman et al.

(10) Patent No.: US 11,419,759 B2
(45) Date of Patent: Aug. 23, 2022

(54) FLUID EXCHANGE APPARATUS FOR EXPANDABLE PORT DELIVERY SYSTEM AND METHODS OF USE

(71) Applicant: ForSight Vision4, Inc., South San Francisco, CA (US)

(72) Inventors: Kevin W. Sacherman, Palo Alto, CA (US); Randolph E. Campbell, Redwood City, CA (US); Darren Doud, Los Altos, CA (US); Kathleen Cogan Farinas, Los Altos, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 271 days.

(21) Appl. No.: 16/877,308

(22) Filed: May 18, 2020

(65) Prior Publication Data

US 2020/0337897 A1    Oct. 29, 2020

Related U.S. Application Data

(63) Continuation of application No. PCT/US2018/061262, filed on Nov. 15, 2018.

(60) Provisional application No. 62/589,377, filed on Nov. 21, 2017.

(51) Int. Cl.
*A61F 9/00* (2006.01)
*A61M 31/00* (2006.01)

(52) U.S. Cl.
CPC ......... *A61F 9/0017* (2013.01); *A61M 31/002* (2013.01); *A61M 2202/02* (2013.01); *A61M 2210/0612* (2013.01)

(58) Field of Classification Search
None
See application file for complete search history.

(56) References Cited

U.S. PATENT DOCUMENTS

| | | |
|---|---|---|
| 1,747,814 A | 2/1930 | Bradley |
| 2,564,977 A | 8/1951 | Hu |
| 2,585,815 A | 2/1952 | McLintock |
| 2,646,042 A | 7/1953 | Hu |
| 2,886,497 A | 5/1959 | Butler |
| 3,232,117 A | 2/1966 | Gilmont |
| 3,416,530 A | 12/1968 | Ness |
| 3,612,089 A | 10/1971 | Beguiristain |
| 3,618,604 A | 11/1971 | Ness |
| 3,641,237 A | 2/1972 | Gould et al. |
| 3,734,095 A | 5/1973 | Santomieri |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |

(Continued)

FOREIGN PATENT DOCUMENTS

| | | |
|---|---|---|
| CN | 204600878 U | 9/2015 |
| CN | 105979985 A | 9/2016 |

(Continued)

OTHER PUBLICATIONS

U.S. Appl. No. 15/777,593, filed May 18, 2018, 2021/0205130.
U.S. Appl. No. 16/091,493, filed Oct. 4, 2018, 2019/0117454.
U.S. Appl. No. 16/380,786, filed Apr. 10, 2019, 2019/0350754.
U.S. Appl. No. 16/386,854, filed Apr. 17, 2019, 2019/0336335.
U.S. Appl. No. 16/514,128, filed Jul. 17, 2019, 2020/0107955.
U.S. Appl. No. 16/540,617, filed Aug. 14, 2019, 2020/0030142.
U.S. Appl. No. 16/808,784, filed Mar. 04, 2020, 2020/0405537.
U.S. Appl. No. 16/842,059, filed Apr. 7, 2020, 2021/0025885.
U.S. Appl. No. 17/016,953, filed Sep. 10, 2020, 2021/0196510.

(Continued)

*Primary Examiner* — Hasan S Ahmed
*Assistant Examiner* — Randeep Singh
(74) *Attorney, Agent, or Firm* — Mintz Levin Cohn Ferris Glovsky and Popeo, P.C.

(57) ABSTRACT

A device for injecting a therapeutic agent into an ocular implant at least partially implanted in an eye including an injection lumen providing a pathway for injecting the therapeutic agent into the implant; an outlet lumen providing a pathway for pre-existing fluid in the ocular implant to exit the implant; and a collection chamber fluidly coupled to the outlet lumen that provides a first fluid outflow resistance and a second fluid outflow resistance. The first fluid outflow resistance is lower than a first resistance to outflow of the implant. The second fluid outflow resistance is greater than a force imparted onto the implant by intraocular pressure of the eye. Injection of therapeutic agent into the implant via the injection lumen causes the pre-existing fluid to exit the implant and enter the collection chamber via the outlet lumen and causes a second pre-existing fluid to displace from the collection chamber.

17 Claims, 32 Drawing Sheets

(56) References Cited

U.S. PATENT DOCUMENTS

| | | |
|---|---|---|
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,273,530 A | 12/1993 | del Cerro et al. |
| 5,277,912 A | 1/1994 | Lowe et al. |
| 5,282,829 A | 2/1994 | Hermes |
| 5,300,114 A | 4/1994 | Gwon et al. |
| 5,322,504 A | 6/1994 | Doherty et al. |
| 5,322,691 A | 6/1994 | Darougar et al. |
| 5,324,518 A | 6/1994 | Orth et al. |
| 5,334,189 A | 8/1994 | Wade |
| 5,336,175 A | 8/1994 | Mames |
| 5,358,473 A | 10/1994 | Mitchell |
| 5,364,343 A | 11/1994 | Apolet et al. |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,448 A | 12/1995 | Urich |
| 5,476,511 A | 12/1995 | Gwon et al. |
| 5,554,132 A | 9/1996 | Straits et al. |
| 5,562,915 A | 10/1996 | Lowe et al. |
| 5,578,042 A | 11/1996 | Cumming |
| 5,674,193 A | 10/1997 | Hayes |
| 5,681,572 A | 10/1997 | Seare, Jr. |
| 5,725,493 A | 3/1998 | Avery et al. |
| 5,755,684 A | 5/1998 | Chen |
| 5,766,242 A | 6/1998 | Wong et al. |
| 5,770,076 A | 6/1998 | Chu et al. |
| 5,773,019 A | 6/1998 | Ashton et al. |
| 5,792,099 A | 8/1998 | DeCamp et al. |
| 5,797,898 A | 8/1998 | Santini, Jr. et al. |
| 5,807,581 A | 9/1998 | Rosenblatt et al. |
| 5,817,075 A | 10/1998 | Giungo |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,468,264 B1 | 10/2002 | Gillis et al. |
| 6,472,162 B1 | 10/2002 | Coelho et al. |
| 6,605,066 B1 | 8/2003 | Gravagna et al. |
| 6,620,139 B1 | 9/2003 | Plicchi et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,695,821 B1 | 2/2004 | Sjaarda |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,869,412 B2 | 3/2005 | Ross |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,699,820 B1 | 4/2010 | French |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,277,830 B2 | 10/2012 | de Juan, Jr. et al. |
| 8,399,006 B2 | 3/2013 | de Juan, Jr. et al. |
| 8,623,395 B2 | 1/2014 | de Juan, Jr. et al. |
| 8,905,963 B2 | 12/2014 | de Juan, Jr. et al. |
| 9,033,911 B2 | 5/2015 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |

(56) References Cited

U.S. PATENT DOCUMENTS

| | | |
|---|---|---|
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0188244 A1 | 12/2002 | Smith |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0047011 A1 | 3/2003 | Diermann et al. |
| 2003/0118649 A1 | 6/2003 | Gao et al. |
| 2003/0119177 A1 | 6/2003 | Gruber et al. |
| 2003/0120217 A1 | 6/2003 | Abergel |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0233067 A1 | 12/2003 | McIntosh et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0171491 A1 | 8/2005 | Minh Miner et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0256462 A1 | 11/2005 | Underwood |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0083155 A1 | 4/2007 | Muller |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford, et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0108954 A1 | 5/2008 | Mathias et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2008/0293691 A1 | 11/2008 | Brigand et al. |
| 2009/0005864 A1 | 1/2009 | Eggleston |
| 2009/0012485 A1 | 1/2009 | Michaels et al. |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0061071 A1 | 3/2009 | McMorrow et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |

(56) References Cited

U.S. PATENT DOCUMENTS

| | | |
|---|---|---|
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124986 A1 | 5/2009 | Hayakawa |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2009/0326489 A1 | 12/2009 | Kensy et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0191176 A1 | 7/2010 | Ho et al. |
| 2010/0197512 A1 | 8/2010 | Trinkle et al. |
| 2010/0211041 A1 | 8/2010 | Omori et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0227904 A1 | 9/2010 | Kabra et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2012/0029445 A1 | 2/2012 | de Juan, Jr. et al. |
| 2012/0029470 A1 | 2/2012 | Juan, Jr. et al. |
| 2012/0095439 A1 | 4/2012 | de Juan, Jr. et al. |
| 2012/0184905 A1 | 7/2012 | Shekalim |
| 2012/0296423 A1 | 11/2012 | Caffey et al. |
| 2013/0165860 A1 | 6/2013 | Doud et al. |
| 2013/0204209 A1 | 8/2013 | de Juan, Jr. et al. |
| 2013/0218081 A1 | 8/2013 | Roth |
| 2013/0245544 A1 | 9/2013 | de Juan, Jr. et al. |
| 2013/0245573 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0304031 A1 | 11/2013 | Varner et al. |
| 2013/0324918 A1 | 12/2013 | de Juan, Jr. et al. |
| 2013/0324942 A1 | 12/2013 | de Juan, Jr. et al. |
| 2013/0338564 A1 | 12/2013 | Rickard et al. |
| 2014/0031769 A1 | 1/2014 | de Juan, Jr. et al. |
| 2014/0033800 A1 | 2/2014 | Farinas et al. |
| 2014/0073714 A1 | 3/2014 | Reich et al. |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0296800 A1 | 10/2014 | Erickson et al. |
| 2014/0358125 A1 | 12/2014 | de Juan, Jr. et al. |
| 2015/0080846 A1 | 3/2015 | de Juan, Jr. et al. |
| 2015/0250647 A1 | 9/2015 | de Juan, Jr. et al. |
| 2015/0297402 A1 | 10/2015 | de Juan, Jr. et al. |
| 2016/0038488 A1 | 2/2016 | Horvath et al. |
| 2016/0101046 A1 | 4/2016 | Reich et al. |
| 2016/0128867 A1 | 5/2016 | Bachelder et al. |
| 2016/0184134 A1 | 6/2016 | Varner et al. |
| 2016/0258855 A1 | 9/2016 | Farinas et al. |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0147204 A1 | 5/2018 | Horvath et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0117454 A1 | 4/2019 | Campbell et al. |
| 2019/0336335 A1 | 11/2019 | de Juan, Jr. et al. |
| 2019/0350754 A1 | 11/2019 | Bianchi et al. |
| 2019/0365757 A1 | 12/2019 | Horvath et al. |
| 2020/0030142 A1 | 1/2020 | Erickson et al. |
| 2020/0060874 A1 | 2/2020 | Bachelder et al. |
| 2020/0107955 A1 | 4/2020 | Erickson et al. |

FOREIGN PATENT DOCUMENTS

| | | |
|---|---|---|
| CN | 106413642 A | 2/2017 |
| EP | 0033042 B1 | 8/1984 |
| EP | 0 228 185 A1 | 11/1986 |
| EP | 0498471 | 8/1992 |
| EP | 0500143 | 8/1992 |
| EP | 0295248 | 3/1993 |
| EP | 0671165 | 9/1995 |

(56) References Cited

FOREIGN PATENT DOCUMENTS

| | | |
|---|---|---|
| EP | 0944658 B1 | 6/2003 |
| EP | 1671624 | 6/2006 |
| EP | 1385452 | 9/2006 |
| EP | 1409065 | 1/2007 |
| EP | 1337284 B1 | 12/2007 |
| EP | 1911481 | 4/2008 |
| EP | 1521572 B1 | 3/2009 |
| JP | 01-149716 | 6/1989 |
| JP | 01-197429 A | 8/1989 |
| JP | 2001-518880 A | 10/2001 |
| JP | 2004-516889 A | 6/2004 |
| WO | WO-88/04573 A1 | 6/1988 |
| WO | WO-90/07545 A2 | 7/1990 |
| WO | WO-94/24969 A1 | 11/1994 |
| WO | WO-95/28984 A1 | 11/1995 |
| WO | WO-97/29850 | 8/1997 |
| WO | WO-98/25982 | 6/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-01/68016 A2 | 9/2001 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/025413 A2 | 3/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006/138609 | 12/2006 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 | 5/2008 |
| WO | WO-2008/076544 | 6/2008 |
| WO | WO-2008/094989 A2 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2009/137780 A2 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010/088548 A1 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/079232 | 6/2011 |
| WO | WO-2012/019047 A2 | 2/2012 |
| WO | WO-2012/019136 A2 | 2/2012 |
| WO | WO-2012/065006 A2 | 5/2012 |
| WO | WO-2013/003620 | 1/2013 |
| WO | WO-2013/022801 | 2/2013 |
| WO | WO-2013/040247 A2 | 3/2013 |
| WO | WO-2013/151904 A1 | 10/2013 |
| WO | WO-2017/087902 A1 | 5/2017 |

OTHER PUBLICATIONS

U.S. Appl. No. 15/102,191, filed Jun. 6, 2016, 2016/0302965.
U.S. Appl. No. 15/606,647, filed May 26, 2017, 2017/0258634.
U.S. Appl. No. 16/434,966, filed Jun. 7, 2019, 2019/0365757.
U.S. Appl. No. 16/671,749, filed Nov. 1, 2019, 2020/0060874.
"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.
"MAbPac SCX-10 Column for Monoclonal Antibody Variant Analysis." *Dionex*.Aug. 2010. [http://www.dionex.com/en-us/webdocs/87008-DS-MAbPac-SCX-10-Column20Aug2010-LPN2567-03.pdf], Web. Retrieved May 2012. 4 Pages.
Andrews, "Effect of nonsteroidal anti-inflammatory drugs on LFA-1 and ICAM-1 expression in gastric mucosa," Am J Physiol. Apr. 1994;266(4 Pt 1):G657-664.
Arvo, Agenda for the Summer Eye Research Conference, (Jul. 2009). 7 pages.
Avery et al., "Intravitreal bevacizumab (Avastin) in the treatment of proliferative diabetic retinopathy," Ophthalmology. Oct. 2006, 113(10):1695-1705.e6.

(56) References Cited

OTHER PUBLICATIONS

Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Breslin, C.W., et al., "Chapter 7. Slow Release Artificial Tears", *Symposium on Ocular Therapy* pp. 77-83, 1977.
Carbonaro, et al. "Nano-pore silicon membrane characterization by diffusion and electrical resistance." *Journal of Membrane Science.* 241 (2004):249-255.
Castro et al., "Effect of COX inhibitors on VEGF-induced retinal vascular leakage and experimental corneal and choroidal neovascularization," Exp Eye Res. Aug. 2004;79(2):275-285.
Chirila et al., "The Vitreous Humor" in *Handbook of Biomaterial Properties,* eds. Black & Hastings. Chapman & Hall, London, 1998; pp. 125-131.
Cousins et al., "Program# 1251—Targeting Complement Factors in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.
Deissler et al., "VEGF-induced effects on proliferation, migration and tight junctions are restored by ranibizumab (Lucentis) in microvascular retinal endothelial cells," Br J Ophthalmol 2008;92:839-843.
Del Amo, et al., Current & future ophthalmic drug delivery systems . . . , *Drug Discovery Today,* vol. 13, Nos. 3/4, Feb. 2008.
Donoso et al., "The role of inflammation in the pathogenesis of age-related macular degeneration," Surv Ophthalmol. Mar.-Apr. 2006;51 (2):137-52.
Duvvuri et al., Drug Delivery to the Retina: Challenges and Opportunities, *Expert Opinion on Biological Therapy,* 2003, vol. 3(1): 45-56.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudana et al. (2008). "Recent Perspectives in Ocular Drug Delivery," *Pharmaceutical Research.* 20 pages.
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Haller, An Overview of Sustained-release Drug Implants, Retinal Physician, Jan. 2008, 4 pages.
Hastedt & Wright, "Diffusion in porous materials above the percolation threshold," Pharm. Res. Sep. 1990; 7(9):893-901 (1990).
Heier et al., "Ketorolac versus prednisolone versus combination therapy in the treatment of acute pseudophakic cystoid macular edema," Ophthalmology. Nov. 2000;107(11):2034-2038;discussion 2039.
Janoria et al. (2007). "Novel Approaches to Retinal Drug Delivery," *Expert Opinion Drug Delivery,* 4(4):371-88.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
Jornitz et al. "Filter Integrity Testing in Liquid Applications, Revisited; Part 1 " *Pharmaceutical Technology.* Oct. 2001. pp. 34-50.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Li, et al., An electrochemical introculardrug delivery device, *Science Direct, Sensors and Actuators,* www.sciencedirect.com, Jul. 4, 2007. pp. 41-48.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency ; retrieved from the Internet:<http://www.ema.europa.eu/docs/en_GB/document_library/EPAR_-_Assessment_Report_-_Variation/human/000715/WC500101009.pdf>. Oct. 21, 2010. 32 pages.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., *Thermophysical Properties of Trehalose and Its Concentrated Aqueous Solutions,*Pharmaceutical Research, vol. 14, No. 5, 1997, pp. 578-590.
Millipore. "Filter Integrity Test Methods." *Millipore Corporation.* 1999. 12 pages.
Molokhia et al., "Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", *Investigative Ophthalmology & Visual Science* 32-6 (1991) pp. 1785-1790.
MOTT Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Nutan, MTH, et al., *General Principles of Suspensions, in Pharmaceutical Suspensions From Formulation Development to Manufacturing,* editors AK Kulshreshtha, et al., Spinger, 2010. 29 pages.
Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.
Rosenfeld, "The Latest Research: Intravitreal Bevacizumab for Proliferative Diabetic Retinopathy," Review of Ophthalmology's Retina Online, Feb. 2006. 2 pages. Retrieved from the Internet: http://www.revophth.com/archive/newsletter/0206_retina.htm.
Saline (medicine). Wikipedia, the free encyclopedia. 2011. Web. Apr. 27, 2012. 4 pages. http://web.archive.org/web/20110205192937/http://en.wikipedia.org/wiki/Saline_(medicine).
Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Sheardown and Saltzman, Novel Drug Delivery Systems for Posterior Segment Ocular Disease, *Opthalmology: Ocular Angiogenesis: Diseases, Mechanisms and Therapeutics,* 2007, pp. 393-408.
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.

(56) References Cited

OTHER PUBLICATIONS

Soheilian et al., "Pilot Study of Intravitreal Injection of Diclofenac for Treatment of Macular Edema of Various Etiologies," Retina, Mar. 2010; 30(3): 509-515.
Stay et al. Computer Simulation of Convective and Diffusive Transport of Controlled-Release Drugs in the vitreous Humor, *Pharm Res* 2003,20(1), pp. 96-102.
Theodossiadis et al., "Intravitreal administration of the anti-tumor necrosis factor agent infliximab for neovascular age-related macular degeneration," Am J Ophthalmol. May 2009;147(5):825-830.
Weiner, A.L., "Chapter 13: Polymeric Drug Delivery Systems for the Eye", *Polymeric Site-Specific Pharmacotherapy,* pp. 315-346, Edited by A.J. Domb (1994) John Wiley & Sons Ltd.
Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.
Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.
Yao et al. (Prevention of Laser Photocoagulation Induced Choroidal Neovascularization Lesions by Intravitreal Doses of Ranibizumab in Cynomolgus Monkeys, ARVO 2009 abstract D906). 2 pages.

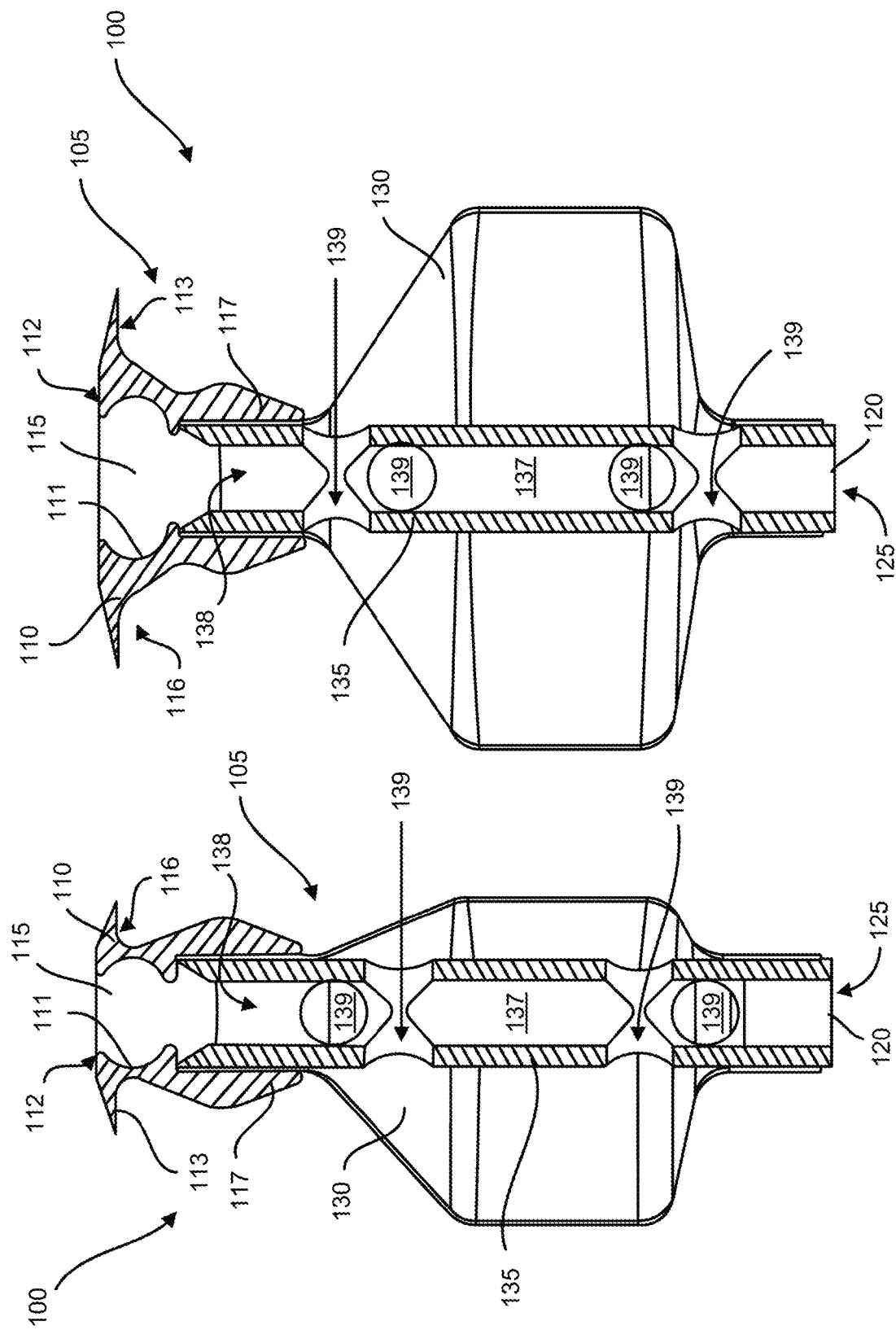

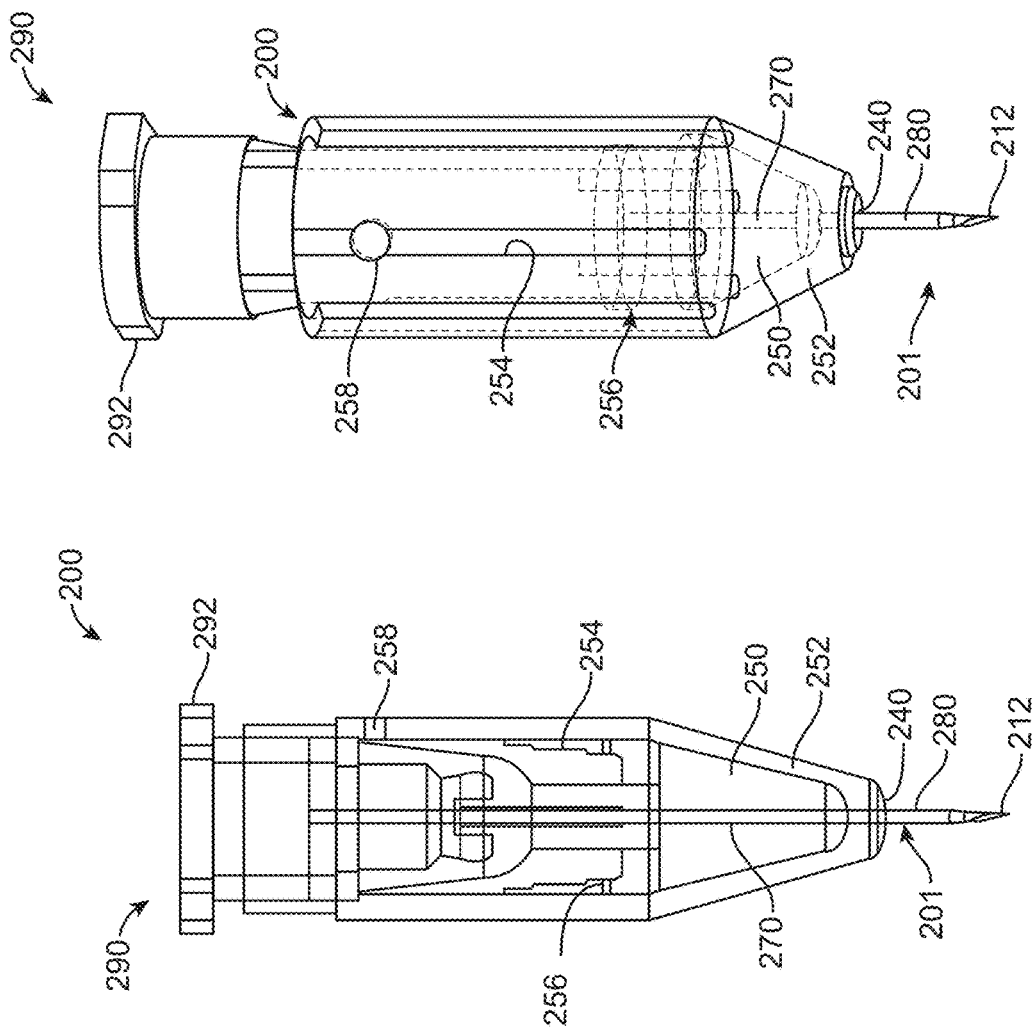

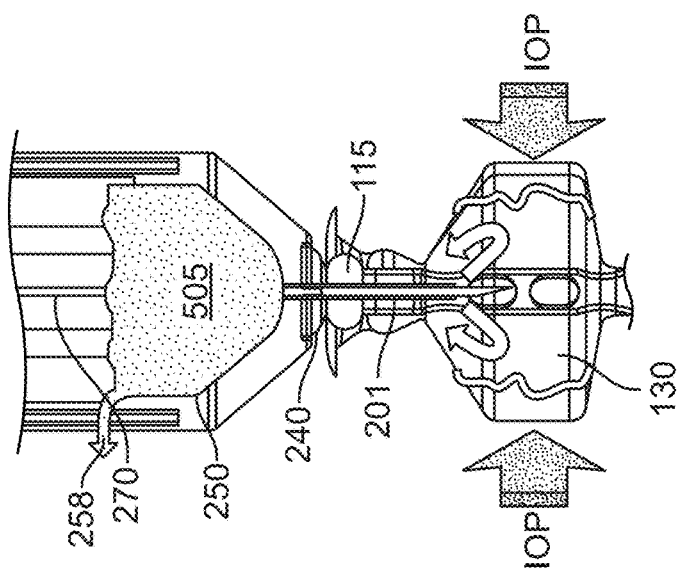
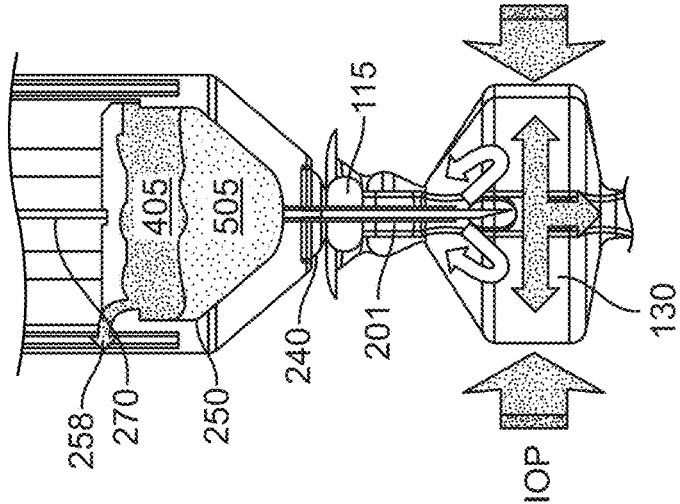
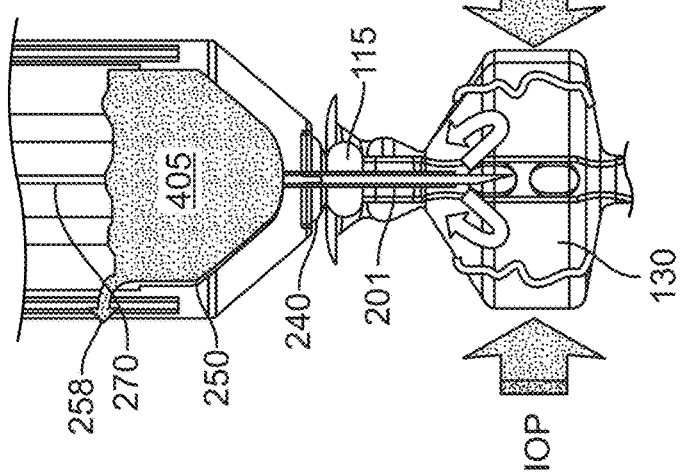

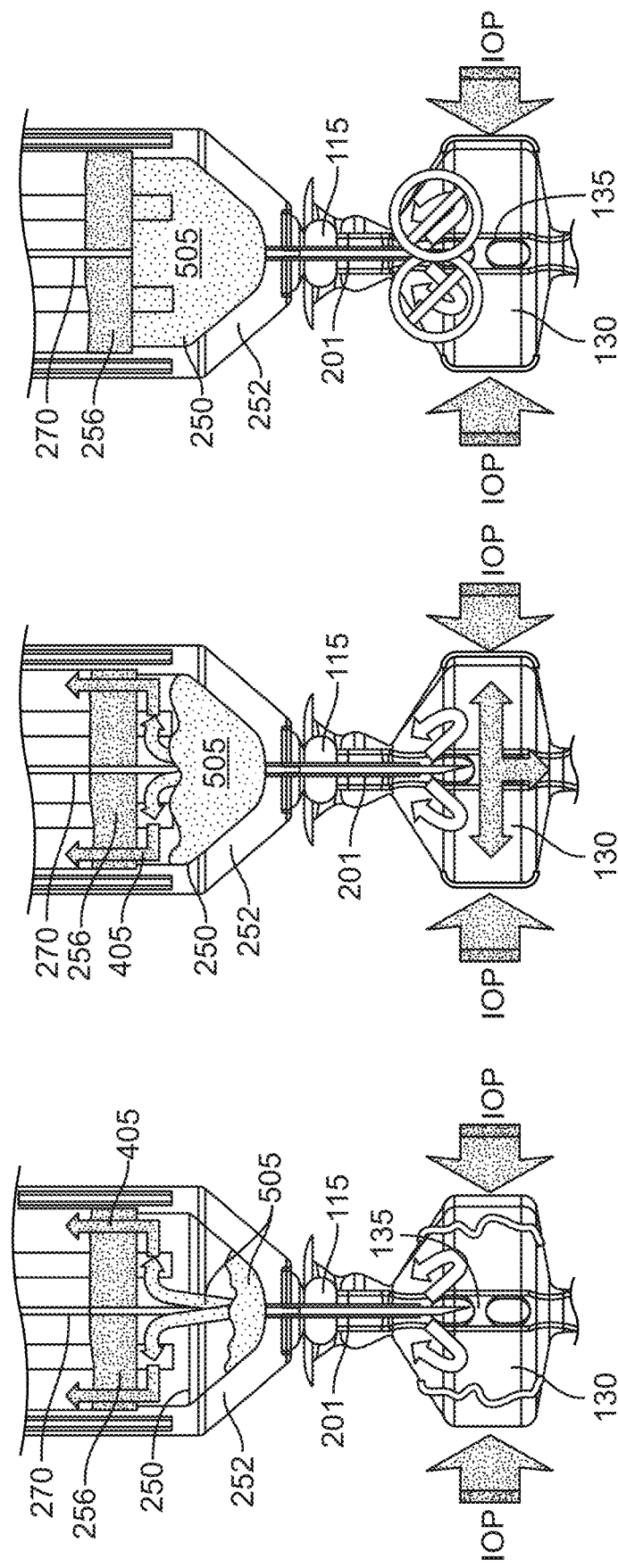

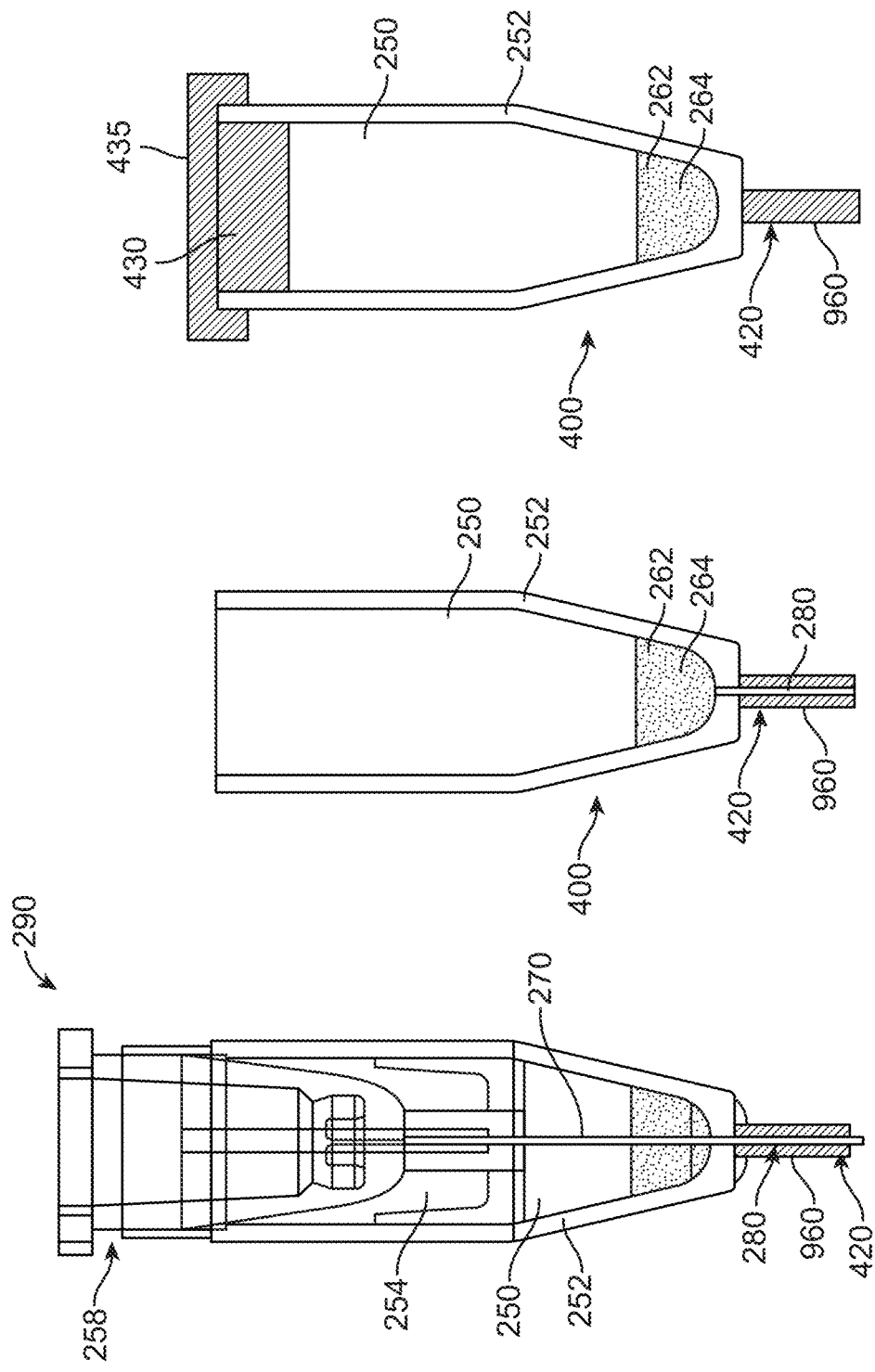

FLUID EXCHANGE APPARATUS FOR EXPANDABLE PORT DELIVERY SYSTEM AND METHODS OF USE

CROSS-REFERENCE TO RELATED APPLICATIONS

This application is a continuation and claims priority to PCT/US2018/061262 filed on Nov. 15, 2018, and claims priority to U.S. Provisional Patent Application Ser. No. 62/589,377, filed Nov. 21, 2017, entitled "Fluid Exchange Apparatus for Expandable Port Delivery System and Methods of Use," the disclosure of which are hereby incorporated by reference in their entirety for all purposes.

BACKGROUND

Diseases that affect vision can be treated with a variety of therapeutic agents, but the delivery of drugs to the eye continues to be challenging. Injections of therapeutic via the eye can be painful, involve some risk of infection, hemorrhage and retinal detachment. Depending on the frequency, intra-ocular injections can be time-consuming for both patient and physician. Consequently, in at least some instances the drug may be administered less often than the prescribed frequency resulting in sub-optimal treatment benefit. Further, bolus intra-ocular injections may not provide the ideal pharmacokinetics and pharmacodynamics. A bolus injection of drug into the vitreous humor of a patient can result in a peak drug concentration several times higher than the desired therapeutic amount and then before the patient is able to get the next injection drop to a drug concentration that is far below therapeutic effectiveness.

SUMMARY

In an aspect, described is a device for injecting a therapeutic agent into an ocular implant, the implant being at least partially implanted in an eye, the implant further providing at least a first resistance to outflow of therapeutic agent into the eye. The device includes an injection lumen configured to provide a pathway for injecting the therapeutic agent into the ocular implant; an outlet lumen configured to provide a pathway through which pre-existing fluid in the ocular implant exits the ocular implant; and a collection chamber fluidly coupled to the outlet lumen. The collection chamber is configured to receive the pre-existing fluid that exits the ocular implant via the outlet lumen. The collection chamber provides a first fluid outflow resistance and a second fluid outflow resistance. The first fluid outflow resistance is lower than the first resistance to outflow of the implant, and the second fluid outflow resistance is greater than a force imparted onto the implant by intraocular pressure of the eye. Injection of therapeutic agent into the ocular implant via the injection lumen causes the pre-existing fluid to exit the ocular implant and enter the collection chamber via the outlet lumen and causes a second pre-existing fluid to displace from the collection chamber.

The implant can be expandable once implanted in the eye from a first, collapsed configuration to a second, enlarged configuration. A first porous structure operatively coupled to the collection chamber can provide the first fluid outflow resistance and the second fluid outflow resistance. The first porous structure operatively coupled to the collection chamber can have the first fluid outflow resistance to gas outflow and the second fluid outflow resistance to liquid outflow. The implant can include a second porous structure that provides the first resistance to outflow. The first fluid outflow resistance of the first porous structure of the collection chamber can be less than the first resistance provided by the second porous structure of the implant. The second fluid outflow resistance of the first porous structure of the collection chamber can be greater than the first resistance of the implant. The second pre-existing fluid can be a gas. The gas can be air. The air can be under vacuum. The second pre-existing fluid can be displaced from the collection chamber via a vent. The second pre-existing fluid can be displaced from the collection chamber via a valve. The implant can be expandable once implanted in the eye from a first, collapsed configuration to a second, enlarged configuration. The first porous structure of the collection chamber can prevent collapse of the implant away from the second, enlarged configuration after filling.

The first porous structure of the collection chamber can be a hydrophobic membrane, a fabric, a porous fabric, a semi-permeable membrane, an air permeable material, a moisture vapor transfer waterproof fabric, a hydrophilic porous material, or a porous sintered material. The first porous structure of the collection chamber can be positioned within an annular element positioned near an upper end of the collection chamber. The annular element can form a fixed upper limit of the collection chamber. The collection chamber can be concentric with a longitudinal axis of the injection lumen. The collection chamber can be offset relative to a longitudinal axis of the injection lumen. The collection chamber can be tubular. The collection chamber can extend between an opening into the tubular collection chamber and terminate at the second porous structure. The tubular structure can have a uniform inner diameter over a length of the tubular structure. The tubular structure can have an inner diameter that enlarges proximally to a second inner diameter. The tubular structure can be coiled. The coiled tubular structure can provide a uniform fill pattern that minimizes trapping of the second pre-existing fluid displaced from the collection chamber.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 7 and 8 are cross-sectional views of the therapeutic device of FIG. 5;

FIGS. 18A-18C illustrate an implementation of an exchange apparatus having a locking connector to couple to a syringe;

FIGS. 19A-19C illustrate collapse of expandable reservoir walls during fluid exchange and loss of payload due to intraocular pressure;

FIGS. 20A-20C illustrate fluid exchange with the exchange needle apparatus of FIG. 18B preventing collapse of expandable reservoir and payload loss;

FIGS. 26A-26C illustrate an implementation of an exchange apparatus having a removable collection chamber.

Figure 1:
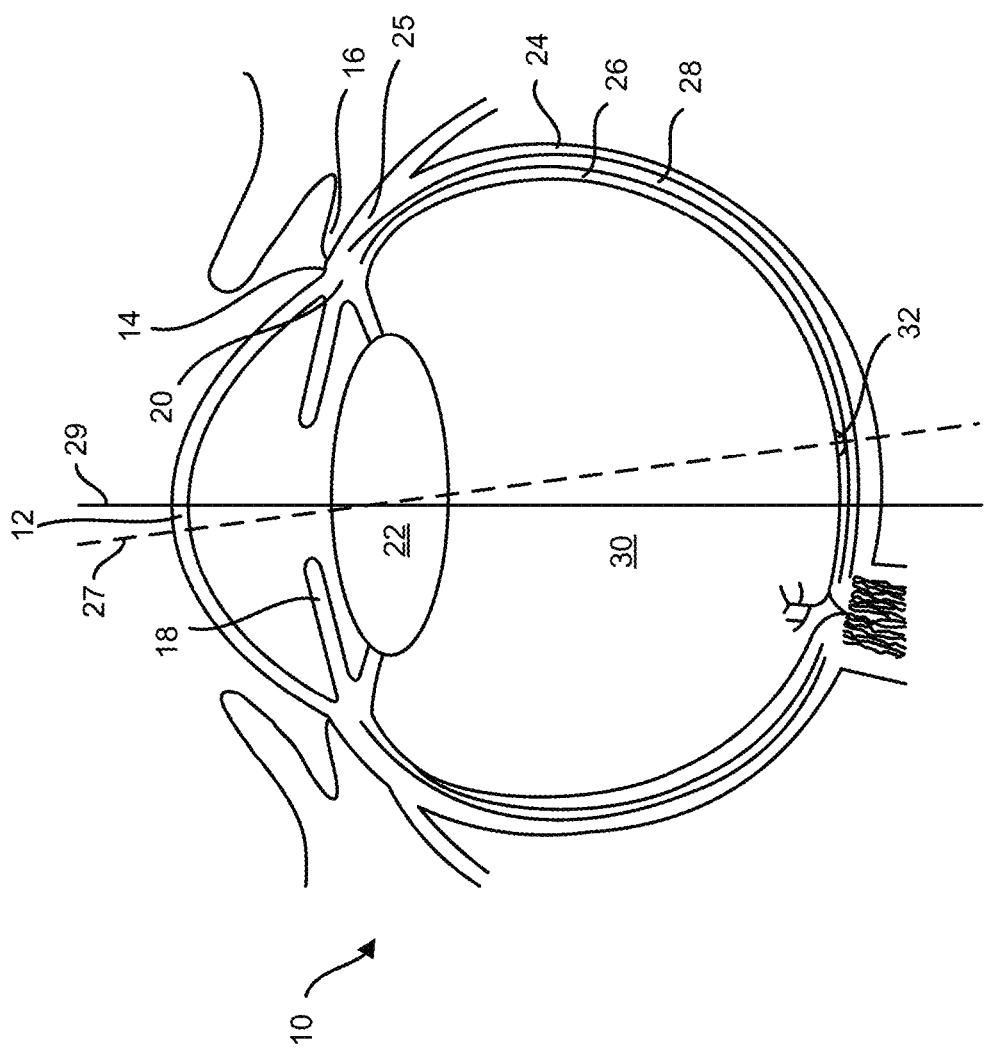
FIG. 1 is a cross-sectional, schematic view of a portion of the human eye.

It should be appreciated that the drawings are for example only and are not meant to be to scale. It is to be understood that devices described herein may include features not necessarily depicted in each figure.

DETAILED DESCRIPTION

Described herein are implantable devices, systems and methods of use for the delivery of one or more therapeutics for the treatment of diseases and methods and apparatus to exchange a fluid of the implantable device.

The devices and systems described herein maximize reservoir volume and capacity while minimizing overall device invasiveness and impact on eye anatomy and vision. In some implementations, the devices described herein include an expandable reservoir that can be compressed into a first configuration for minimally-invasive delivery into the eye, for example, through the sclera and expanded into a second, enlarged configuration upon filling with therapeutic agent following implantation in the eye. When in the second configuration, the reservoir can avoid interfering with the visual axis of the eye as well as remain a safe distance away from certain anatomical structures of the eye so as to avoid damage and impacting vision. As will be described herein, in some implementations the expandable reservoir in the expanded configuration takes on a shape that is eccentric, asymmetrical, or otherwise off-set from the axis of placement of the device into the eye tissue, for example an axis of insertion through the sclera. This off-set can result in a majority of the expanded volume of the reservoir being directed away from certain critical structures of the anterior segment of the eye, for example, the lens, the ciliary body, the choroid, as well as the sclera and surrounding internal tissue layers through which the device was inserted. The expandable reservoir in the expanded configuration can also remain symmetrical or coaxial with a central axis of the device, but can be shaped such that at least a portion of the device is curved, angled, or otherwise off-set relative to the axis of insertion. For example, the expanded reservoir can be shaped into an arc or other curvilinear shape relative to the axis of insertion. Alternatively, the expanded reservoir can be shaped to form an angle relative to the axis of insertion. In these implementations, the overall length of the device can be increased while still remaining outside the visual axis or significantly impacting the visual field. These and other features of the devices described herein will be described in more detail below.

After an amount of time, the fluid of the implantable device may be replaced exchanged, or the device otherwise refilled to provide additional amounts of therapeutic agent to extend the therapy. Described herein are apparatus and methods to place therapeutic fluids in a device already implanted in the eye. The apparatus provides improved sampling and replacement of the fluid with optimum exchange efficiency, little or no leakage resulting from the pressure of the injection, and a clinically acceptable exchange time.

It should also be appreciated that the devices and systems described herein can be positioned in many locations of the eye and need not be implanted specifically as shown in the figures or as described herein. The devices and systems described herein can be used to deliver therapeutic agent(s) for an extended period of time to one or more of the following tissues: intraocular, intravascular, intraarticular, intrathecal, pericardial, intraluminal and intraperitoneal. Although specific reference is made below to the delivery of treatments to the eye, it also should be appreciated that medical conditions besides ocular conditions can be treated with the devices and systems described herein. For example, the devices and systems can deliver treatments for inflammation, infection, and cancerous growths. Any number of drug combinations can be delivered using any of the devices and systems described herein.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Definitions

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the devices and is not intended to be limited. For example, as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any pharmaceutical use of the devices described and provided herein.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms. Pharmaceutically effective amount, therapeutically effective amount, biologically effective amount and therapeutic amount are used interchangeably herein to refer to an amount of a therapeutic that is sufficient to achieve a desired result, i.e. Therapeutic effect, whether quantitative or qualitative. In particular, a pharmaceutically effective amount, in vivo, is that amount that results in the reduction, delay, or elimination of undesirable effects (such as pathological, clinical, biochemical and the like) in the subject.

As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a porous structure.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

As used herein, a composition refers to any mixture. It can be a solution, a suspension, an emulsion, liquid, powder, a paste, aqueous, non-aqueous or any combination of such ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

Eye Anatomy

FIG. 1 is a cross-sectional, schematic view of a portion of the human eye 10 showing the anterior chamber, posterior chamber and vitreous body of the eye. The eye 10 is generally spherical and is covered on the outside by the sclera 24. The bulk of the eye 10 is filled and supported by the vitreous body 30 (referred to herein as vitreous humor or just vitreous), a clear, jelly-like substance disposed between the lens 22 and the retina 26. The retina 26 lines the inside posterior segment of the eye 10 and includes the macula 32. The retina 26 registers the light and sends signals to the brain via the optic nerve. The fovea centralis is the part of the eye located in the center of the macula 32 of the retina 26 and is the region responsible for sharp central vision, for example in order to read or drive. An imaginary line passing from the midpoint of the visual field to the fovea centralis is called the visual axis 27. The hypothetical straight line passing through the centers of curvature of the front and back surfaces of the lens 22 is the optic axis 29.

The elastic lens 22 is located near the front of the eye 10. The lens 22 provides adjustment of focus and is suspended within a capsular bag from the ciliary body 20, which contains the muscles that change the focal length of the lens 22. A volume in front of the lens 22 is divided into two by the iris 18, which controls the aperture of the lens 22 and the amount of light striking the retina 26. The pupil is a hole in the center of the iris 18 through which light entering anteriorly passes. The volume between the iris 18 and the lens 22 is the posterior chamber. The volume between the iris 18 and the cornea 12 is the anterior chamber. Both chambers are filled with a clear liquid known as aqueous humor.

The cornea 12 extends to and connects with the sclera 24 at a location called the limbus 14 of the eye. The conjunctiva 16 of the eye is disposed over the sclera 24 and the Tenon's capsule extends between the conjunctiva 16 and the sclera 24. The eye 10 also includes a vascular tissue layer called the choroid 28 that is disposed between a portion of the sclera 24 and the retina 26. The ciliary body 20 is continuous with the base of the iris 18 and is divided anatomically into pars plica and pars plana 25, a posterior flat area approximately 4 mm long.

Figure 2:
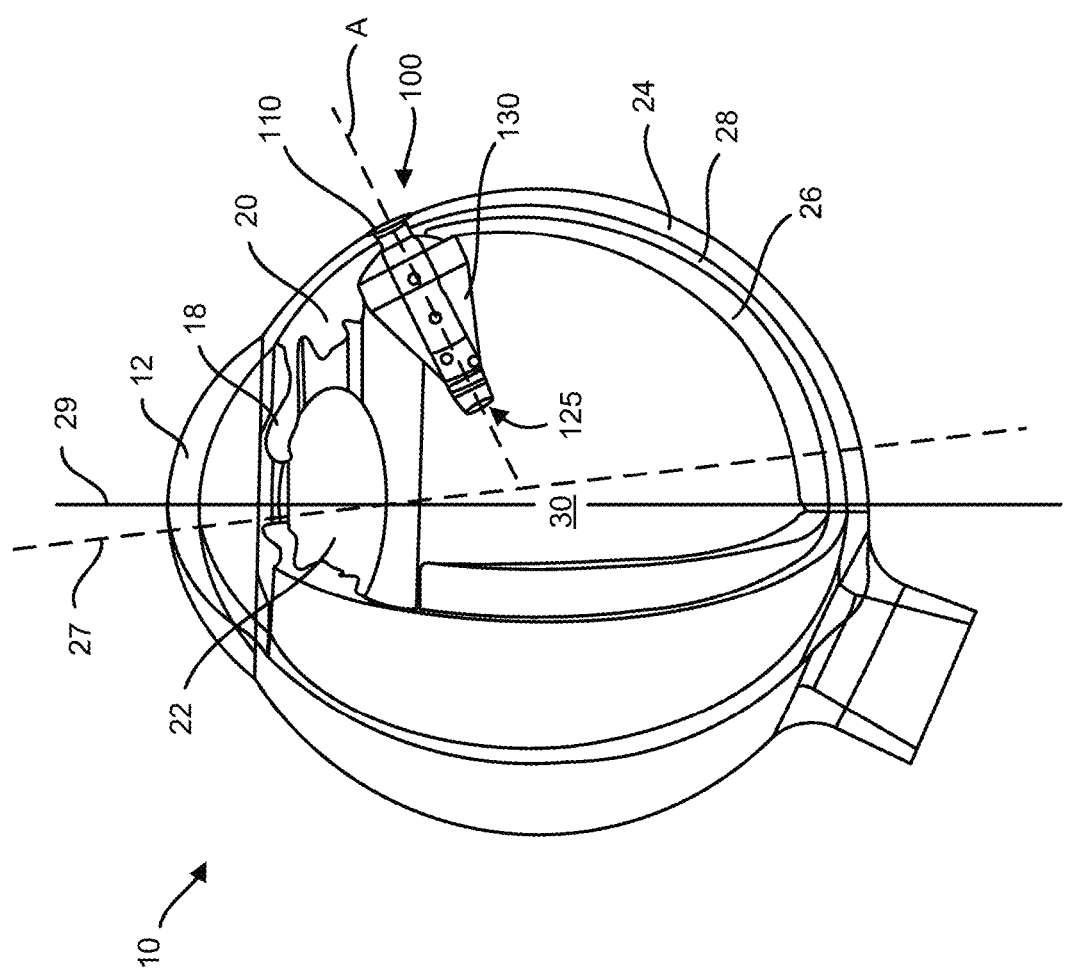
FIG. 2 is a partial, cross-sectional, schematic view of a portion of the eye having an implementation of a therapeutic device at least partially implanted within the sclera of the eye along an axis of insertion A.

The devices described herein can be positioned in many locations of the eye 10, for example in the pars plana region away from tendon of the superior rectus muscle and one or more of posterior to the tendon, anterior to the tendon, under the tendon, or with nasal or temporal placement of the therapeutic device. As shown in FIG. 2, the devices described herein can be positioned along an axis of insertion A through the sclera 24 in the pars plana region and expanded such that the device avoids interfering with the visual field, and in particular, the visual and optic axes 27, 29.

Surgical placement of trans-scleral ocular implants designed to penetrate the globe such that certain regions of the implant occupy supra-scleral, trans-scleral, sub-scleral, and intravitreal aspects of the ocular anatomy in the pars plana region involves a risk of acute vitreous hemorrhage (VH) following surgery. The devices described herein incorporate one or more features that mitigate the risk of vitreous hemorrhage at the time of surgical implantation and lead to improved healing following surgery.

Treatment Devices

The devices described herein are referred to as drug delivery devices, treatment devices, therapeutic devices, port delivery systems, and the like. It should be appreciated that these terms are used interchangeably herein and are not intended to be limiting to a particular implementation of device over another. The devices and systems described herein can incorporate any of a variety of features described herein and the elements or features of one implementation of a device and system described herein can be incorporated alternatively or in combination with elements or features of another implementation of a device and system described herein as well as the various implants and features described in U.S. Pat. Nos. 8,399,006; 8,623,395; PCT Pat. Publication No. WO 2012/019136; PCT Pat. Publication No. WO 2012/019047; PCT Pat. Publication No. WO 2012/065006; U.S. Publication No. 2016/0128867; and U.S. Provisional Application Ser. No. 62/318,582. For the sake of brevity, explicit descriptions of each of those combinations may be omitted although the various combinations are to be considered herein. For example, the devices described herein can include non-rigid walled reservoirs configured to enlarge following implantation such as by filling with treatment solution. The expandable reservoirs described herein may be used with any of the various implementations of a device or system. Further, reference to an expandable reservoir can include a reservoir wall that is pliable and able to be folded, compressed, contracted, etc. into a low profile configuration that is suitable for insertion into the eye in a manner that minimizes the size of penetration. The wall of an expandable reservoir may be pliable or flexible, but need not be stretchy or elastomeric in order to enlarge in size to hold the treatment solution. The expandable reservoir can include a reservoir wall that tents, unfolds, expands, stretches, or otherwise enlarges the overall cross-sectional size of the reservoir compared to the low profile configuration suitable for insertion. It should be appreciated that the terms unfold, expand, enlarge, and other terms used to refer to this shape change of the reservoirs described herein may be used interchangeably.

Additionally, described herein are different methods for implantation and access of the devices. The various implants can be implanted, removed, filled, refilled, aspirated, and/or flushed, etc. according to a variety of different methods and using a variety of different devices and systems. Provided are some representative descriptions of how the various devices may be implanted and accessed, however, for the sake of brevity explicit descriptions of each method with respect to each implant or system may be omitted.

The porous structures (also referred to herein as a drug release mechanism, drug release element, release control element, RCE, or frit) as described herein can be used with a number of various different implantable therapeutic devices including one or more of those devices described U.S. Pat. Nos. 8,399,006; 8,623,395; PCT Pat. Publication No. WO 2012/019136; PCT Pat. Publication No. WO 2012/019047; and PCT Pat. Publication No. WO 2012/065006; the entire disclosures of which are incorporated herein by reference thereto.

Figure 3:
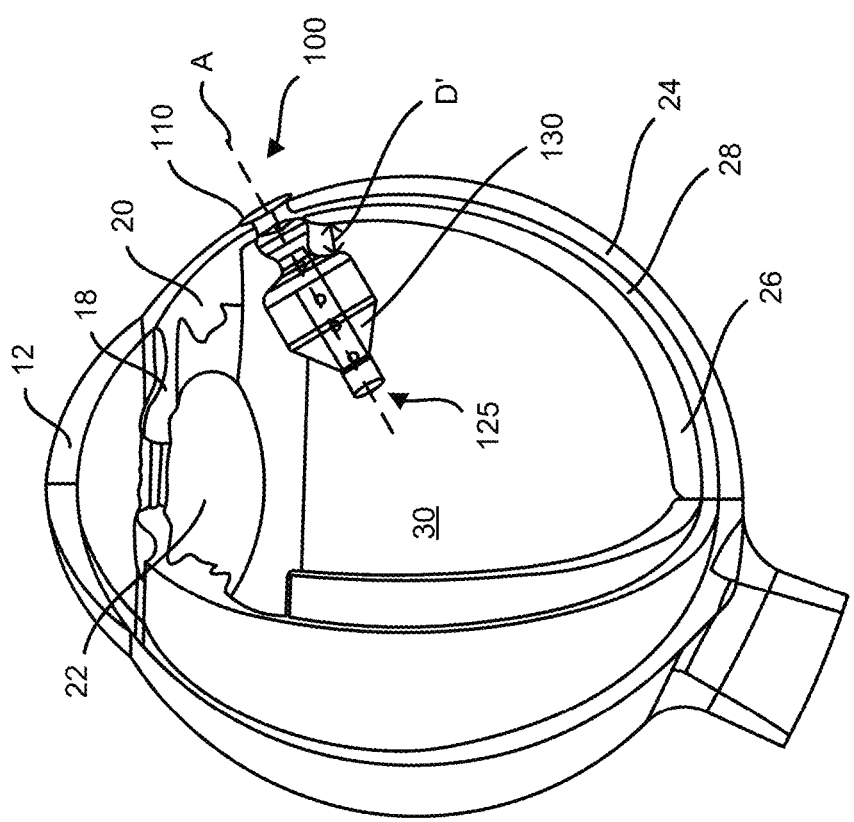
FIG. 3 is a partial, cross-sectional, schematic view of a portion of the eye having another implementation of a therapeutic device at least partially implanted within the sclera of the eye along an axis of insertion A.
Figure 5:
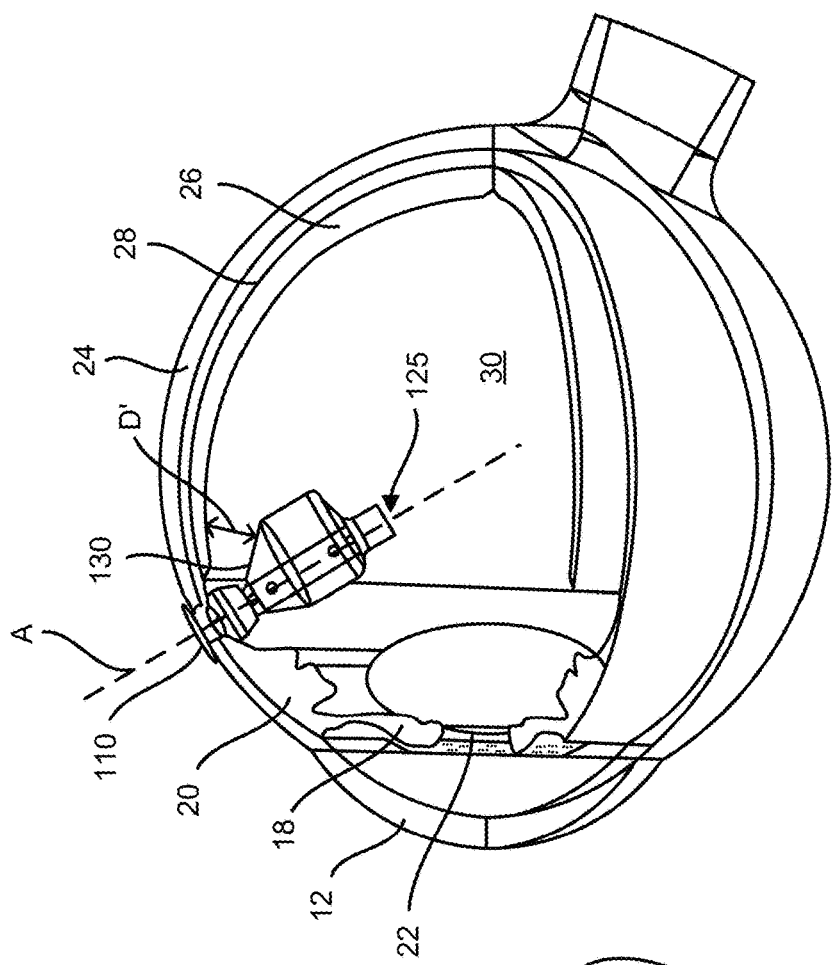
FIGS. 4 and 5 are partial, cross-sectional, schematic views of a portion of the eye having another implementation of a therapeutic device at least partially implanted within the sclera of the eye along an axis of insertion A.
Figure 4:
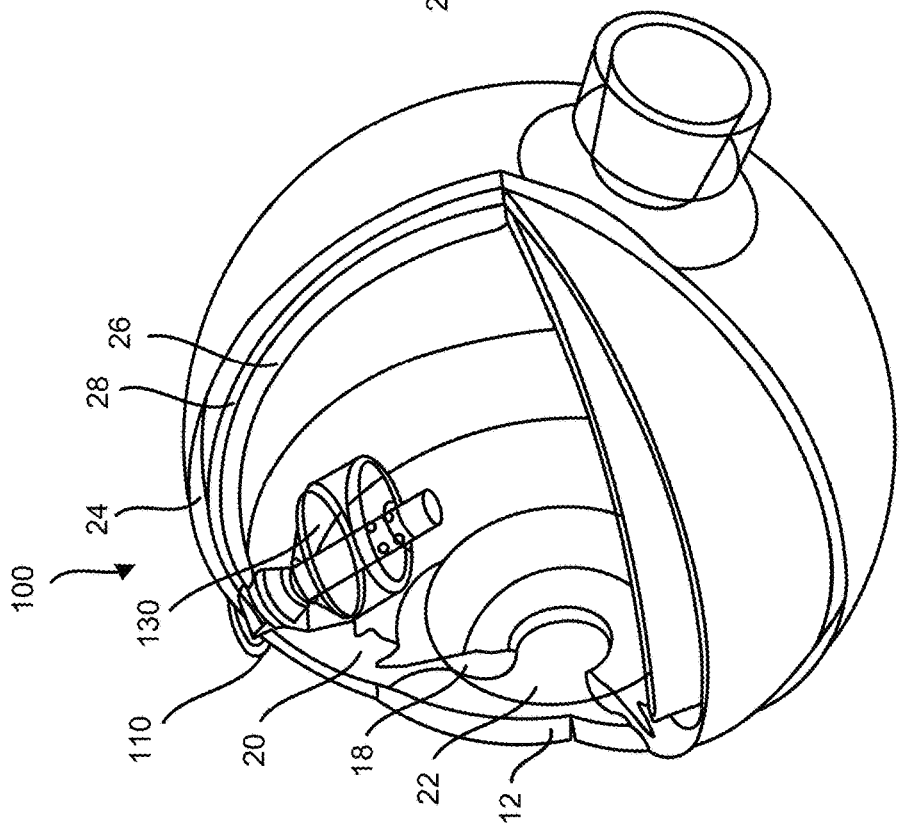
Figure 6:
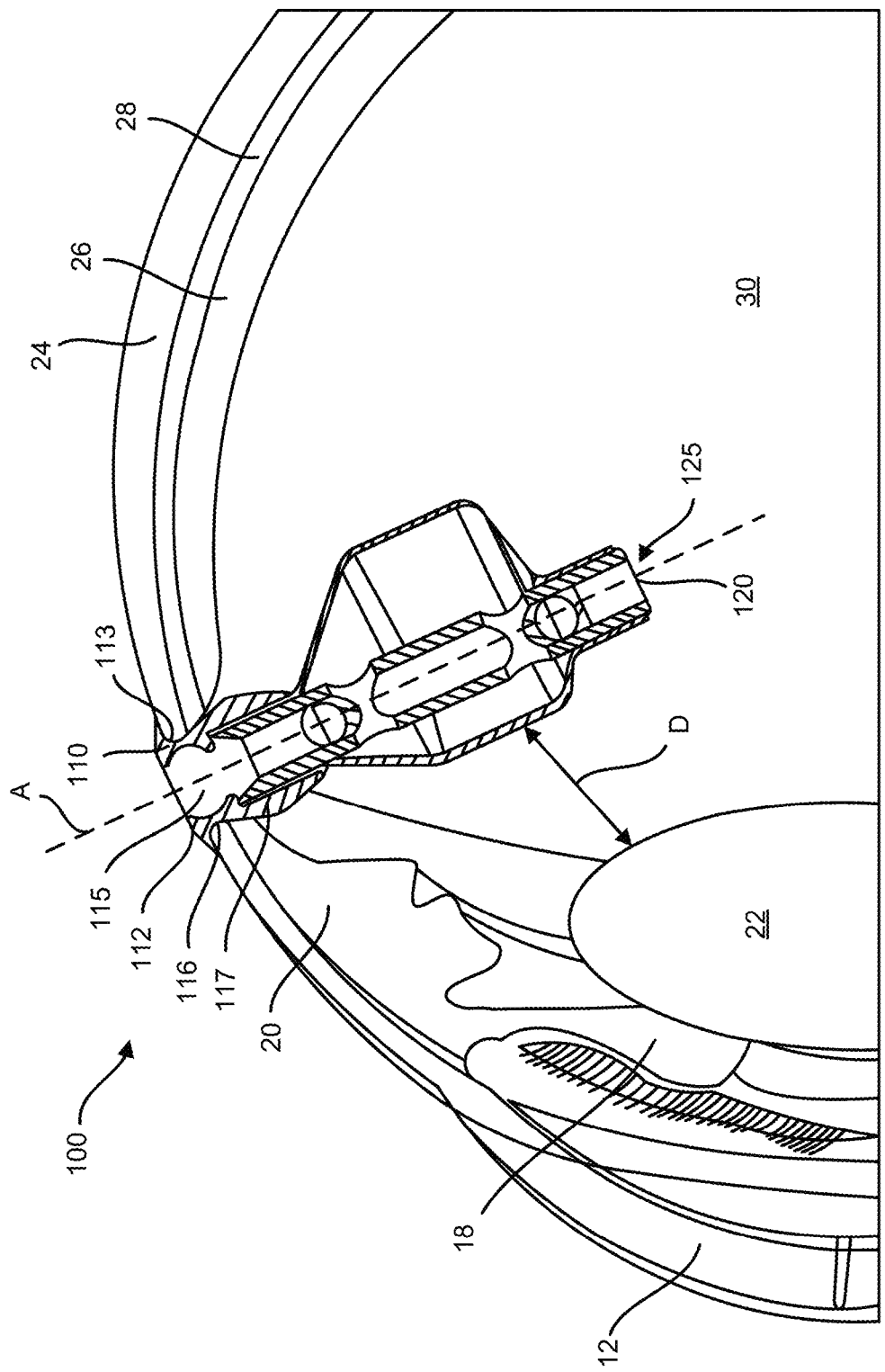
FIG. 6 is a cross-sectional view of the therapeutic device of FIG. 5.

FIGS. 2 and 3 as well as FIGS. 4-9 illustrate implementations of an expandable treatment device 100 configured to deliver one or more therapeutic agents to one or more regions of the eye 10. The device 100 can include a proximal retention structure 105 having a smooth protrusion or flange element 110, a porous drug release element 120, and an expandable reservoir 130. An access port 111 can extend through the retention structure 105 and a penetrable element 115 can be positioned within at least a portion of the access port 111. The penetrable element 115 and the access port 111 allow for access to an inner volume of the reservoir 130, for example, to fill, refill, aspirate, and/or flush materials in the reservoir 130. In some implementations, the access port 111 can be formed by an opening through the retention structure 105 into the reservoir 130 and covered by a penetrable material and/or the penetrable element 115. The penetrable element 115 can be a septum configured to be penetrated and resealed such that material does not leak out of the reservoir 130 following penetration of the material during in situ refilling of the reservoir 130. Alternatively, one or more regions of the flange element 110 itself can be formed of a penetrable material.

The drug release element 120 can be positioned in a variety of locations within the device 100 such that the volume of the reservoir 130 is in fluid communication with the drug release element 120. For example, the drug release element 120 can be positioned near a distal end region of the device 100 such as within an outlet 125 of the device 100, for release of the one or more therapeutic agents contained within the reservoir 130 into the eye. The drug release element 120 can also be positioned in a region of the device proximal of the distal end region. The drug release element 120 can also be positioned towards a particular area to be treated, such as the retina.

The device 100 can be implanted in the eye such that at least a portion of the device 100, for example the reservoir 130, the drug release element 120 and one or more outlets 125, are positioned intraocularly. In some implementations, the device 100 can be positioned so as to extend through the sclera 24 from the pars plana region so as to release the therapeutic agent into the vitreous body 30. As mentioned above, the device 100 can be positioned in the eye along an axis of insertion A (see FIG. 6). The flange element 110 can form a smooth protrusion configured for placement along the sclera 24. The flange element 110 can remain generally external to the eye to aid in retention of the device 100 while the remainder of the device 100 is at least partially positioned intraocularly. The flange element 110 can have any of a variety of shapes, for example, oval, ovoid, elliptical, circular, or other shape as will be discussed in more detail below. In some implementations, the flange element 110 can be generally curved so as to have a contour along a surface of a sphere. An outer-facing surface 112 of the flange element 110 can have a convex shape and an inner-facing surface 113 can have a concave shape such that the flange element 110 can better conform to the curvature of the eye. In other implementations, the flange element 110 can be generally flat. The edges of the flange element 110 can be generally smooth and rounded. In some implementations, when the flange element 110 is positioned such that the inner-facing surface 113 of the flange element 110 can contact the sclera 24 and the outer-facing surface 112 of the flange element 110 can be positioned under the conjunctiva 16 (not shown in FIG. 6) such that the conjunctiva 16 covers the outer-facing surface 112 of the flange element 110 and protects the therapeutic device 100. The conjunctiva 16 covering the outer-facing surface 112 of the flange element 110 can allow access to the device 100 while decreasing the risk of infection to the patient. When the therapeutic agent is inserted or injected into the device 100 through the access port of the flange element 110, the conjunctiva 16 may be lifted away, incised, or punctured with a needle to access the therapeutic device 100.

As best shown in FIGS. 7 and 8, the retention structure 105 can include the proximal flange element 110 as well as a neck positioned adjacent the flange element 110. The neck can include a proximal region 116 and a distal extension 117. The proximal region 116 of the neck can be sized along a cross-section to fit a penetration site through the sclera 24, such as an incision and/or a puncture. For example, the proximal region 116 can be narrowed relative to the flange element 110 to fit more snugly within the penetration site in the sclera 24. FIG. 7 shows a first cross-sectional view of the narrowed proximal region 116 of the neck. FIG. 8 shows a second cross-sectional view of the narrowed proximal region 116 of the neck taken along a plane orthogonal to the first cross-sectional view. The proximal region 116 of the neck can have a first cross-sectional distance across when taken along a first plane and a second cross-sectional distance across when the cross-section is taken along a second, orthogonal plane and the first cross-sectional distance can be different from the second cross-sectional distance. The distance across the proximal region 116 of the neck is shorter in the view of FIG. 7 (minor axis) compared to the distance across the proximal region 116 of the neck in the view of FIG. 8 (major axis). In some implementations, the cross-sectional shape of the proximal region 116 of the neck can complement a shape of the incision, puncture or other penetration site through which the device 100 is inserted. The cross-sectional shape of the proximal region 116 of the neck can be elongated, including but not limited to one of a lentoid, oval, and ellipse shape. In some implementations, the cross-sectional shape of the proximal region 116 of the neck is a first curve along a first axis and a second curve along a second axis that is different from the first curve. U.S. Pat. No. 8,277,830 and also U.S. Provisional Application Ser. No. 62/318,582, filed Apr. 5, 2016, which are incorporated by reference herein in their entirety, describes further details regarding the geometry of the proximal region of the devices described herein. It should be appreciated that the dimensions of the neck or trans-scleral region of the devices described herein can vary as well be described in more detail below.

As mentioned above, the neck of the retention structure 105 can also include a distal extension 117. The distal extension 117 of the neck can extend inside the eye a distance away from the inner surface of the sclera 24 at the penetration site. As described above and as best shown in FIG. 6, the flange element 110 can form a smooth protrusion configured for placement along the sclera 24. The proximal portion 116 of the neck can fit within the penetration site of the sclera 24 such that the tissue being penetrated is received snugly within the proximal portion 116 of the neck. The distal extension 117 can be arranged coaxial with the insertion axis A of the device and can extend a distance away from the proximal portion 116.

The distal extension 117 of the neck can provide stabilization to the penetrable region of the device 100 while eliminating contact between the expandable reservoir 130 and inner surfaces of the eye adjacent the proximal end of the device 100. FIG. 2 shows an implementation of a device 100 having a reservoir 130 that in the expanded configuration makes contact with one or more internal surfaces of the eye adjacent the proximal end of the device 100. The proximal end of the reservoir 130 can wedge against the internal tissue surfaces surrounding the penetration site through the sclera 24 and can act to stabilize the penetrable region of the device 100. In some implementations, contact between the reservoir 130 and the internal tissue surfaces is prevented to avoid irritation and/or damage of the delicate tissues of the eye. For example, as shown in FIG. 3, the proximal end of the reservoir 130 in the expanded configuration can be separated or off-set a distance D' from one or more internal tissue surfaces surrounding the penetration site. The distal extension 117 of the neck can aid in preventing contact between portions of the device 100 and tissues adjacent the penetration site while still providing stabilization to the penetrable region of the device 100. For example, the distal extension 117 of the neck can be sufficiently long and contoured such that the reservoir 130 of the device is located a distance away from the adjacent tissue layers of the penetration site even when the reservoir 130 is in the expanded configuration. In some implementations, the distal extension 117 of the neck has a length and contour configured to prevent any portion of the device 100 distal to the extension 117 from contacting any of the internal structures of the eye except the vitreous 30 within which it is implanted. In some implementations, upon implantation and expansion of the device 100 in the eye, the flange element 110 and the proximal region 116 of the neck come into contact with the tissue layers of the eye (e.g. conjunctiva, sclera, ciliary body, and/or choroid. The distally extending portions of the device 100, such as the reservoir 130, the drug release element 120, and distal portions of the extension 117, may avoid contact with the tissue layers of the eye and come into contact only with the vitreous 30. The shape of the reservoir 130 in the expanded configuration can also aid in preventing this contact as will be discussed in more detail below.

As mentioned above, the devices described herein can include one or more drug release elements 120. The drug release element 120 can be positioned adjacent and/or within the one or more outlets 125 such that the drug release element 120 can control or regulate the delivery of the one or more therapeutic agents from the reservoir 130 through the one or more outlets 125. The contents of the reservoir 130 can be delivered gradually via diffusion rather than expelled as a fluid stream. In some implementations, the one or more drug release elements 120 can be disposed within a region of the reservoir 130, such as a distal end region, or a region proximal to the distal end region of the device. In some implementations, the drug release element 120 can be a covering or lining having a particular porosity to the substance to be delivered and can be used to provide a particular rate of release of the substance. The drug release element 120 can be a release control element, including but not limited to a wicking material, permeable silicone, packed bed, small porous structure or a porous frit, multiple porous coatings, nanocoatings, rate-limiting membranes, matrix material, a sintered porous frit, a permeable membrane, a semi-permeable membrane, a capillary tube or a tortuous channel, nano-structures, nano-channels, sintered nanoparticles and the like. The drug release element 120 can have a porosity, a cross-sectional area, and a thickness to release the one or more therapeutic agents for an extended time from the reservoir. The porous material of the drug release element 120 can have a porosity corresponding to a fraction of void space formed by channels extending through the material. The void space formed can be between about 3% to about 70%, between about 5% to about 10%, between about 10% to about 25%, or between about 15% to about 20%, or any other fraction of void space. The drug release element 120 can be selected from any of the release control elements described in more detail in U.S. Pat. No. 8,277,830, which is incorporated by reference herein.

As mentioned above, the devices described herein include a reservoir 130 configured to expand, unfold, or otherwise enlarge from a generally minimally-invasive insertion configuration to an expanded configuration with an increased volume. The insertion configuration of the devices described herein has a three-dimensional shape that is relatively low profile such that the device 100 can be inserted at least partially into the eye using a small gauge device, or directly into the eye through a small incision. Many of the devices described herein can be inserted using an incision or puncture that is minimally-invasive, for example in a range of about 1 mm to about 5 mm. In some implementations, the incision is a 3.2 mm incision. It should also be appreciated that in some implementations, the device 100 can have column strength sufficient to permit the device 100 to pierce through eye tissue without an internal structural support member or members. The device can be inserted through the sclera 24 without a prior incision or puncture having been made in the eye. For example, the device can be inserted using a needle cannula member extending through an interior of the device and the drug release element 120 pressed or secured inside at a distal tip of the cannula member.

Generally, when in the insertion configuration the portion of the device 100 configured to penetrate the eye (e.g. the reservoir 130) can have a smaller cross-sectional diameter compared to the cross-sectional diameter of the portion of the device 100 configured to remain external to the eye (e.g. the flange element 110). In some implementations, the cross-sectional diameter of the reservoir 130 (e.g. collapsed around a central core element 135 as will be described in more detail below) in the insertion configuration can be about 1.3 mm to about 1.5 mm in diameter, the diameter of the proximal portion 116 of the neck can be about 2.7 mm long and about 1.5 mm wide, and the flange element 110 can be about 4.5 mm long and about 3.8 mm wide. In some implementations, the device 100 can be approximately 25 gauge such that the device 100 can be inserted through a needle bore. In this implementation, the flange element 110 can be of a resilient material (such as shape memory or a flexible silicone) such that it can be housed in the needle bore during implantation and released out the distal end of the needle bore at which point the flange element 110 can retake its shape. Further, the cross-sectional shape of the eye-penetrating portion of the device 100 when in the insertion configuration can vary including circular, oval, or other cross-sectional shape. Also, when in the insertion configuration the device 100 can have a substantially uniform diameter along its entire length or the cross-sectional dimension and shape can change along the length of the device 100. In some implementations, the shape of the device 100 in the insertion configuration can be selected to facilitate easy insertion into the eye. For example, the device 100 can be tapered from the proximal end region to the distal end region.

The length of the device 100 can vary depending on where and how the device 100 is to be implanted in the eye. Generally, the length is selected so as not to impact or enter the central visual field or cross the visual axis 27 of the eye upon implantation and filling of the device 100. In some implementations, the total length of the device can be between about 2 mm to about 10 mm. In some implementations, the total length of the device can be between about 3 mm to about 7 mm. In some implementations, the length of the intraocular region of the device is about 4 mm to about 5 mm long.

The reservoir 130 of the devices described herein can enlarge into a particular contour or shape that can maximize its overall capacity while minimizing its impact on the internal eye anatomy. The insertion configuration of the reservoir 130 can have a first three-dimensional shape and the expanded configuration can have a second three-dimensional shape that is different from the first. Again with respect to FIGS. 2 and 3, the reservoir 130 in the expanded configuration can be generally symmetrical relative to the insertion axis A. In this implementation, both the first three-dimensional shape and the second three-dimensional shape can be generally concentric with the longitudinal axis of the device 100 and the insertion axis A. In another implementation as shown in FIGS. 4-9, the reservoir can be configured to enlarge from an insertion configuration having a first three-dimensional shape to an expanded configuration having a second three-dimensional shape, wherein the second three-dimensional shape is eccentrically positioned or generally asymmetrical relative to the insertion axis A. In this implementation, the first three-dimensional shape can be generally concentric with the insertion axis A and the second three-dimensional shape can be eccentric with the insertion axis A. Depending on the folding approach used to obtain the low profile insertion configuration of the reservoir, the first three-dimensional shape of the symmetrical or eccentric reservoirs may be offset as opposed to generally concentric. The first three-dimensional shape of the generally symmetrical reservoir 130 may be slightly offset from the longitudinal axis of the device and the insertion axis A such that even though the reservoir expands into a generally symmetrical second three-dimensional shape, the first three-dimensional shape is somewhat non-concentric. The same can be true for the eccentrically positioned reservoir 130. The first three-dimensional shape may depend on the overall shape of the reservoir 130 as well as on the folding approach used to obtain the low profile insertion configuration and can be somewhat non-concentric.

Figure 9:
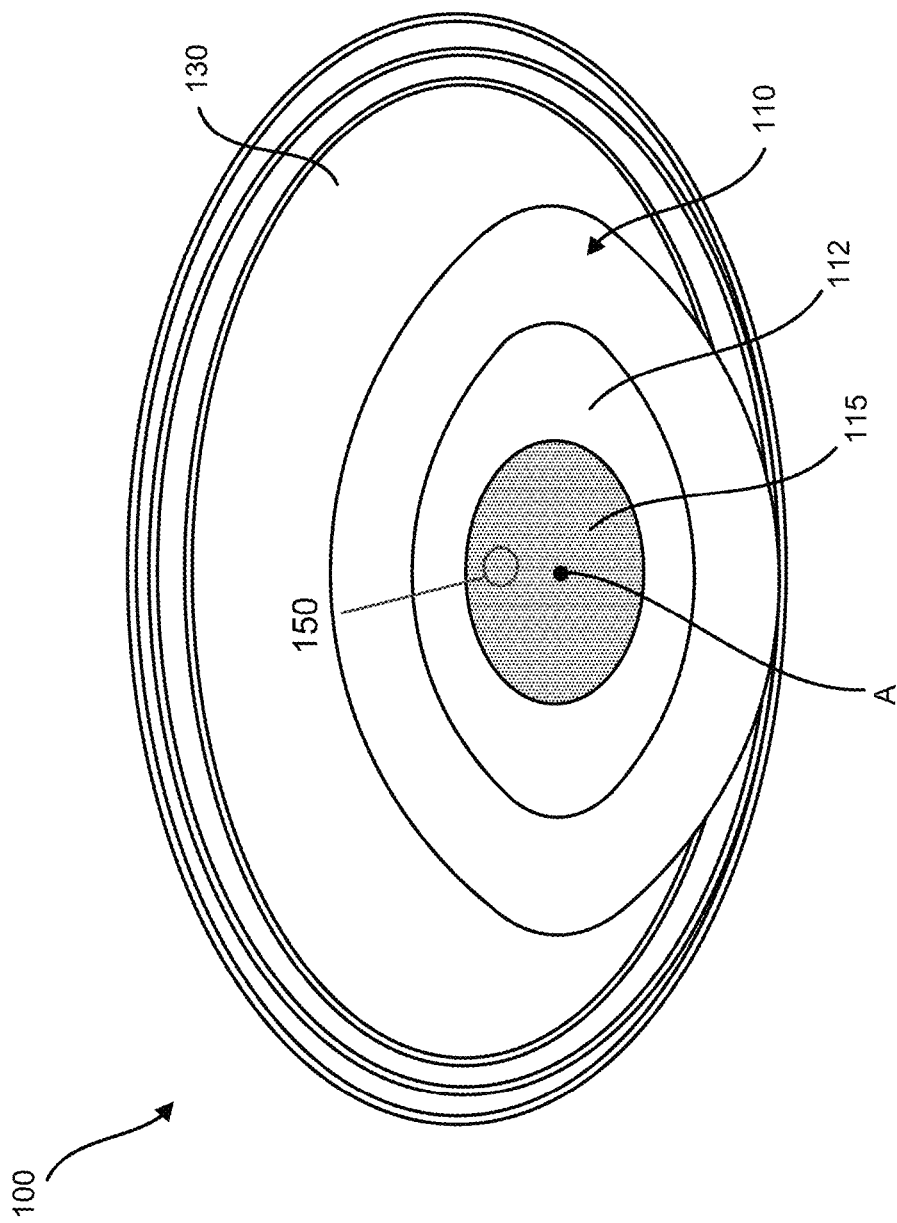
FIG. 9 is a top down view of the therapeutic device of FIG. 5.

FIG. 9 shows a top down view of a device 100 and illustrates an axis of insertion A. A plane can be drawn parallel to the axis of insertion A and orthogonal to the surface of the sclera 24 through which the device is inserted. In some implementations, more of the expanded volume of the reservoir 130 can be located on a first side of this plane than on the opposite side of this plane such that the expanded volume on the first side extends towards a posterior region of the eye or enlarges away from the lens 22 of the eye such that contact with the lens 22 is mitigated (see, e.g. FIG. 5 and also FIG. 13). Thus, a portion of the overall volume of the reservoir 130 in the expanded configuration enlarged away from the lens of the eye and is greater than the remaining portion of the reservoir 130 volume. Further, the reservoir 130 can enlarge such that a majority of the reservoir volume extends away from the inner surface of the sclera through which the device was inserted such that the expanded reservoir 130 avoids contacting interior surfaces of the eye that can contribute to choroidal effusions, hemorrhage or cause other unintentional contact, damage or irritation between the eye and the device 100, such as with the ciliary body or choroid. Further, when in the expanded configuration the entire reservoir 130 can remain generally outside the central visual field, such as outside the visual axis of the eye.

The expandability of the reservoir 130 from a low profile dimension for insertion to an expanded profile dimension after insertion allows for the device to be inserted in a minimally-invasive manner and also have an increased reservoir capacity. This increased reservoir capacity, in turn, increases the duration of drug delivery from the device for a given release control element such that the device 100 need not be refilled as frequently, and/or can reach the targeted therapeutic concentration of drug in the eye. In some implementations, the volume of the reservoir 130 can be between about 0.5 µL to about 100 µL. In some implementations, the volume of the reservoir 130 can be at least about 1 µL, 2 µL, 3 µL, 4 µL, 5 µL, 10 µL, 15 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 96 µL, 97 µL, 98 µL, 99 µL, 100 µL, 105 µL, 110 µL, 115 µL, 120 µL, 125 µL, or other volume.

An outer wall of the reservoir 130 can be formed of a substantially non-compliant material that is expandable yet rigid and/or non-distensible material. As such, the reservoir 130 can be filled into the expanded configuration, but the material of the reservoir 130 is configured to maintain its shape and does not stretch so as to avoid an unintentional driving force created by the memory of the wall material of the reservoir 130. In other implementations, the outer wall of the reservoir 130 can be a compliant material such that a controllable pressure can be provided by the compliant wall of the reservoir 130 up to the point of pressure equalization, for example, to provide a small initial boost of drug delivery from the reservoir after filling. Examples of expandable, non-distensible, substantially non-compliant materials are provided herein, including but not limited to PET, Nylon, and acrylics. Examples of expandable, compliant materials are also provided herein, including but not limited to silicone, urethane, and acrylics.

In some implementations, the volume of the reservoir 130 and the shape of the reservoir 130 in the expanded configuration are selected to maximize the payload capacity as well as maximizing the distance away from the lens 22 and/or the sclera 24 adjacent the penetration site. For example, in some implementations, the volume of the reservoir 130 can be 60 µL and the shape of the reservoir 130 in the expanded configuration can be D-shaped, C-shaped, elliptical, eccentric, or other shape that can extend away from the insertion axis A of the device (see FIG. 6). Thus, compared to a symmetrically expanded reservoir of smaller capacity, the eccentric or asymmetrically expanded reservoir 130 can maintain a greater distance D away from the lens 22. The reservoir 130 in the expanded configuration also can be tapered on a proximal end to maximize the distance D' the expanded reservoir 130 is off-set from the sclera 24 through which the device extends. Maintaining a greater distance D' helps to prevent contact between the expanded reservoir 130, for example the proximal end of the expanded reservoir 130, and the internal tissue surfaces surrounding the penetration site and other neighboring tissue layers of the eye such as the retina 26, choroid 28, sclera 24, ciliary body 20, and/or the lens 22. The proximal tapering of the reservoir 130 also allows for improved removal of the device 100 from the eye. The shape of the reservoir 130 can alternatively or additional be tapered on a distal end. A distal end taper can further help the device to avoid entering the visual axis and avoid contact with certain internal structures such as the lens. Further, a smooth and gradual transition to the end of the device can also improve the ease of insertion as will be described in more detail below.

As best shown in FIGS. 7 and 8, the devices described herein can include a central core element 135 extending between the proximal end region of the device 100 and the distal end region of the device 100. The central core element 135 can be a generally cylindrical and relatively rigid element positioned around a longitudinal axis of the device 100 such that it is generally concentric with the axis of insertion A. The central core element 135 can include an inner lumen 137 and one or more openings 139 extending through a wall of the central core element 135. In some implementations, the central core element 135 can include an inlet 138 on a proximal end positioned relative to the penetrable element 115 in the access portion to receive material injected into the device, which will be described in more detail below. The inlet 138 or a portion of the central core element 135 near the inlet 138 can be surrounded by the distal extension 117 of the retention structure 105. The central core element 135 can also include an outlet located a distance away from the inlet 138 that can form the outlet 125 from the device 100, for example near a distal end of the central core element 135. The drug release element 120 can be positioned within the outlet such that therapeutic agent can be released from the reservoir 130 into the eye. The central core element 135 can protect the material of the reservoir 130 from unintended penetration or puncture. For example, during filling a portion of the central core element 135 near the inlet 138 can receive a fill needle configured to inject material into the device. The central core element 135 can be formed of a material that is relatively rigid and less likely to snag on the sharp tip of the fill needle compared to the substantially non-compliant yet thinner material of the reservoir 130. Thus, the rigid core element 135 can prevent penetration of reservoir material near the inlet 138 by the needle during filling. The core element 135 can also aid in surgical control during insertion and/or removal by providing a degree of rigidity along the longitudinal axis A of the device.

Figure 16:
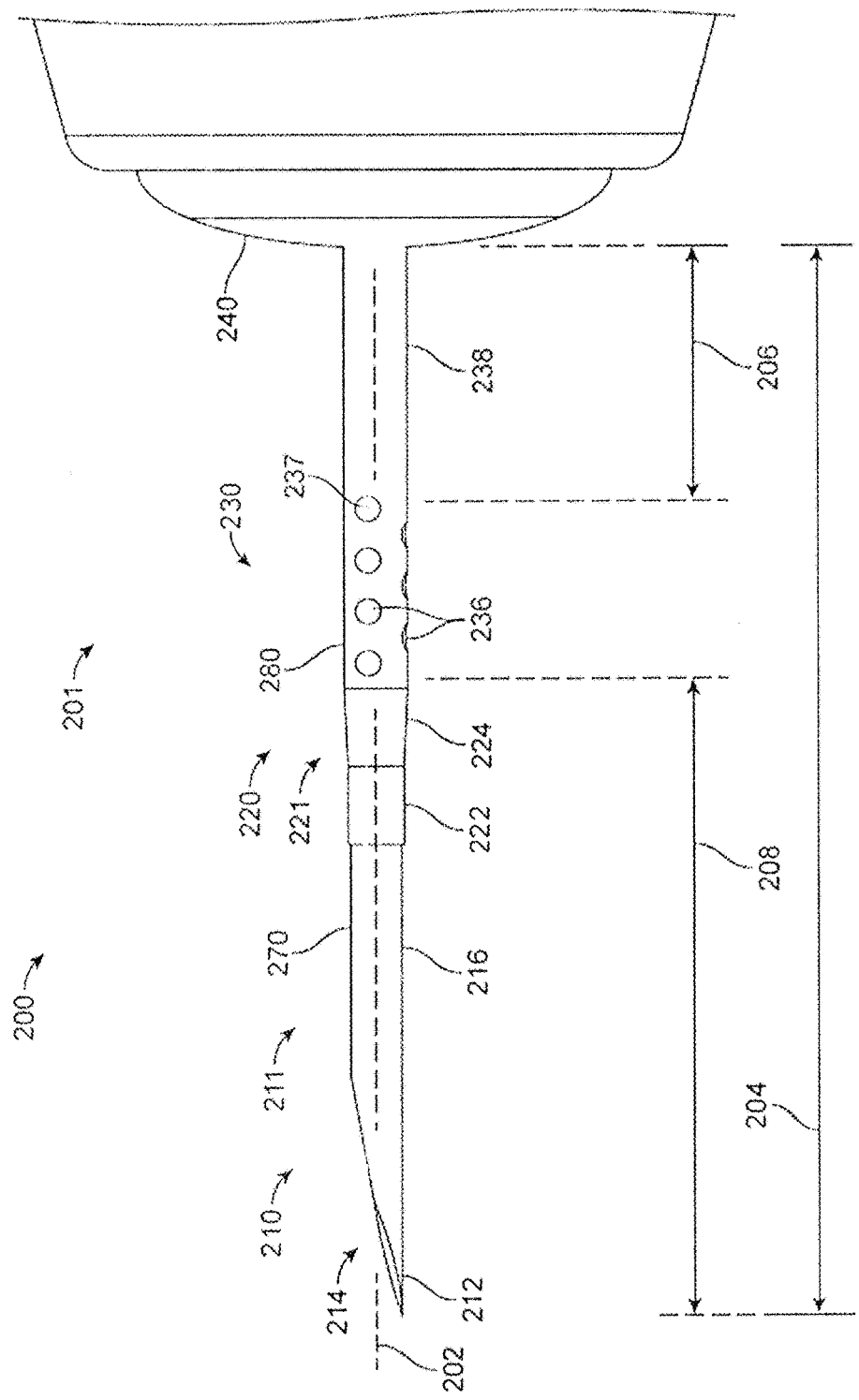
FIG. 16 is a detail view of an elongate structure of the apparatus of FIG. 15.

The one or more openings 139 in the wall of the central core element 135 allow for fluid communication between the inner lumen 137 of the central core element 135 and the reservoir 130. Material introduced through the penetrable element 115 such as via a delivery element can be injected within the lumen 137 and the flow of fluid directed through the one or more openings 139 into the reservoir 130. The introduction of material into the reservoir 130 expands the inner volume of the reservoir 130 and causes the pliable walls of the reservoir 130 to move away from the longitudinal axis of the device and/or move away from the central core element 135. Expansion of the reservoir volume changes the reservoir from the initial, insertion configuration to the expanded configuration, which will be described in more detail below. Optimizing the size of the one or more openings 139 in relation to the diameter of the inner lumen 137 can help to direct flow through the central core element 135 through the one or more openings 139 into the reservoir 130. The size and number of the one or more openings 139 can vary. In some implementations, the opening(s) 139 through the wall of the central core element 135 are smaller in diameter than an outer diameter of the insertion tool 1400 and/or an outer diameter of the needle 270 of the exchange needle apparatus 200. This prevents the insertion tool 1400 or needle 270 from inadvertently inserting through the opening(s) 139. The smaller size openings 139 can protect against punctures or other damage to the flexible reservoir 130 from the insertion tool 1400 and/or the tip 212 of the needle 270 (FIG. 16). The smaller size of the one or more openings 139 can be compensated for by increasing the number of openings 139 present. In some implementations, the central core element 135 can have at least about 2 openings 139, at least about 10 openings 139, at least about 20, 30, 40, 50, up to about 100 openings 139 extending through the wall of the central core element 135. In some implementations, at least about 1000 openings 139 can extend through the wall of the central core element 135. The openings 139 can be less than 150 um openings. In some implementations, the openings 139 can be about 10 um up to about 150 um. The smaller and more numerous openings 139 prevent the tip 212 of the needle 270 or the insertion tool 1400 from protruding through opening(s) 139 in the wall of the central core 135 during use. The opening(s) 139 can be any geometric shape (or combinations of shapes) and distributed in any arrangement or pattern in the wall of the central core 135. A few specific configurations are shown in FIGS. 7, 8, 10, and 11 for exemplary purposes only. Many other configurations are possible as understood by those of skill in the art.

Figure 10:
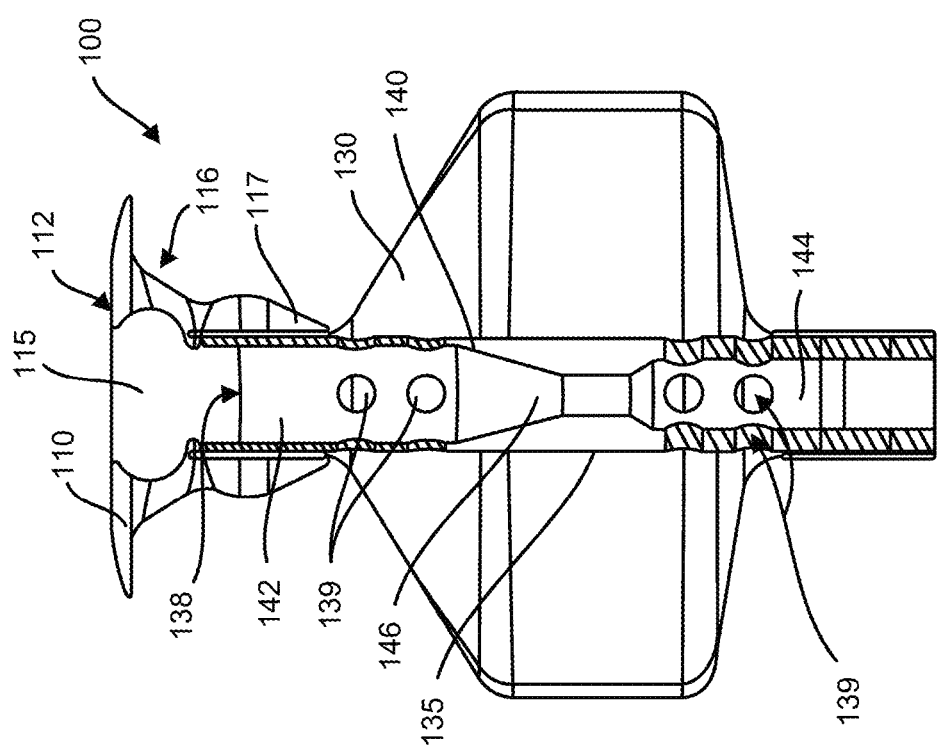
FIG. 10 is a cross-sectional view of another implementation of a therapeutic device having an implementation of a flow director.
Figure 11:
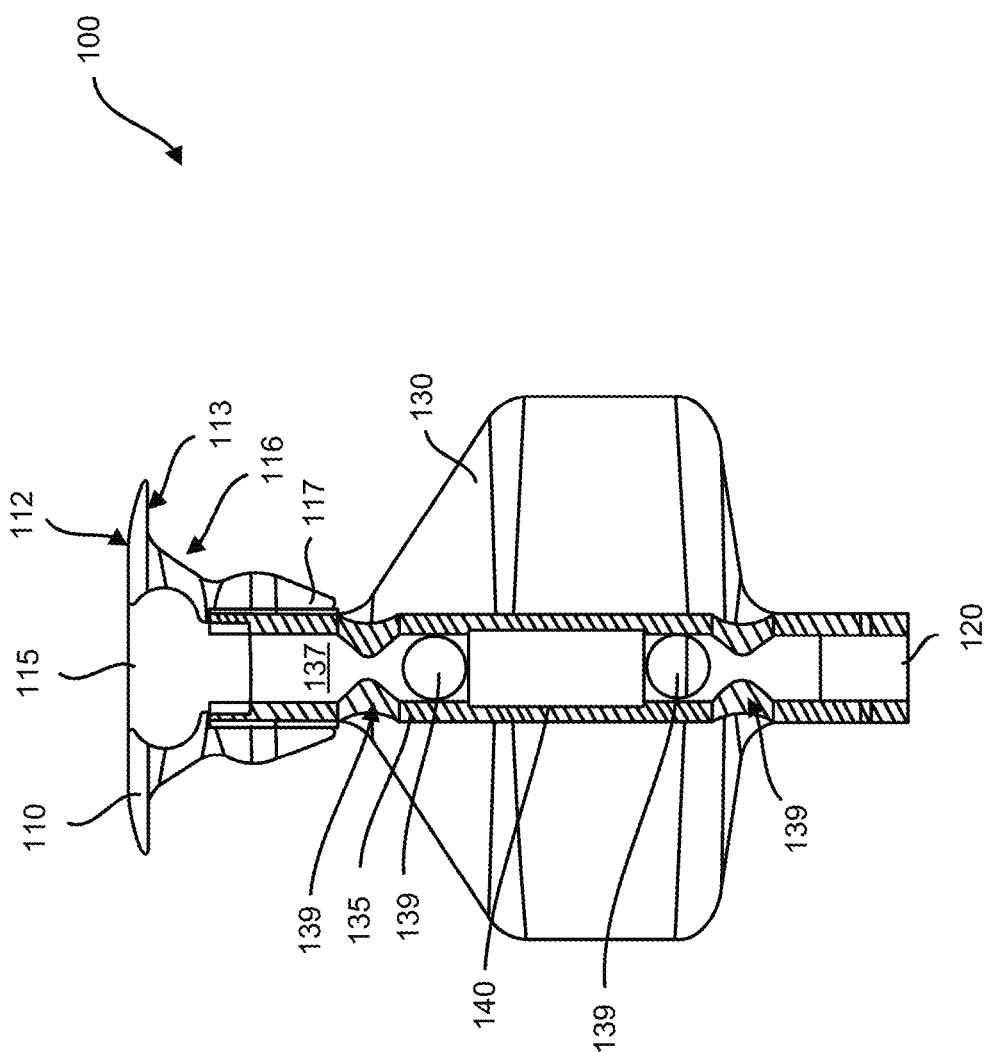
FIG. 11 is a cross-sectional view of another implementation of a therapeutic device having another implementation of a flow director.

The central core element 135 can also include a flow director 140 to facilitate filling/refilling of the reservoir 130 and increase efficiency of filling/refilling (see FIG. 10).

In some implementations, the flow director 140 can include a first cylindrical region 142 coupled to a second cylindrical region 144 by a funnel shaped region 146 to direct flow through the one or more openings 139. The first cylindrical region 142 can be positioned proximal to the second cylindrical region 144 the second cylindrical region 144. The first cylindrical region 142 can have a larger cross-sectional diameter than the second cylindrical region 144. Further, the one or more openings 139 of the flow director 140 can be smaller in size than in an implementation of the device without a flow director 140. In another implementation, the flow director 140 positioned within the inner lumen 137 of the central core element 135 can be a penetrable barrier, for example an element through which a delivery element extends (see FIG. 11). In this implementation, the flow director 140 can be a silicone element that has an outer diameter sized and shaped to wedge within the inner lumen 137 of the core element 135. For example, the flow director 140 that is a penetrable element can be penetrated by a fill/refill needle or other delivery element such that the device 100 can be filled/refilled from the bottom up. The material can be initially injected in a distal end region of the device until the proximal end region of the device is also filled and expanded. The fill/refill needle is described in more detail below.

The devices described herein having a flow director 140 or other core structure with optimized openings 139 can leverage paths of least resistance for evacuation of pre-existing materials from the device being filled. This, in turn, can improve refill efficiency at lower refill volumes for example, by preventing backflow and/or directing bottom-up or bottom-first filling. Bottom-up filling can be improved, even without the presence of a flow director, by leveraging fluid density differences of the liquids being exchanged. The fluid density of the new solution being added to a device can be greater than the fluid density of the pre-existing material in a device. Temperature differences between the liquids being exchanged impact fluid density as well and can be leveraged to improve exchange efficiency in bottom-up filling. For example, the temperature of the pre-existing material in the device is at body temperature whereas the temperature of the new solution can be at room temperature or colder temperatures such that it is denser compared to the warmer material in the device. These density differences allow for bottom-up filling/exchange to occur in a more efficient manner with less mixing. Additionally or alternatively, high volume exchange can be used to flush and/or refill the device with a new solution.

In some implementations, implant orientation and/or tilt angle during refilling can improve the refill efficiency of the reservoir, particularly where there is a solution density difference between the fluid being injected and the contents of the implant remaining in the reservoir prior to refill. The patient can be positioned during a refill procedure to maintain the implant reservoir (or a majority of the reservoir) below the level of the proximal openings in the implant core (i.e. the openings nearest the septum). The refill of the implant can be performed similarly as an intravitreal injection. The needle path penetration techniques used is generally along the longitudinal axis of the implant to avoid snagging the needle tip on the inner core. The implant can be positioned through the sclera with the elongate cross-sectional profile aligned with an incision along the pars plana so as to extend from the pars plana region into the vitreous. Refill of the implant can be performed by inserting the refill needle along the longitudinal axis of the device. The patient having an implant extending through the sclera of an eye such that the reservoir positioned within the vitreous can be oriented relative to gravity to maintain a majority of the reservoir below the level of the proximal openings in the core to achieve the greatest refill efficiency.

In some implementations, controlled aspiration of the reservoir 130 can be used to improve refill efficiency. Aspiration can improve refill efficiency without relying on fluid density differences, high volume exchange, and/or a flow director. For example, aspiration can be applied to remove material from the reservoir chamber prior to filling the device with new solution. The new solution can be injected into the reservoir chamber emptied by aspiration, such as by applying positive pressure through an injection lumen. Optionally or additionally, the new solution can be drawn into the reservoir chamber as a result of the aspiration used to evacuate the pre-existing material from the reservoir chamber. This evacuation and refilling can be a two-step process (i.e. aspiration step to evacuate followed by an injection step to fill) or can be performed in an essentially one-step process (i.e. aspiration step to evacuate leading to filling by drawing fluid into the reservoir). For example, a vacuum can be applied through a first channel in the exchange apparatus such that new solution is drawn in from a reservoir through a second channel of the exchange apparatus. The configuration of such an exchange apparatus can vary.

The configuration of the flow director 140 can vary. The central core 135 can include one or more directional fins or projections internal to the central core 135. The projections in the central core 135 can change direction of flow out the openings in the central core 135. For example, the projections can slope towards the openings to direct flow towards the distal edges of the walls of the reservoir 130. The projections can optimize flow patterns of injected therapeutic agent and encourage additional mixing in possible low-flow regions of the device. In bottom-up type exchange as described above, it is desirable to minimize mixing between the pre-existing material in the device with the new solution being added. However, in some instances some degree of mixing between the pre-existing material and the new solution may be desirable. The device may have regions where displacement during exchange is difficult due to geometry of the interior of the device (e.g. corners, edges) and some mixing with the flow director 140 may be helpful during the exchange.

As mentioned above, the treatment devices described herein can be held by an insertion tool and inserted through the puncture or incision into the target region. As such, the distal end region of the devices can be shaped in order to ease initial wound entry. A distal end region of the device having a larger diameter and/or a flatter distal tip can be more difficult to find and insert through an incision or puncture as small as 3.2 mm. Further, abrupt edges in the outer contour of the device due to bonding between structural elements of the device (e.g. where a distal edge of the reservoir material bonds to the central core element) can negatively impact tissue entry. In some implementations, the distal end region of the treatment device is beveled, tapered or has a bullet-point tip or other element such that it smoothly penetrates the tissue during implantation.

As mentioned above, the central core element 135 can be bonded at a proximal end to an upper portion of the reservoir 130 and at a distal end to a lower portion of the reservoir 130. The bond between the central core element 135 and the reservoir 130 as well as the central core element 135 and the drug release element 120 can be achieved by adhesives such as a two-part epoxy like Epotech 301. In some implementations, thermal fusing between the components is used. For example, if the central core element 135 and the reservoir material can both be made from thermally bondable materials, such as nylon or polysulfone (PSU), the two may be thermally bonded together using heat and compression providing a simpler manufacturing process and more reliable bond than adhesive. The central core element 135 also can be formed of a metal material and designed to accept the flow of plastic such that it can be joined to the reservoir using heat and compression despite not be formed of the same thermally bondable material. In some implementations, the distal and/or proximal region of the central core element 135 can incorporate a plurality of small holes to accept the flow of a polymer material such as a small hole pattern laser drilled into the core. If the reservoir material and the central core element are made from similar materials or the core has features designed to accept the flow of a polymer material an ultrasonic welding process can be used to provide energy required to create the bond between them. In further implementations, the central core element 135 can be formed of a thermoplastic that can allow for the development of an over-molding process between the drug release element 120 to create a bond joint between the drug release element 120 and the central core element 135 at the distal end of the device.

Figure 12:
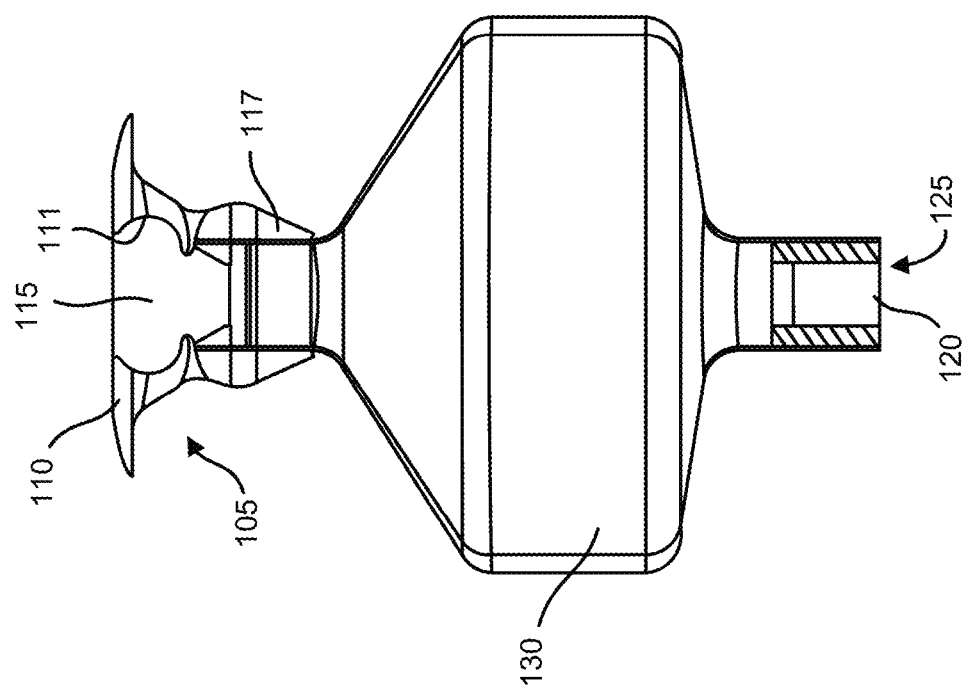
FIG. 12 is a cross-sectional view of another implementation of a therapeutic device.

It should be appreciated that the devices described herein need not include a flow director 140 or a central core element 135. For example, FIG. 12 shows an implementation of a device 100 having an expandable reservoir 130 coupled on a proximal end to a retention structure 105 having a flange element 110, a penetrable barrier 115 positioned within an access port 111 and a distal extension 117. The expandable reservoir 130 is coupled on a distal end region to an outlet 125 having a drug release element 120 positioned therein. However, there is no central core element 135 or flow director 140 incorporated. The material of the reservoir 130 can provide sufficient rigidity to the device such that it can be inserted through a penetration site along an axis of insertion A without collapsing in on itself or warping away from the insertion configuration or axis of insertion A. In some implementations, the material of the reservoir 130 is Polyethylene terephthalate (PET) and has a wall thickness in the range of about 0.0005 mm to about 0.05 mm such that the device has column strength and is generally rigid enough to insert into the eye without a central core element or flow director. In some implementations, the devices described herein can be implanted using a stylet or other rigid, longitudinal element that can be inserted within a region of the reservoir at the time of placement and then removed once the necessary column strength has been imparted and the device has penetrated through the sclera. The material of the reservoir 130 can also include Urethane, Nylon, Pebax®, Polyurethanes, cross-linked polyethylene, FEP, PTFE, and similar materials and blends of materials. The materials may also include multiple layers of the above materials and other materials known in the art for manufacturing expandable elements.

Figure 13:
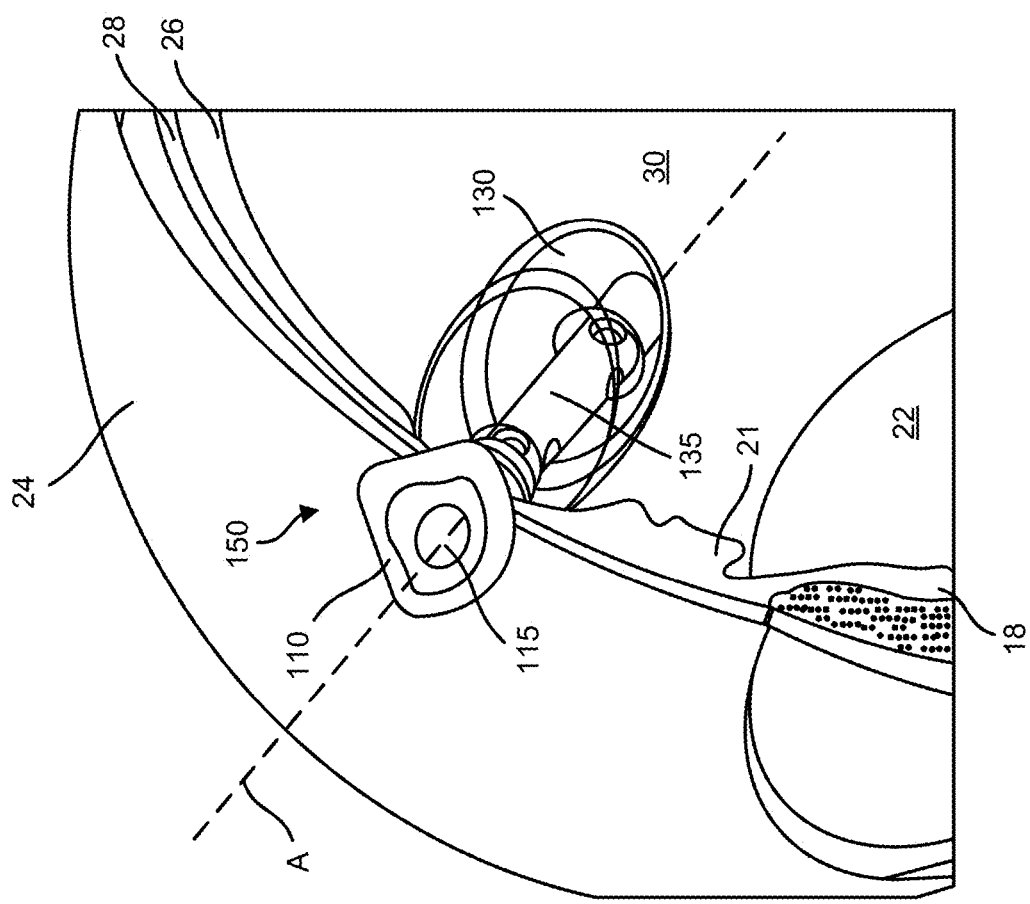
FIG. 13 is a partial, cross-sectional perspective view of an implementation of a flange element on a therapeutic device.
Figure 14:
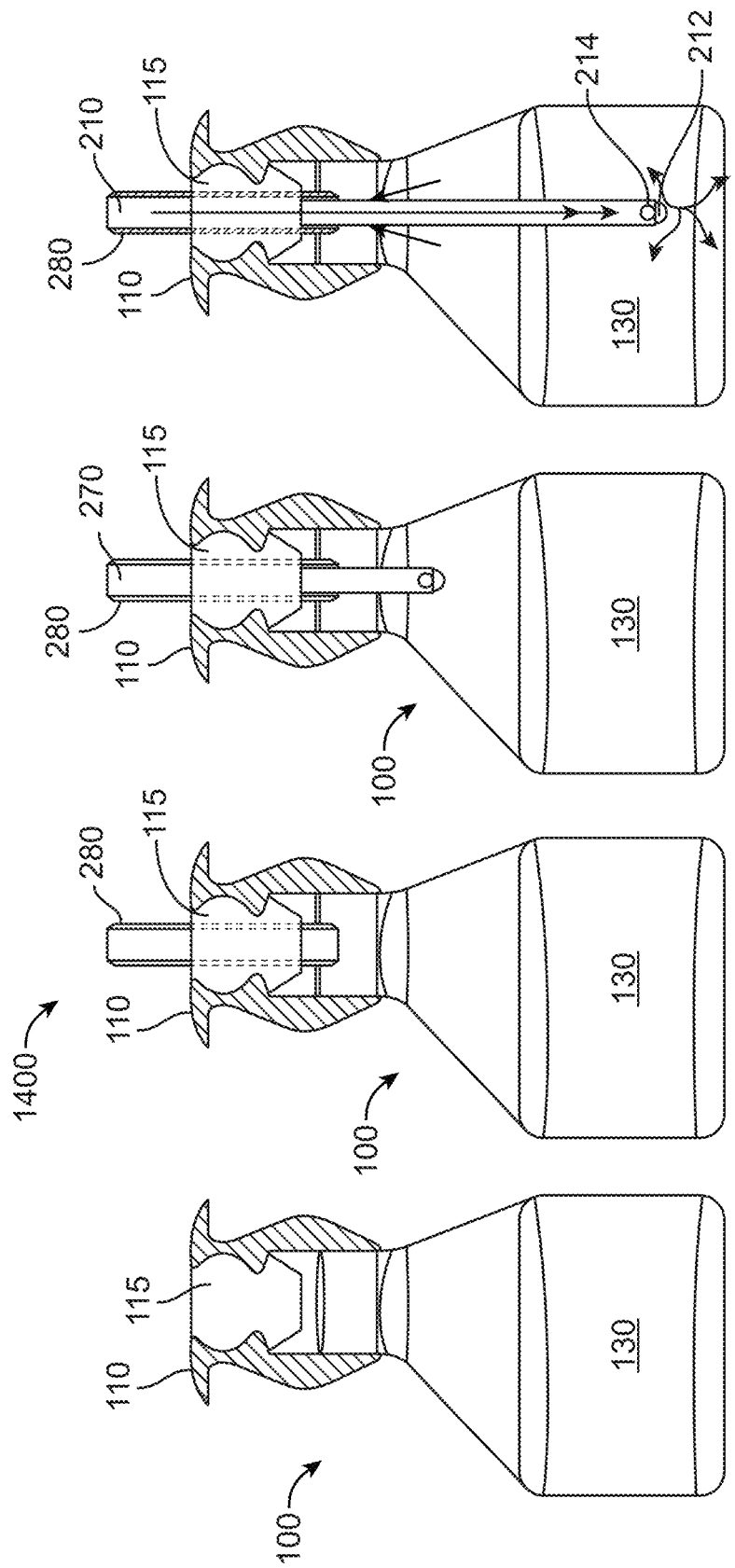
FIGS. 14A-14D illustrate sequential views of a generic tool inserted to fill a therapeutic device.

As discussed above, the device can include a proximal retention structure 105 having a smooth protrusion or flange element 110 configured to remain generally external to the eye to aid in retention of the device 100 when the remainder of the device 100 is implanted intraocularly. In some implementations, the flange element 110 can be designed to provide an identifiable orientation of the device 100 for implanting in the eye such that the direction of expansion of an eccentrically expanding reservoir 130 is predictable and according to a desired orientation. The reservoir 130 once implanted within the vitreous 30 may not be directly visualized. Thus, an orientation indicator 150 on a portion of the device 100, such as the flange element 110, that can be visualized from outside the eye allows a user to know the expansion of the reservoir 130 will be in the correct plane. For example, FIG. 9 illustrates an orientation indicator 150 that is a dot or other visual indicator on an upper surface of the flange element 110. FIG. 13 illustrates an orientation indicator 150 that is a shape of the flange element 110 that indicates the orientation of the eccentric volume of the reservoir. For example, because the expandable reservoirs 130 can be designed to enlarge along a particular orientation relative to the longitudinal axis of the device and/or the insertion axis A, the relative orientation of that portion of the expandable reservoir 130 around the axis A can be critical in ensuring the device does not impinge on certain intraocular structures. In some implementations, the flange element 110 can incorporate a mark or other orientation indicator 150 on an upper surface 112 that is visible to a user to indicate orientation of reservoir filling. The orientation indicator 150 can be any of a variety of shapes, colors or combination of shapes and colors providing guidance regarding where the eccentric volume is located. Alternatively or additionally, the orientation indicator 150 can be the shape of the flange element 110 itself. For example, the flange element 110 can be shaped in such a way to provide directional guidance to a user for implantation of the device. The flange element 110 can have a variety of shapes such as an ovoid, elliptical, polygonal, triangular, or diamond shape or other shape such as an arrow having a side or angle or portion that indicates where the reservoir 130 is designed to have a greater expansion compared to another side of the reservoir 130. FIG. 13 illustrates a flange element 110 having a particular shape indicating orientation of the eccentric region of the reservoir 130. Upon filling, the orientation indicator 150 will indicate to a user the portion of the reservoir 130 that will enlarge away from one or more internal structures of the eye, such as the lens 22. It should be appreciated that the flange element 110 can be keyed or configured to couple with a fill device having keyed features that also provides visual feedback to the user regarding the orientation of the eccentric volume of the device prior to fill or refilling.

The penetrable element 115 may additionally or alternatively include a color or other indicator to improve guidance during injections. At least a portion of the material of the penetrable element 115 can be colored or a colored element added to an outer surface of the penetrable element 115. The color selected can vary, including, but not limited to black, white, red, blue, orange, yellow, green, purple, or other variants in between. The material of the penetrable element 115 can also be translucent such that it appears dark from above due to the reservoir chamber underneath it. The color of the material of the penetrable element 115 can also be made into a pattern, such as stripes or hatched appearance, or a shape, such as a circle or target. Generally, the color of the material of the penetrable element 115 is selected to provide heightened contrast relative to the remainder of the device as well as the tissues surrounding the device upon implantation.

The devices described herein can incorporate expanding reservoirs that are also symmetrically distributed in the expanded configuration. As previously shown in FIGS. 2 and 3, the reservoir 130 can enlarge from the insertion configuration to an expanded configuration such that the volume of the reservoir 130 is symmetrically distributed about the longitudinal axis of the device as well as the axis of insertion A. In another implementation, the devices described herein can have expanded configurations that are symmetrically distributed, but the overall shape of the device itself can be formed into a curvilinear or other shape that is not aligned with the axis of insertion A.

The treatment devices described herein can be designed for prolonged retention in the eye to deliver drug to the vitreous for an extended period of time. The way in which the treatment devices described herein are retained in the eye can vary. For example, in some implementations the treatment device can include a proximal retention structure having a flange element that is configured to reside extra-sclerally and work in concert with portions of the device residing trans- or sub-sclerally to affix the device to the eye and provide stability during use. Other implementations of the treatment devices described herein have no extra-scleral retention structure per se and rely upon suturing to the sclera to affix the device to the eye. For example, the device can be implanted trans- and/or sub-sclerally and a proximal region of the device sutured to the sclera to affix the device to the eye. In further implementations, the treatment devices described herein may have an extra-scleral retention structure providing fixation that is further enhanced by suturing. For example, the flange element of the retention structure can incorporate one or more anchor features to enhance fixation or stabilization of the device in the eye, including, but not limited to holes, indentations, or other features that provide a location for suturing of the device to the eye. Some additional retention and stabilization features for use with the treatment devices will be described in more detail below.

As described elsewhere herein the proximal aspects of the implants (sometimes referred to herein as the "upper region" or "trans-scleral region" or "neck") allow for re-charging of the implant depot/reservoir from outside the eye. For example, the arrangement of the retention structure, if present, relative to the eye tissue ensures the penetrable element is accessible from outside the eye such that techniques commonly employed for direct intravitreal injections of the eye can be used to refill and/or flush the reservoir of the implant. As will be described in more detail below, placement of the implants described herein can involve the temporary resection of the conjunctiva followed by creation of an incision of fixed length (e.g. 3.22 mm) in the pars plana region using a flat surgical blade. Implants such as those described herein can allow for persistent physical access such as via a needle-type accessory and can physically contact trans-scleral tissues including one or more of the sclera, scleral blood vessels, the choroid, and possibly adjacent retinal and/or ciliary body tissues. The insertion of the implant in the trans-scleral region can cause a physical interference between the implant and the tissues of the eye adjacent the implantation site that can disrupt the edges of the incision and prevent the tissues from returning to a more natural or relaxed state around the implant. Further, the choroid can be disturbed upon penetration of the trans-scleral and sub-scleral components of the implant at the time of surgical implantation, which can increase risk of acute delamination of the tissue layers and contribute to the risk of bleeding at the site of implantation at the time of surgery that can lead to vitreous hemorrhage. The devices described herein can incorporate features that although they may pass through the scleral interface with the choroid for proper implantation in the eye, the risk of delamination and vitreous hemorrhage is minimized while still providing sufficient fixation in the eye, and a resealing septum region to provide effective sealing following multiple needle penetrations over time for prolonged treatment with the device.

In some implementations, the major diameter of the trans-scleral region of the device (as well as any portion of the device passing through the sclera) is no greater than the length of the incision, and preferably smaller than the length of the incision, which can be between about 1 mm to about 5 mm. The dimensions of the treatment devices described herein generally avoid stretching of the incision during implantation and subsequent use. In some implementations, the minor diameter of the retention structure 105, which is primarily responsible for 'propping' open the tissue edges of the incision, can be minimized. Minimization of the trans-scleral regions of the device allows for the device to be inserted in a manner that does not enlarge the incision and allows for the tissue edges to be in a more relaxes state around the implant neck or upper end region and minimize disturbance to ocular wall tissue structures (e.g. choroid). In some implementations, the largest minor diameter of the trans-scleral region of the implant can be no greater than and preferably less than 3.3 mm, 3.2 mm, 3.1 mm, 3.0 mm, 2.9 mm, 2.8 mm, 2.7 mm, 2.6 mm, or 2.5 mm. In some implementations, the largest minor diameter of the trans-scleral region is between about 1.0 mm to about 2.6 mm.

The penetrable barrier of any of the treatment devices described herein can include those described in U.S. Publication No. 2014/0296800, and U.S. Provisional Application Ser. No. 62/318,582, filed Apr. 5, 2016, which are incorporated by reference herein. The penetrable barrier can incorporate one or more features providing enhanced retention of the penetrable barrier within the access port using any of a number of features as described therein. For example, the penetrable barrier can be shaped to mate with a corresponding region within the access port. The penetrable barrier can incorporate one or more features such as a skirt region configured to extend past the access port into the reservoir volume to further support retention. The device can include a cover to improve the integrity of the penetrable barrier and its sealing engagement with the access port. The access port can include an inner anchor feature such as a donut-shaped element configured to encircle at least a region of the penetrable barrier and/or a secondary penetrable barrier positioned above and/or below the primary penetrable barrier. The penetrable barriers described herein need not be a septum formed of a penetrable material. For example, any of the treatment devices described herein can incorporate a valve mechanism with or without a septum as the penetrable barrier. The valve can be configured to receive an elongate fill device through it, such as a blunt needle or elongate cannula, for filling of the reservoir with a drug. The valve can be configured to open upon application of a force in the distal direction by the fill device. The opening of the valve can permit the fill device to form a fluid tight engagement and allow fluid communication between a fluid container attached to the fill device and the reservoir of the treatment device. The valve and the fill device can be configured to seal during injection such that fluid enters the reservoir in a manner that prevents fluid from leaking between the valve/fill device interface. The configuration of the valve can vary, including, but not limited to a split septum, a check valve, a ball valve, a flap valve, a disc valve, a duckbill valve, or other valve configuration. In some implementations, the penetrable barrier can be a twist valve. The twist valve can include a tortuous path that prevents fluid from entering or exiting the device. The fill needle can include a sharp element for penetration of an outer septum material and a blunt obturator for insertion through the tortuous path. As the obturator is inserted through the tortuous path it straights the path until a distal tip of the fill needle is located within the reservoir such that material can be inserted/withdrawn from the reservoir. Upon removal of the fill needle from the path, the tortuosity of the path returns maintaining the fluid-tight seal.

Any of the device implementations described herein can incorporate one or more features that provide for fixation of the device in the eye in any combination. The features can include the proximal retention structure having a flange element configured to be positioned in a supra-scleral location when the treatment device is in use. The features can also include the relative shape of the upper end of the treatment device (i.e. proximal region and distal extension) to improve trans-scleral and/or sub-scleral fixation. The features can also include features that allow for suturing of the treatment device. These features can be used alone or in combination. For example, the treatment devices described herein can rely only upon suturing in place or suturing can be incorporated as an enhanced fixation feature. The treatment devices described herein need not rely upon suturing for fixation and can rely upon one or more features of the upper end of the treatment device to maintain the device in place. Thus, the features for fixation of the treatment device can be sub-scleral, intra-scleral, and or supra-scleral features.

It should be appreciated that the treatment devices described herein can be used in a variety of locations and implanted in a variety of ways. The implantation method and use of the treatment devices described herein can vary depending on the type of treatment device being implanted and the intended location and drug for treatment. As will be described in more detail below, the treatment devices described herein can be primed, implanted, filled, refilled, aspirated, and/or explanted using one or more devices. Where the treatment device is described as being primed prior to filling with therapeutic solution, the device may also be implanted without priming. For example, the device may be implanted "dry" and the air expelled from the device as the device is filled with therapeutic solution or passively dissolved after implantation. Similarly, where the treatment devices are described herein as being removed from the eye, they may also be left implanted indefinitely without delivering therapeutic material.

In one implementation of treatment device implantation, a sclerotomy is created according to conventional techniques. The sclerotomy can be created posterior to an insertion site of the treatment device through the sclera 24 or the sclerotomy can be created directly above the insertion site of the post through the sclera 24. The conjunctiva 16 can be dissected and retracted so as to expose an area of the sclera 24. An incision in the conjunctiva 16 can be made remote from the intended insertion site of the treatment device. A scleral incision or puncture can be formed. The scleral incision or puncture can be made with a delivery device tool or using a distal tip of the treatment device, as described above. In some implementations, the treatment device is implanted using sutureless surgical methods and devices. In other implementations, the treatment device can be positioned sub-sclerally such as under a scleral flap. The post can be inserted into the eye (such as within the vitreous or the anterior chamber, etc.) until at least one of the outlets is positioned within or near the target delivery site and, if a flange element is present, until the inner-facing surface of the flange element can abut an outer surface of the eye. An additional fixation element can be used such as a suture or other element if needed following implantation of the treatment device in the eye as described elsewhere herein. The treatment device can remain in position to deliver the one or more therapeutic agents to the eye for a period of time including, but not limited to 1, 2, 3, 4, 5, 10, 15, 20, 25 days or any number of days, months and year, up to at least about 3 years. After the therapeutic agent has been delivered for the desired period of time, the treatment device can be refilled for further delivery or removed.

Generally, the implementations of the treatment devices described herein contain drug solutions, drug suspensions and/or drug matrices. The treatment devices described herein can also contain therapeutic agents formulated as one or more solid drug core or pellets formulated to deliver the one or more therapeutic agents at therapeutically effective amounts for an extended period of time. The period of time over which the treatment device delivers therapeutically effective amounts can vary. In some implementations, the treatment device is implanted to provide a therapy over the effective life of the device such that refill of the device is not necessary.

FIGS. 14A-14D show a generalized tool 1400 designed to prime, fill and/or refill the treatment devices described herein. The tool 1400 can include a trocar introducer cannula or outer sheath 280 having an internal lumen through which an internal fill cannula or needle 270 can extend. The sheath 280 can extend through the penetrable element 115 in the proximal region of the device 100 until the distal end of the sheath 280 enters a proximal end region of the reservoir 130 (see FIG. 14B) and/or the proximal end of the central core element 135, if present. A region of the tool 1400 can have a stop (not shown) to prevent the distal tip 212 from extending too far into the reservoir 130. The needle 270 can extend through the internal lumen of the sheath 280 and into at least the proximal end region of the reservoir 130 (see FIG. 14C). The needle 270 can extend further into the reservoir 130 towards a distal end region of the reservoir 130. The overall length of the needle 270 can be selected based on the treatment device with which it will be used such that the needle 270 can extend towards a distal end region of the reservoir 130 or the central core element 135, if present. Or if the device includes a flow director 140, the needle 270 can have a length configured to extend through at least a region of the flow director 140. The needle 270 can include a distal tip 212 having an opening 214 through which material may flow out of the needle 270 (see FIG. 14D). The distal tip 212 can be sharp or can be blunted. The flow of material through the needle 270 and out the opening 214 near the distal tip 212 allows for filling of the reservoir 130 in a bottom-up manner. A distal end region of the sheath 280 can be configured to receive pre-existing material from the reservoir 130 such that it can be flushed out from the reservoir 130 upon filling with new material through the needle 270. This in combination with a flow director 140 can increase refill efficiency.

The tool 1400 can incorporate one or more features of other refill devices described, for example, in U.S. Pat. Nos. 8,399,006; 8,623,395; U.S. Publication No. 2013/0324918; and U.S. Publication No. 2013/0165860, which are each incorporated in their entireties herein. It should be understood that depending on the overall length of the access region as well as the penetrable barrier installed in the access region of the treatment device, the fill cannula or needle 270 may have any of a variety of lengths and/or reinforcement structures. It should also be appreciated that where the needle and sheath are described as being movable with respect to one another that they can also be in a fixed configuration. As described elsewhere herein, the exchange of fluids can incorporate aspiration as well as positive displacement exchange.

The reservoir 130 can be filled and expanded following implantation and seating of the device. However, it should be appreciated that the reservoir 130 can be filled during or after final seating the treatment device 100 fully within the incision as will be described in more detail below. In some implementations, the fill needle can be a 30 gauge needle that has a hub providing visual feedback via its fluid return path when the treatment device 100 has been filled. For example, the fill needle can include a transparent or translucent chamber for viewing return fluid. The fill needle can also include one or more return fluid path holes. The fill needle can be used to inject therapeutic fluid into the device 100 until the prime fluid is removed from the treatment device 100. The reservoir 130 expands as the device 100 is filled with fluid. The device 100 can be slightly overfilled to ensure maximum expansion. In some implementations, the fill needle can be the same as a prime needle used to prime and purge air from the treatment device as described above.

The fill needle can also be part of an insertion device used to hold and deliver the treatment device into position.

Figure 15:
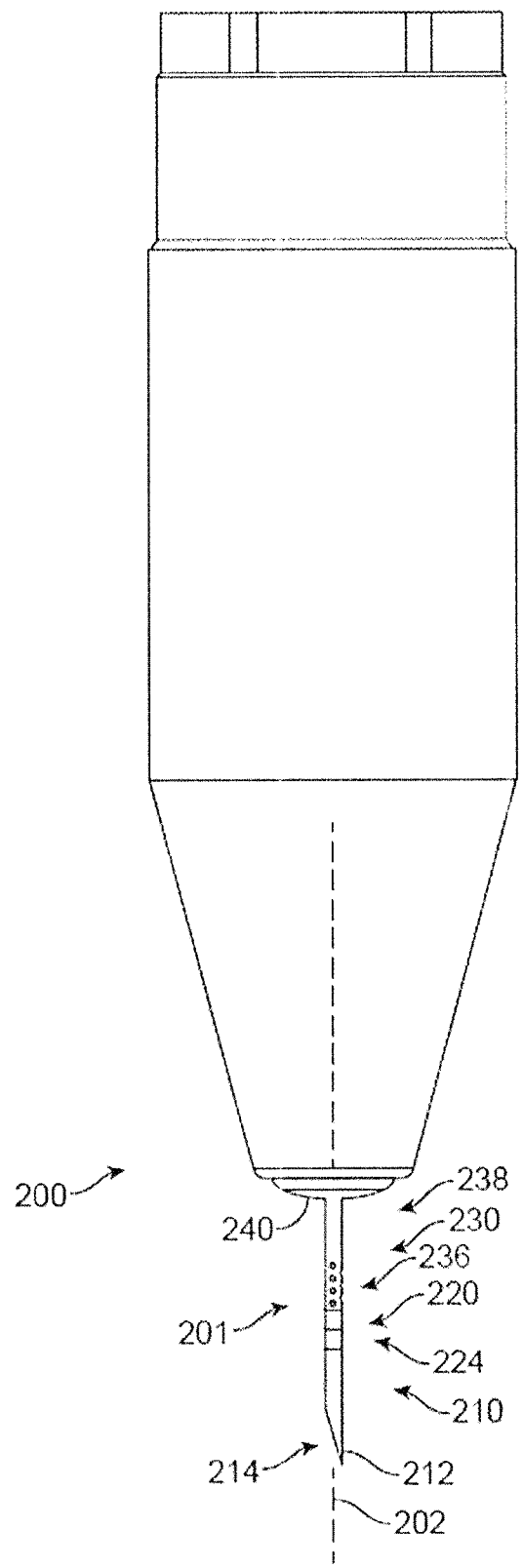
FIG. 15 is an implementation of an exchange needle apparatus for refilling of an implanted therapeutic device.

FIG. 15 is an implementation of an exchange needle apparatus 200 to exchange fluid of a device 100 to refill the device 100 while it is implanted in an eye. The apparatus 200 can be coupled to or include a syringe 300 having a container 310 (see FIG. 18C) to inject a therapeutic fluid into the reservoir 130 of the device 100. The apparatus 200 can include an elongate structure 201 that can be placed substantially within at least a portion of the device 100. The elongate structure 201 can include at least one opening 214 to place the therapeutic fluid in the reservoir 130 of the device 100 and a plurality of openings 236 to receive the fluid from the reservoir 130 of the implantable device 100.

Still with respect to FIG. 15, the elongate structure 201 can have a distal portion 210, an intermediate portion 220, and a proximal portion 230. The distal portion 210 can include a distal tip 212 configured to penetrate the penetrable element 115 of the implantable device 100. The at least one opening 214 to inject therapeutic fluid into the implantable device 100 can be found at or near the distal tip 212. The intermediate portion 220 can include a tapered section 224 to gradually increase a size of the channel formed in the penetrable element 115 when the elongate structure 201 is advanced through the penetrable element 115 so as to maintain integrity of and mitigate damage to the penetrable element 115. The tapered portion 224 can extend along axis 202 and can be without holes so as to decrease pressure to the penetrable element 115 that may otherwise occur near the edge of a hole. The proximal portion 230 can include the plurality of openings 236 to receive the fluid from the reservoir 130 of the implantable device 100. The elongate structure 201 can include a stop 240 to limit a depth of insertion of the elongate structure 201 into the reservoir 130 of the device 100. The stop 240 can be a deformable material to engage with the tissue during injections. The proximal portion 230 can include an extension 238 extending from the stop 240. The extension 238 can be without holes to inhibit leakage when the fluid is exchanged and the stop 240 engages the conjunctiva 16.

When coupled to the therapeutic device 100, the stop 240 can be positioned to engage the conjunctiva 16 and the elongate structure 201 can extend through the conjunctiva 16 and the penetrable element 115 into the device 100. The elongate structure 201 can be sized so as to place the distal tip 212 at a location within the device 100 when the surface of the stop 240 contacts the conjunctiva 16, for example. The distal tip 212 can be located on the elongate structure 201 so as to place the distal tip 212 at a location from the penetrable element 115 within the device 100 that is no more than a desired length, such as about ¾ of the length of the implantable device 100, and in some implementations no more than about half of the distance of the device 100. The extension 238 can extend substantially through the penetrable element 115, for example, at least about half-way through the penetrable element 115 so as to position the plurality of openings away from an external surface of the penetrable element 115 and to inhibit leakage.

FIG. 16 shows a detail view of the elongate structure 201 of the apparatus 200 of FIG. 15. The elongate structure 201 extends along axis 202 between the distal tip 212 and the stop 240. The distal portion 210 can include an extension 211 having a substantially constant cross-sectional size extending between the tip 212 to penetrate tissue and the intermediate portion 220. As described elsewhere herein, the elongate structure 201 can include an internal fill cannula or needle 270 and an outer sheath 280. The needle 270 can extend through an internal lumen of the sheath 280. The needle 270 can include a distal tip 212 having at least one opening 214 through which material injected through the lumen of the needle 270 may flow out the opening 214. The distal tip 212 can be sharp or blunted. The sheath 280 can be configured to receive preexisting material from the reservoir 130 such that it can be flushed out from the reservoir 130 upon filling with new material through the needle 270. Thus, the sheath 280 can include at least one opening into its lumen. The opening can be formed at a distal end of the sheath 280 formed between the outer surface of the needle 270 and the inner surface of the sheath 280. Alternatively, or in additionally, the opening can include a plurality of openings through a wall of the sheath 280 as described in more detail below.

Still with respect to FIG. 16, the extension 211 can include a portion of the needle 270 extending from the stop 240 to the tip 212 of the needle 270. The tip 212 can be configured to penetrate tissue, such as the tip of the needle to penetrate conjunctival tissue. The tip 212 and the opening 214 can be located a distance 204 from the stop 240 and the plurality of openings 236 to provide efficient exchange of the fluid within the reservoir 130 of the implanted device 100. In some implementations, the opening 214 is placed at a distance from the stop 240 greater than the plurality of openings 236 such that the opening 214 is located distal to the plurality of openings 236. This relative position between the opening 214 and the plurality of openings 236 can inhibit mixing of the injected therapeutic fluid moving into the reservoir 130 through opening 214 with the fluid within the implanted device 100 moving out of the reservoir 130 through openings 236. The opening 214 can be separated from the plurality of openings 236 by a distance 208, such that the opening 214 can be located below the plurality of openings 236 when the therapeutic fluid is injected.

The therapeutic fluid may have a density greater than the fluid of the implanted device and opening 214 can be placed below the plurality of openings 236 when the therapeutic fluid is injected to inhibit mixing of the fluids (i.e. the fluid moving in from the fluid moving out). The axis 100A of the implantable device 100 and the corresponding axis of the reservoir 130 can be oriented away from horizontal, such that porous structure 120 may be located below the penetrable element 115 when the therapeutic fluid is injected. The axis 202 can be oriented away from horizontal such that opening 214 can be placed below the plurality of openings 236. The therapeutic fluid having the greater density can flow toward the distal end of the therapeutic device and the displaced fluid from the implantable device having the lesser density can be received by the plurality of openings 236 located above the opening 214. It should be appreciated that inner needle 270 can be movable relative to the outer sheath 280 or the two components can be in a fixed configuration relative to one another.

Examples of therapeutic agents and corresponding formulations and fluids that may have a density greater than the density of the fluid within the chamber of the implanted device are listed in Table 1 of U.S. application Ser. No. 14/937,784, published as U.S. 2016/0128867, which is incorporated herein in its entirety. For example, one or more of the therapeutic agent or a stabilizer can increase the density of the therapeutic fluid. In many embodiments the therapeutic fluid having the greater density comprises a stabilizer, such as trehalose, and the therapeutic agent such as a protein comprising an antibody fragment. Alternatively or in combination, the therapeutic formulation can include an amount of therapeutic agent sufficient to provide a density greater than the fluid of the implanted device. The difference in density can be within a range from about 1% to about 10% and can depend on the density of the fluid within the reservoir chamber of the therapeutic device and density of the therapeutic fluid placed in the reservoir chamber with the exchange apparatus. The density of the therapeutic fluid may correspond to a density of the therapeutic agent and a density of the stabilizer (when present). In many embodiments, the density of the fluid of the reservoir chamber may correspond to a density of phosphate buffered saline, or plasma, or an amount of therapeutic fluid remaining in the reservoir from a prior exchange, or combinations thereof, for example. As described elsewhere herein, differences in fluid density as a result of temperature differences between the exchanged fluids can improve bottom-up filling efficiency. As mentioned above, implant orientation and/or tilt angle between the implant and the exchange needle during refilling can improve refill efficiency where there is a solution density different between the fluid being injected and the contents of the implant. Aspiration can be incorporated to aid in the efficiency of the exchange as well.

When injected into a device implanted within the patient, the distance 204 may correspond to no more than approximately the length of the device 140. The distance 204 may be substantially the length of the reservoir 130 (or the central core 135, if present) so as to place the distal tip 212 near, but not touching the porous structure 120, and the elongate structure 201 of the exchange apparatus 200 can be aligned with an elongate axis 100A of the implantable device 100. In many embodiments, the distance 204 may correspond to no more than about half the distance of the reservoir chamber (or the length of the central core 135, if present) such that the elongate structure 201 can be readily aligned with the implantable device. Work in relation to embodiments suggests than a distance providing a tolerance for angular alignment error of the axis 100A with the axis 202 can facilitate exchange and improve efficiency of the exchange. The distance 204 from stop 240 to tip 212 can be no more than about half of the axial distance of the implantable device can facilitate alignment during injection.

The intermediate portion 220 can include an extension 222 extending between tapered portion 224 and the distal portion 210. The extension 222 can have a cross-sectional size that is smaller than the tapered portion 224. The extension 222 can have a smooth outer surface to penetrate tissue. The tapered portion 224 can have a smother outer surface to penetrate tissue and the penetrable barrier. The outer surface of the tapered portion 224 can extend at an angle of inclination relative to the axis, and the tapered portion 224 can include a conic section having an angle with the axis such that the outer surface extends at the angle of inclination relative the axis. The angle of inclination of the tapered portion 224 can be no more than about 25 degrees, for example. The angle of inclination can be about 1 degree, about 2 degrees, about 5 degrees, about 10 degrees, about 15 degrees, about 20 degrees, or about 25 degrees, for example. The extension portion 216 can have a first cross-sectional dimension, and the portion having the plurality of openings 236 can have a second cross sectional dimension greater than the first dimension, such that tapered portion 224 having the angle of inclination extends therebetween to connect the extension portion 216 with the portion having the plurality of openings 236.

Still with respect to FIG. 16, the proximal portion 230 can include the plurality of openings 236 spaced apart along the axis 202 and distributed circumferentially around the proximal portion to receive fluid from a plurality of circumferential and axial locations when the stop 240 engages the conjunctiva 16 to place the plurality of openings within the reservoir chamber. At least one opening 237 of the plurality of openings 236 can be separated from the stop 240 with a distance 206 corresponding substantially to the thickness of the penetrable barrier 184, such that the at least one opening 237 of the plurality of openings 236 can be placed near the inner surface of the penetrable element 115 to receive fluid contacting the inner surface of the penetrable element 115. In some implementations, the thickness of the penetrable element 115 is within a range from about 0.25 to about 2 mm, for example within a range from about 0.5 to about 1.5 mm, such that the thickness of the penetrable element 115 is substantially greater than a thickness of the conjunctiva which can be approximately 100 µm. The distance 206 corresponding substantially to the thickness of the penetrable element 115 can correspond substantially to the thickness of the penetrable element 115 and the epithelium of the patient.

As mentioned, the outer sheath 280 can be configured to extend over at least a portion of the needle 270. The sheath 280 can extend along the intermediate portion 220 and the proximal portion 230, and the needle 270 can extend through the sheath 280. The sheath 280 can include the plurality of openings 236 and provide one or more channels extending along needle 270 to pass the fluid of the implantable device through the septum.

Figure 17:
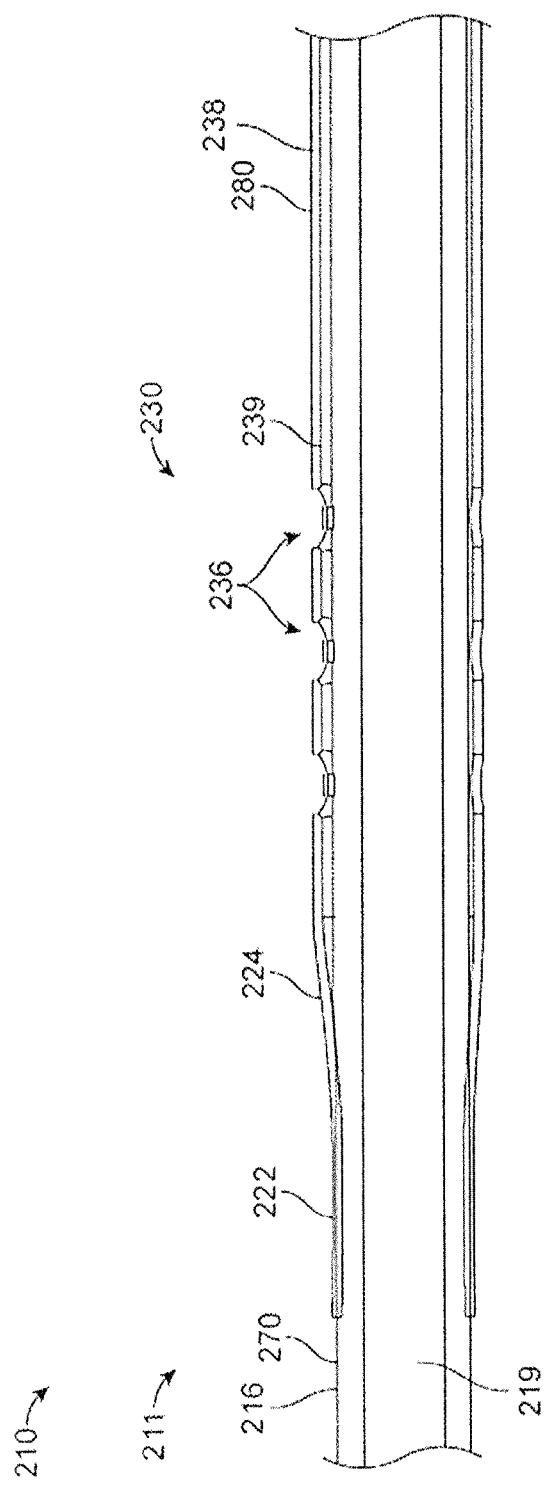
FIG. 17 is a cross-sectional view of an elongate structure showing a sheath extending over a needle.

FIG. 17 illustrates a cross-sectional view of an elongate structure 201 of the exchange apparatus 200 having the sheath 280 extending over the needle 270. The needle 270 can include a channel 219, for example a lumen. The channel 219 can be coupled on a proximal end to a syringe 300 or other container holding the therapeutic fluid to be injected into the device and extend to the distal opening 214 at a distal end region of the needle 270. The sheath 280 can include portions corresponding to the intermediate and proximal portions of the elongate structure 201. The extension 222 can include a distal portion of the sheath 280 having an inner surface sized to engage an outer surface of the needle 270. In some implementations, the diameter of extension 222 can have an inner diameter that approaches an outer diameter of the needle 270 to engage the needle 270 with at least one of pressure or friction. This minimizes distal-facing space between the needle 270 and the sheath 280 that can contribute to coring of the penetrable barrier 115 upon insertion of the elongate structure 201 into the device 100. The tapered portion 224 can include an intermediate portion of sheath 280, in which the sheath 280 has a tapered surface to penetrate the tissue and penetrable element 115. The proximal portion 230 can include a proximal portion of the sheath 280 having the plurality of openings 236 and the extension 238. As best shown in FIG. 17, a channel 239 can extend along an outer surface of the needle 270 to the plurality of openings 236. The channel 239 can extend proximally along extension portion 238 toward a collection chamber 250 (see FIG. 18C) to receive the fluid of the implantable device 100. The channel 239 can couple the plurality of openings 236 to the collection chamber 250 to receive the fluid of the implantable device 100 as will be described in more detail below.

Figure 18C:
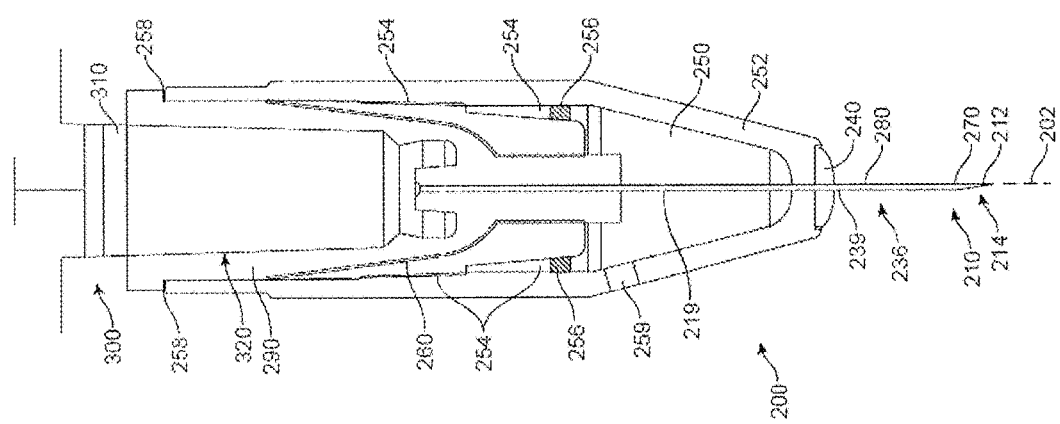

As mentioned, the exchange apparatus 200 can include a syringe 300 or other container 310 configured to hold fluid to be delivered to the reservoir 130. FIGS. 18A-18C show an implementation of an exchange apparatus 200 having a needle base assembly having a locking connector 290 to couple to a syringe 300. The connector 290 can be a locking connector having an extension 292 sized to fit in a channel of connector 320 of syringe 300, for example. The exchange apparatus 200 can include components of a standard locking needle assembly, for example a standard locking needle such as a Luer-Lok™ fitting or a pressure fit connector. Alternatively, the connector 290 may include a non-standard connector to limit access to the exchange apparatus 200. For example, the connector 290 can be a star connector or other connector, and connector 290 may include a lock and key mechanism. The lock and key mechanism can have a lock on the exchange apparatus 200 configured to receive a key of the injector, such that the lock of connector 290 can receive the key of connector 320 to couple the injector to the exchange apparatus 200 and permit injection from chamber 310 through opening 214. Alternatively, the syringe 300 may be affixed to exchange apparatus 200, and syringe 300 provided with a single dose of therapeutic agent.

The exchange apparatus 200 also includes a collection chamber 250 configured to receive fluid from the reservoir 130. The collection chamber 250 can be defined by a wall 252 configured to surround the needle 270 extending through the sheath 280. The wall 252 can extend a substantial distance from the stop 240 and can include at least one opening 258 that can vent to atmospheric pressure. As will be described in more detail below, an outlet channel 254 can extend from container 250 to the at least one vent opening 258 to atmospheric pressure.

Figure 18D:
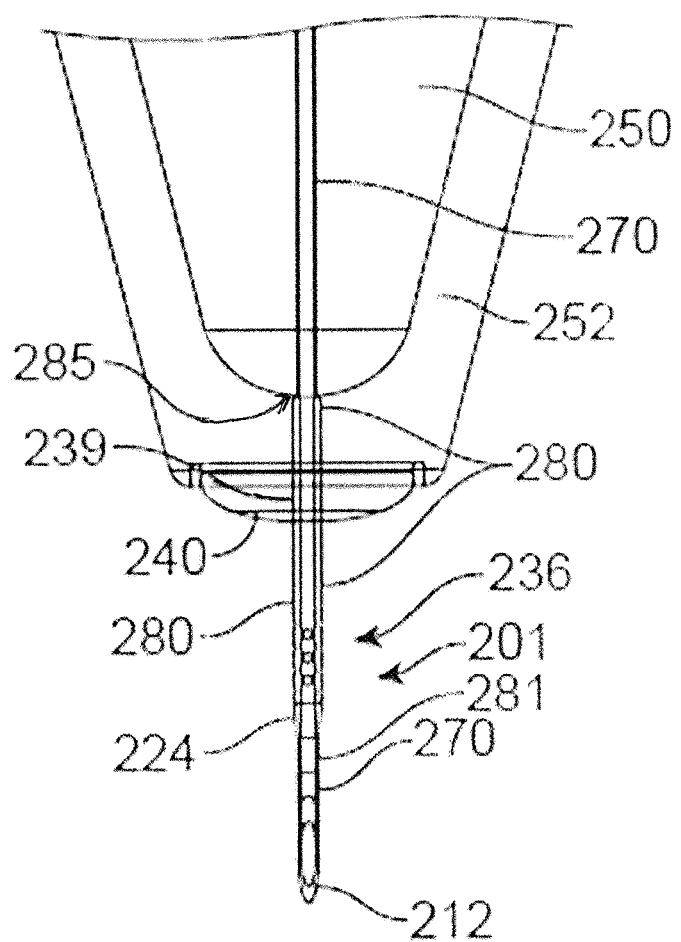
FIG. 18D is an implementation of an elongate structure and receiver container of the exchange apparatus of FIG. 18A.

FIG. 18D shows the elongate structure 201 and collection chamber 250 of the exchange apparatus 200 of FIGS. 18A-18C. The wall 252 can extend around a distal portion of collection chamber 250. The needle 270 and sheath 280 can extend through the wall of the collection chamber 250. The stop 240 can be located on a distal portion of wall 252 and can be formed of a soft material, for example, a soft elastomeric material such as silicone elastomer. The stop 240 can fit within a recess formed on the surface of wall 252, and the needle 270 and the sheath 280 can extend through the soft elastomer stop 240, for example. The sheath 280 can include the tapered portion 224 proximal to the plurality of openings 236. The needle 270 can extend from tip 212 through collection chamber 250 to the connector 290 (see FIGS. 18A-18D), for example. The sheath 280 can extend from a first end distal of the tapered portion 224 to a second end. The second end can include an opening 285 into collection chamber 250. The outflow path of the displaced fluid from the implantable device may extend through the plurality of openings 236 to channel 239, along channel 239 to opening 285, and through opening 285 and into collection chamber 250.

Figure 18E:
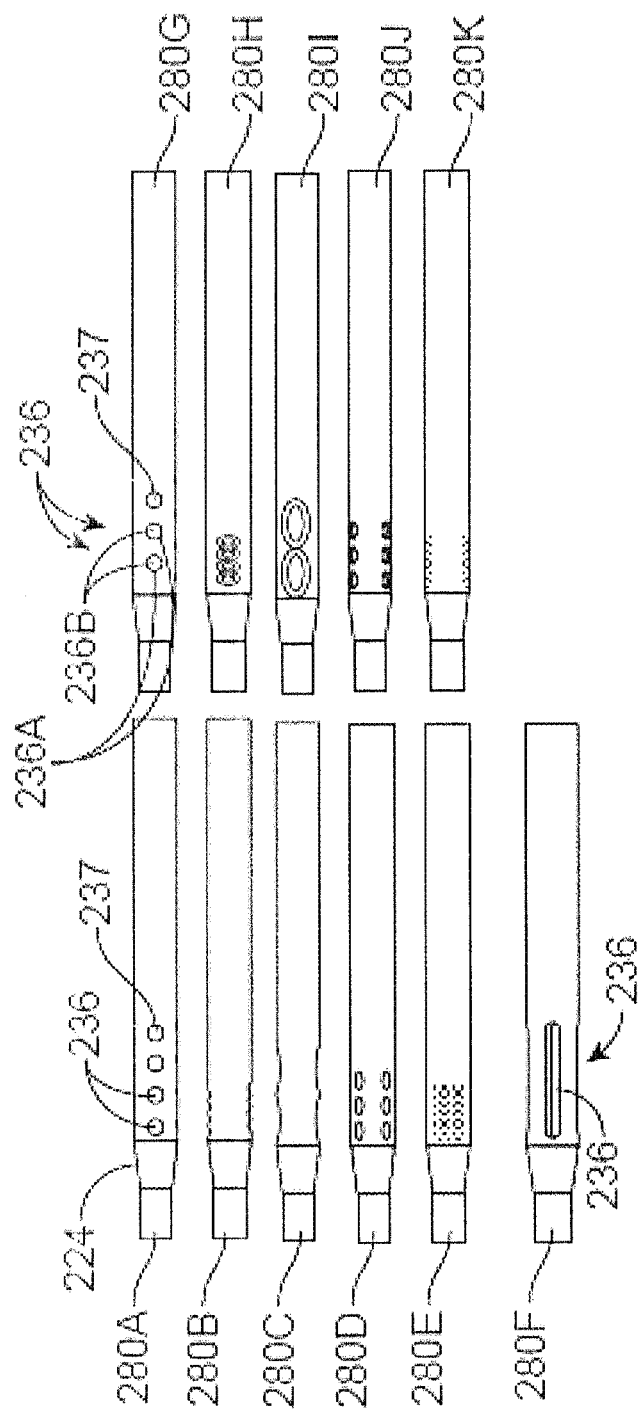
FIG. 18E illustrates various sheath configurations.

FIG. 18E shows various sheath configurations suitable for combination with the exchange apparatus of FIGS. 18A-18D. The sheath 280 can be configured in many ways (see 280A through 280K), and can have a wall thickness from about 0.0001 inches to about 0.01 inches, for example about 0.001 inches (1/1000 inch, 25 µm). The sheath 280 can include an inside diameter sized larger than the outside diameter of needle 270 so as to provide an annular channel 239 extending axially between the needle 270 and the sheath 280 from the plurality of openings 236 to the opening 285. The diameter of each of the openings 236 can be within a range from about 0.0001 inches to about 0.1 inches, for example within a range from about 0.001 inches to about 0.01 inches. The diameter of each of the plurality of openings 236 can be uniform or can vary in size as well as shape. The plurality of openings 236 can be one or more of many shapes and can be arranged in many ways. Each row can include from about 1 to about 20 holes, for example, and can be circular, oval, elliptical or other shapes, for example. The sheath 280 can include a sheath 280A having four rows of circular holes. Each of the holes can have a diameter of no more than about one half of the thickness of the outside diameter of the sheath 280, for example, and may be located circumferentially at 90 degrees to each other, for example. Each of the four rows may extend axially along the sheath 280. The rows can be spaced angularly at 90 degrees to each other, for example. The sheath 280 can include a sheath 280B having about two rows, each row comprising about four holes, each hole having a diameter of no more than about one eighth of the diameter of the outside diameter of the sheath 280. The two rows may be spaced apart circumferentially at 180 degrees, and the holes can include holes cross-drilled through both sides of the sheath 280, such that each hole has a corresponding hole on the other row on an opposite side of the sheath. The sheath 280 can include sheath 280C having about four cross-drilled holes, each hole having a diameter of no more than about three quarters of the diameter of the outside diameter of the sheath 280, for example. The holes can be pairs of holes, in which the holes of each pair have corresponding axial locations. The holes can be arranged in two rows spaced circumferentially at 180 degrees. The sheath 280 can include sheath 280D having at least about three rows of at least about 3 holes, each hole having a diameter of no more than about one quarter of the diameter of the outside diameter of the sheath 280. The rows can be spaced apart circumferentially at about 120 degrees, for example. The sheath 280 can include sheath 280E having at least about 40 holes, each hole having a diameter of no more than about one tenth of the diameter of the outside diameter of the sheath 280. The sheath 280 can include sheath 280F having slots. Each of the slots can be a narrow dimension across and a long dimension across. The long dimension can extend axially along the sheath 280 and may extend a distance greater than the narrow dimension across. The long dimension can extend a distance greater than the outside diameter of the sheath 280 where the slots are located, for example. The narrow dimension across each slot can be no more than about half of the outside diameter of the sheath, for example. The sheath 280 can be sheath 280G having staggered rows of holes. The plurality of openings 236 can include a first row and a second row of cross drilled holes 236A, in which the holes of the first row are paired with the holes of the second row at a common axial location for each pair. A third row of holes and a fourth row of holes can include cross drilled holes 236B located at 180 degrees to each other and 90 degrees to the first row and the second row. The axial locations of the third and fourth rows of holes can be staggered from the first and second rows of holes, such that the axial locations of the holes 236A of the first row and second row correspond to axial locations away from the holes 236B of the first row and the second row, for example. The sheath 280 can include sheath 280H having oval holes having a long dimension and a short dimension, with the long dimension extending transverse to the axis of the sheath 280 and the short dimension extending along the axis of the sheath 280. The oval holes can be spaced apart and located in rows extending along the axis of the sheath as described herein, for example. The sheath 280 can include sheath 280I having elongate oval holes having the long axis of the oval extending along the axis of the sheath and the narrow dimension of the oval extending transverse to the long axis of the sheath, for example. The sheath 280 can include sheath 280J having at least about three rows of at least about 3 oval holes, each oval hole having a maximum dimension across of no more than about one quarter of the diameter of the outside diameter of the sheath 280. The rows can be spaced apart circumferentially at about 120 degrees as described herein, for example. The sheath 280 can include sheath 280K having at least about 40 holes, each hole having a diameter of no more than about one tenth of the diameter of the outside diameter of the sheath 280. The holes can be located on opposite sides of the sheath 280, and may comprise cross drilled holes, for example.

The arrangement of the opening 214 from the inner needle 270 can vary as well. For example, the opening 214 can be configured to change direction of flow from the needle 270 into the reservoir 130 to impact refill efficiency. The opening 214 can include one or more side openings located near the distal tip 212 of the needle 270 similar such as that shown in FIG. 14C-14D. The openings 236 in the sheath 280, the openings 214 in the needle 270, the density/viscosity of the therapeutic fluid being injected, the presence of one or more flow director type features within the device 100 can all impact the effective flow patterns within the device to improve exchange efficiency.

Again with respect to FIGS. 18A-18C, the collection chamber 250 of the exchange needle apparatus 200 can have a volume (e.g., no more than about 200 uL, or no more than about 150 uL, or no more than about 100 uL, or no more than about 50 uL) and a porous structure 256 located within at least a region of the collection chamber 250 along the vent path. The porous structure 256 can be formed of a material having a low resistance to air and other gasses while substantially inhibiting flow of a liquid, such as the liquid from the device 100. The material of the porous structure 256 can be a hydrophobic membrane, a fabric, a porous fabric, a semipermeable membrane, an air permeable material, a moisture vapor transfer waterproof fabric, a hydrophilic porous material, or a porous sintered material. The porous structure 256 can have a low resistance to gas flow and a higher resistance to liquid. The liquid resistance is also greater than the liquid resistance through the porous structure (i.e. RCE) of the device 100. Thus, if additional volume of therapeutic fluid is injected once the exchanged liquid contacts the porous structure 256, a bolus can be released through the porous structure device into the eye. This allows for a controlled bolus to be driven into the eye (if desired) following the initial fill or exchange of liquids.

A device having a pliable, expandable reservoir wall is directly impacted by forces of intraocular pressure (TOP) once implanted. For example, the eye can be viewed as a closed system in equilibrium that has an internal pressure (intraocular pressure "TOP") that is greater than atmospheric pressure. An unobstructed vent in an exchange apparatus creates a pathway from inside the eye (higher pressure) to the atmosphere (lower pressure) upon penetration of the closed system, for example, by injecting therapeutic into the reservoir positioned within the vitreous. The higher pressure of TOP presses against the pliable reservoir wall positioned within the vitreous due to this unobstructed vent to the atmosphere thereby urging the wall to collapse inward. Thus, during filling of the device, TOP can impact fill efficiency and overall payload.

FIGS. 19A-19C illustrate fluid exchange of an implanted device 100 having an expandable reservoir 130 using an exchange apparatus 200 having an unrestricted vent 258 and no porous structure 256 within the collection chamber 250. The walls of the expandable reservoir 130 are pliable such that they can be moved by forces applied to their outer surface by TOP when a path to atmospheric pressure exists, such as via the unrestricted vent 258 of the exchange apparatus 200. Intraocular pressure can vary from patient to patient, but is generally within a range of 10 mmHg to about 21 mmHg, but can be higher than 21 mmHg in patients suffering from ocular hypertension. The IOP pressing against the walls of the implanted reservoir 130 urges liquid 505 in the reservoir 130 through the openings 236, out pathway 239, and into the empty chamber 250 immediately upon insertion of the elongate structure 201 through the penetrable barrier 115 into the reservoir 130 because an unrestricted path to atmospheric pressure is created (FIG. 19A). This causes the walls of the reservoir 130 to collapse slightly. Air 405 present within the empty collection chamber 250 escapes through vent opening 258 as the liquid 505 is expelled and begins collecting in the chamber 250. Application of positive pressure through the lumen 219 of the needle 270 to inject the therapeutic solution into the reservoir 130 increases internal pressure within the reservoir 130 to above IOP. The forces against the inner surface of the reservoir wall overcome the forces of IOP against the outer surface of the reservoir wall thereby urging the walls of the reservoir 130 to enlarge outward as the reservoir 130 fills with new solution (FIG. 19B). Air 405 in the chamber 250 continues to escape through vent opening 258 and liquid 505 from the reservoir 130 is further urged into the openings 236, out the pathway 239, and into the chamber 250. Once the application of positive pressure through the lumen 219 of the needle 270 to inject therapeutic into the reservoir 130 is terminated, the pressure within the reservoir 130 drops. The forces against the inner surface of the reservoir wall once again approach the forces of IOP against the outer surface of the reservoir wall, which allows the IOP to urge the walls of the reservoir 130 inward. Inward movement of the reservoir walls while the path to atmospheric pressure remains open (i.e. via the elongate structure 201) can force the newly added liquid into the openings 236, out the pathway 239, and into the chamber 250 at least until the elongate structure 201 is removed (FIG. 19C). Thus, unrestricted venting through vent opening 258 allows for the IOP to drive the newly added therapeutic out of the reservoir 130 into the collection chamber 250 resulting in a loss in delivery payload.

To counteract the forces of IOP on the pliable, expandable reservoir wall 130, the chamber 250 can include a porous structure 256 rather than unrestricted venting (see FIGS. 20A-20C). The porous structure 256 has a resistance sufficient to counteract the forces of TOP once filling is complete and maintain the increased pressure within the reservoir 130 and thereby prevent loss of new solution due to partial collapse of the wall. As described above, a path to atmospheric pressure is created immediately upon insertion of the elongate structure 201 of the exchange needle apparatus 200 through the penetrable barrier 115 into the reservoir 130. The IOP pressing against the walls of the implanted reservoir 130 urges liquid 505 (i.e., a pre-existing fluid that is a liquid) in the reservoir 130 from the device 100 through the openings 236, into an outlet lumen 239 that is fluidly coupled to the collection chamber 250 (FIG. 20A). The walls of the reservoir 130 collapse slightly. The air 405 present within the empty collection chamber 250 escapes through vent opening 258 and the porous structure 256 as the liquid 505 begins collecting in the chamber 250 because the porous structure 256 has a low resistance to air. Application of positive pressure through the injection lumen 219 of the needle 270 to inject the therapeutic solution into the reservoir 130 increases internal pressure within the reservoir 130 to at or above IOP. The forces against the inner surface of the reservoir wall overcome the forces of IOP against the outer surface of the reservoir wall thereby urging the walls of the reservoir 130 to enlarge outward as the reservoir 130 fills with new solution (FIG. 20B). Air 405 in the collection chamber 250 continues to escape through the vent opening 258 and the porous structure 256 and liquid 505 from the reservoir 130 is further urged into the openings 236, out the pathway 239, and into the collection chamber 250. The increased pressure during injection continues to counteract the IOP forces against the outer surface of the reservoir wall, which keeps the reservoir expanded during filling. Once the preexisting liquid 505 has been exchanged with the newly injected therapeutic agent, all the air 405 (i.e. a pre-existing fluid that is not a liquid) in the collection chamber 250 has passed through the porous structure 256 and out a vent opening 258 of the apparatus and the collection chamber 250 is filled substantially with the newly injected therapeutic agent. The liquid 505 contacts and wets the porous structure 256 of the collection chamber 250. Once wetted, the porous structure 256 has a resistance to liquid flow that is sufficient to counteract the forces of intraocular pressure (TOP) on the outside surface of the pliable, expandable reservoir wall 130. The liquid resistance of the wetted porous structure 256 restricts the flow of the liquid 505 through the porous structure 256 and further venting is greatly reduced. The pressure inside the device is maintained at or higher than IOP and the reservoir wall stays expanded even when application of positive pressure through the lumen 219 of the needle 270 is discontinued. The retained increased pressure (i.e. at or higher than IOP) inside the reservoir 130 prevents IOP-driven collapse of the reservoir walls (FIG. 20C). Thus, the liquid resistance of the porous structure 256 prevents collapse of the reservoir wall 130 that would otherwise be caused by forces of TOP against the outside surface of the wall 130 thereby preventing the newly added solution in the reservoir from being driven out of the implant leading to payload loss. The resistance to liquid flow through the wetted porous structure 256 can be higher than the resistance to liquid flow through the porous structure 120 of the device. As such, if a user continues to inject therapeutic agent into the reservoir 130 through the inlet pathway, an amount of newly injected therapeutic agent can be passed through the porous structure 120 of the device 100 and into the eye. This can be advantageous for treatments in which a bolus delivery through the device is desirable.

The device for injecting a therapeutic agent into an ocular implant, the implant being at least partially implanted in an eye and providing at least a first resistance to outflow of therapeutic agent into the eye, can include an injection lumen 219, an outlet lumen 239, and a collection chamber 250. The injection lumen 219 is configured to provide a pathway for injecting the therapeutic agent into the reservoir 130 of the ocular implant. The outlet lumen 239 is configured to provide a pathway through which pre-existing fluid 505 in the ocular implant exits the ocular implant. The pre-existing fluid 505 in the ocular implant that is at least partially implanted in the eye is typically a liquid. The liquid can include fluids from the patient (e.g. vitreal fluid) as well as left over liquid from therapeutic formulation that was being delivered by the implant. The collection chamber 250 is fluidly coupled to the outlet lumen 239. The collection chamber 250 is configured to receive the pre-existing fluid 505 that exits the ocular implant via the outlet lumen 239. The collection chamber 250 provides a first fluid outflow resistance and a second fluid outflow resistance. The first fluid outflow resistance can be lower than the first resistance to outflow of the implant. The second fluid outflow resistance can be greater than a force imparted onto the implant by intraocular pressure (TOP) of the eye. Injection of therapeutic agent into the ocular implant via the injection lumen 219, for example, to refresh and refill the ocular implant with new therapeutic formulation, causes the pre-existing fluid 505 to exit the ocular implant and enter the collection chamber 250 via the outlet lumen 239 and causes a second pre-existing fluid 405 to displace from the collection chamber 250. The second pre-existing fluid 405 in the collection chamber can be a gas, such as air or air under vacuum. Upon displacement from the collection chamber 250 of substantially all of the second pre-existing fluid 405, the second fluid outflow resistance of the collection chamber 250 can cause a portion of the newly injected therapeutic agent to pass from the implant into the patient's eye upon injection of an additional amount of the therapeutic agent into the ocular implant. Thus, the relative resistances can allow for exchange of fluids as well as delivery of a bolus amount of the therapeutic agent with a single penetration of the implant. The device for refill is particularly useful where the implant is expandable from a first, collapsed configuration to a second, enlarged configuration, which would tend to collapse upon exposure to TOP when the vented injector is fluidly coupled to the reservoir's contents. A first porous structure 256 can be operatively coupled to the collection chamber 250 and provide the first fluid outflow resistance and the second fluid outflow resistance. The first porous structure 256 operatively coupled to the collection chamber 250 can have the first fluid outflow resistance to gas outflow and the second fluid outflow resistance to liquid outflow. The implant can include a second porous structure 120 that provides the first resistance to outflow. The first fluid outflow resistance of the first porous structure 256 of the collection chamber 250 can be less than the first resistance provided by the second porous structure 120 of the implant. The second fluid outflow resistance of the first porous structure 256 of the collection chamber 250 can be greater than the first resistance to outflow of the implant. The second pre-existing fluid can be displaced from the collection chamber 250 via a vent or a valve.

In some implementations, evacuation/filling of the reservoir 130 involves aspiration. The liquid 505 in the reservoir 130 can be evacuated by application of negative forces through pathway 239 such that liquid 505 is drawn out of the reservoir 130 up into chamber 250. Upon evacuation of the pre-existing liquid 505 from the reservoir 130, a positive pressure can be applied to fill the reservoir with new solution as described above. Alternatively, negative pressure can continue to be applied through pathway 239 such that new solution is drawn into the emptied reservoir 130. As the reservoir 130 fills with new solution, the forces against the inner surface of the reservoir wall due to fluid filling overcome the forces of TOP against the outer surface of the reservoir wall thereby urging the walls of the reservoir 130 to enlarge outward. The pressure within the reservoir is maintained and the walls stay expanded upon wetting of the porous structure 256 as described above.

The porous structure 256 can create a fixed upper limit that together with wall 252 of the chamber 250 defines the volume of the chamber 250. The volume of the chamber 250 can be sufficient to collect a maximum volume of liquid held by the device 100. The volume of the chamber 250 can also be smaller than the maximum volume of liquid held by the device 100 such that upon fluid exchange a controlled amount of bolus expression occurs through the porous structure 120 of the device 100. The porous structure 256 can be a relatively rigid structure such that upon contact with liquid 505 exiting the device 100, the porous structure 256 resists deformation maintaining a fixed volume of the chamber 250. This prevents the structure 256 from deflecting to allow additional liquid to enter the chamber 250 after filling that could lead to payload loss. The fixed chamber volume also allows for the controlled bolus to be delivered when used in conjunction with a fixed injection volume.

The geometry of the chamber 250 as well as the relative position of the porous structure 256 within the chamber 250 can vary. Generally, the geometry and relative position of the porous structure 256 (e.g. at the highest possible point within the chamber 250) are designed to provide better venting of gas from the chamber 250 and predictable liquid filling from the bottom-up. Generally, the geometry of collection chamber 250 can direct filling to ensure the porous structure 256 is wetted by the evacuated liquid only after substantially complete air evacuation and, in turn, consistent liquid volume occurs. This ensures there is a "shut off" after the appropriate volume of new solution is injected. Gravitational forces and/or capillary action can be leveraged to allow for even and predictable filling and to minimize trapping of gas, as will be described in more detail below.

In some implementations (as shown in FIGS. 20A-20C), the porous structure 256 encircles the needle 270 (or the longitudinal axis of the needle 270) concentrically and engages the inner-facing walls of the chamber 250. The porous structure 256 can thereby form a cap creating a fixed upper limit of the chamber 250 and together with wall 252 define the volume of the chamber 250. The porous structure 256 can also be a discrete structure positioned within a region of the chamber 250 as will be described in more detail below.

Figure 21:
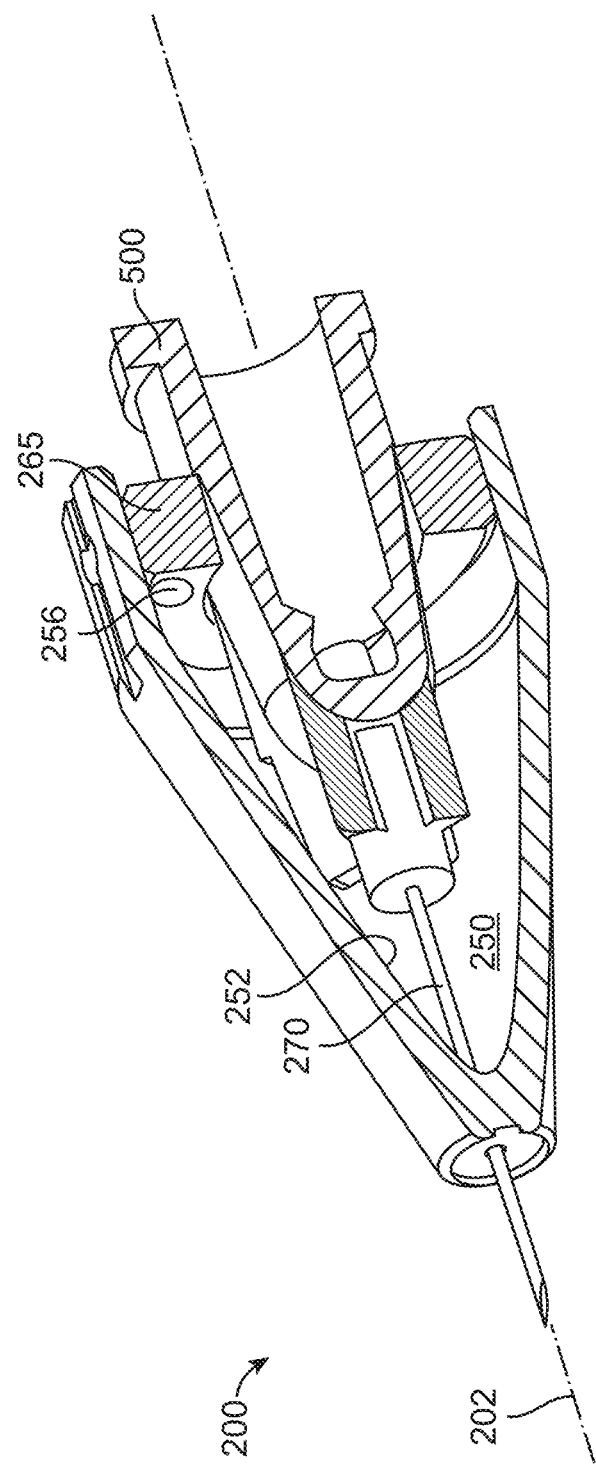
FIG. 21 illustrates an implementation of an exchange apparatus having a generally concentric collection chamber.

FIG. 21 is a cross-sectional perspective view of an implementation of an exchange apparatus 200 configured to be used with a syringe 300 or other container 310 configured to hold fluid to be delivered to the reservoir 130. The exchange apparatus 200 includes a collection chamber 250 configured to receive expelled fluid from the reservoir 130. The collection chamber 250 can be defined by a wall 252 configured to surround the needle 270 in a generally concentric manner. The wall 252 can flare out beyond a diameter of the syringe, for example, to collect larger volumes up to about 200 uL. An upper end region of the chamber 250 can be engaged with a spacer ring 265 having an inner diameter sized to encircle the needle hub assembly 500 and an outer diameter sized engage the wall 252. The spacer ring 265 forms a cap creating a fixed upper limit of the chamber 250 that together with wall 252 defines the volume of the chamber 250. The porous structure 256 can be installed within a region of the spacer ring 265 near the upper limit of the chamber 250. As previously described, the porous structure 256 can be a relatively rigid structure formed of a material having a low resistance to gas flow (e.g. air) and high resistance to liquid thereby substantially inhibiting flow of a liquid through it. The porous structure 256 is configured to balance the forces of TOP on the pliable reservoir walls of the device preventing collapse after filling thereby preventing payload loss.

Figure 22:
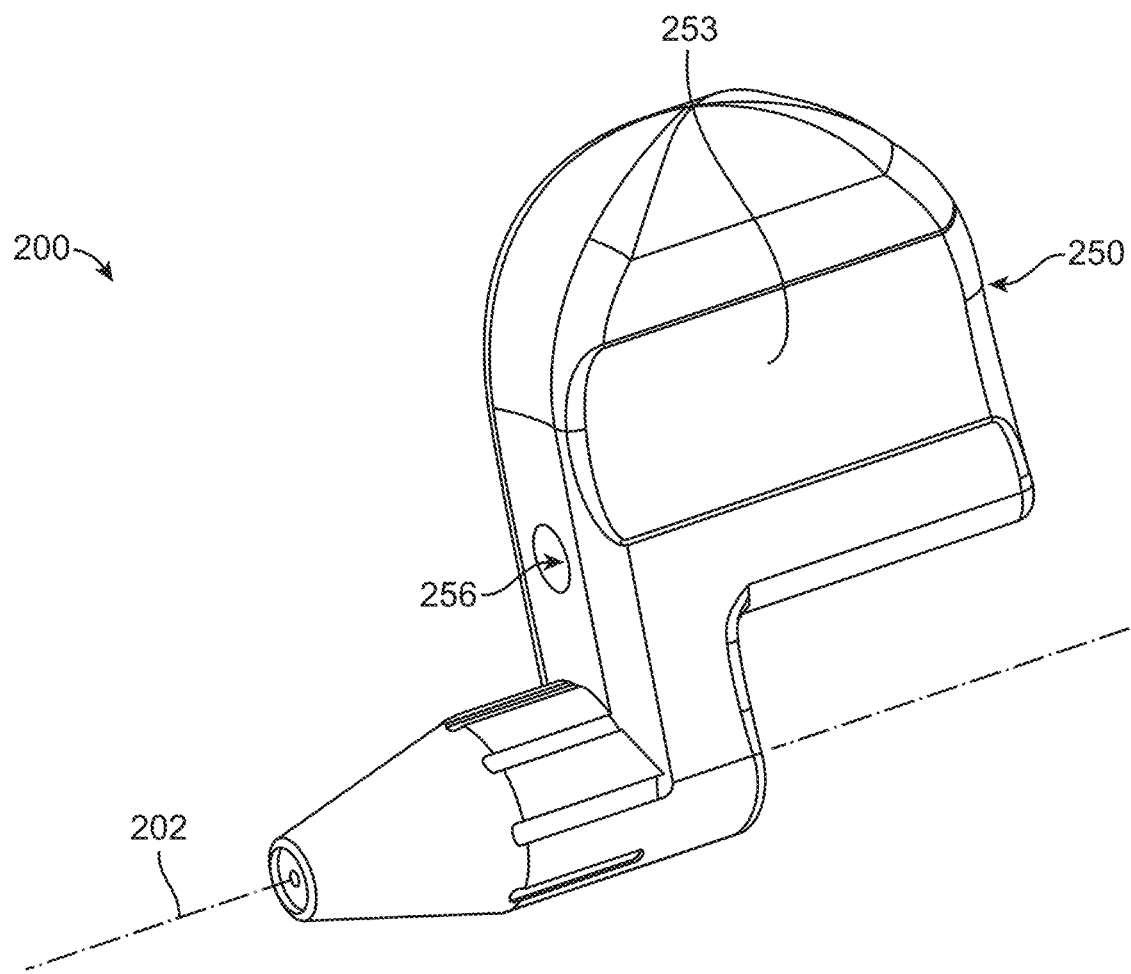
FIG. 22 illustrates an implementation of an exchange apparatus having an off-set collection chamber.

FIG. 22 shows a perspective view of another implementation of the exchange apparatus 200 having a collection chamber 250 that is offset relative to the axis 202 of the needle 270 (or the injection lumen of the needle 270). A concentrically positioned collection chamber 250 relative to the exchange needle 270 can impact a user's view of the device, especially where the chamber 250 has a high volume capacity (e.g. greater than 200 ul). The collection chamber 250 can be off-set from the axis 202 of the exchange needle 270 to mitigate issues with the chamber 250 obstructing a user's view of the device during penetration. Additionally, the body of the collection chamber 250 can incorporate one or more grip features 253 and/or be ergonomically shaped to assist in handling. As with other implementations, the collection chamber 250 can incorporate a porous structure 256, for example, near an upper limit of the collection chamber 250.

Figure 23:
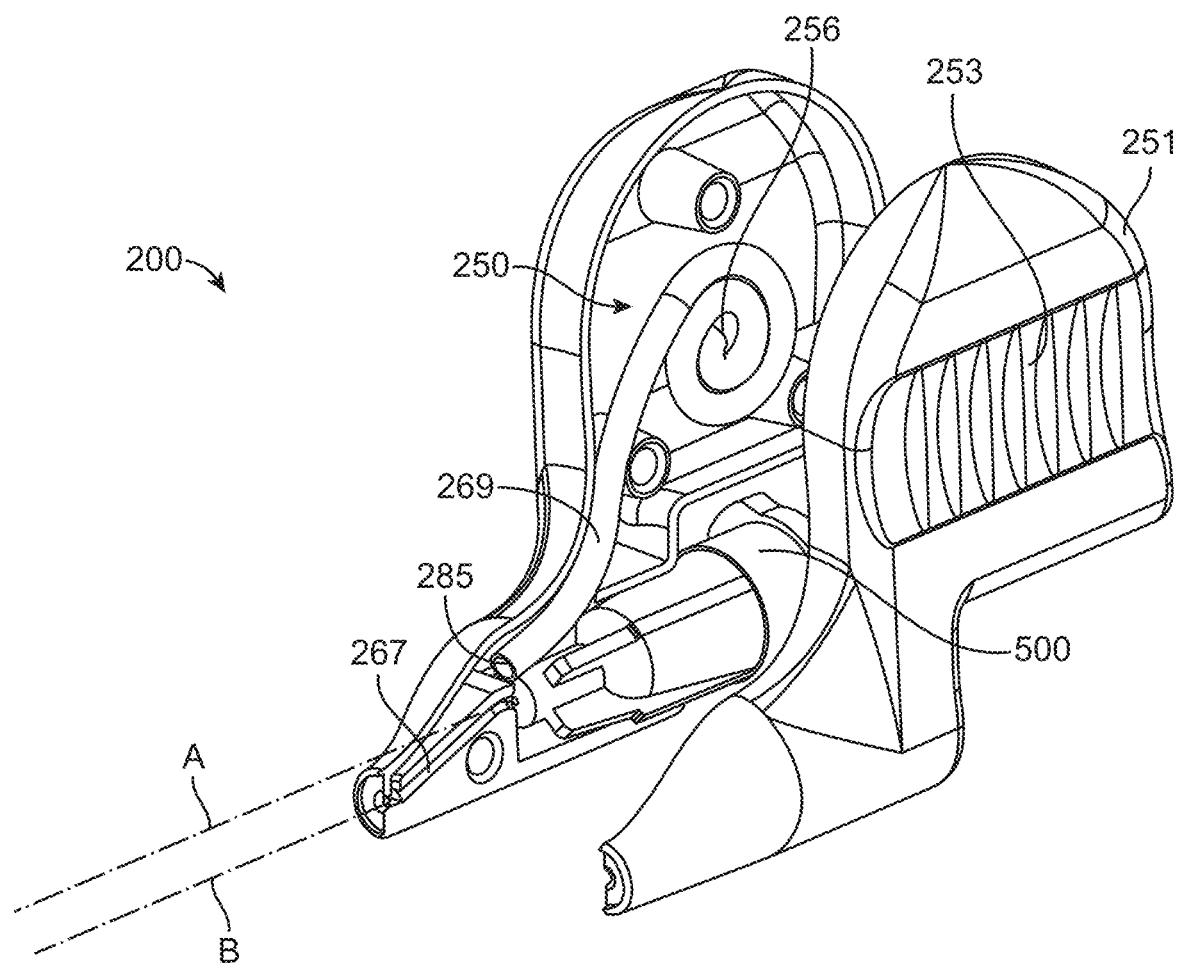
FIG. 23 illustrates an implementation of an exchange apparatus having an off-set collection chamber.

FIG. 23 shows a partially exploded view of another implementation of an exchange apparatus 200 having an offset collection chamber 250. A user's view of the needle tip (not shown) can be enhanced by modifying the shape of the needle cannula passage 267. For example, the needle cannula passage 267 can extend along a first axis A at a proximal end region and extend along a second axis B at a distal end region near the needle tip. As such, the needle cannula is routed from the first axis A to the second axis A such that is it routed away from the offset body 251 and the needle tip is no longer concentric to the hub assembly 500 or the syringe barrel connected to the hub assembly 500. Fluid expelled from the device into a return pathway is directed into the narrow collection chamber 250 through opening 285. In this implementation, the collection chamber 250 can be a tubular structure 269 having a lumen extending between the opening 285 into the tubular structure 269 and terminating at the porous element 256. Fluid expelled from the device through opening 285 enters the lumen of the tubular structure 269. The tubular structure 269 can have a relatively uniform inner diameter over its entire length. Inner diameter and length of the tubular structure 269 can vary depending on the overall volume capacity desired. The tubular structure 269 can be between 0.5 inches and 3.0 inches long and have an inner diameter between 0.125 inches and 0.5 inches. The tubular structure 269 can have an inner diameter such that capillary action can assist in pulling the exchanged liquid expelled from the reservoir 130 of the device 100 into and up through the lumen. Depending on the length the tubular structure 269 the end of the tubing away from the opening 285 into the lumen (i.e. within the body of the exchange apparatus) can be coiled. The number of coils varies with the length of the tubing. Thus, the coiled tube style collection chamber 250 can have a wider range in volume capacity while maintaining generally the same form factor. The coiled tube style collection chamber 250 provides for a uniform and controlled fill pattern, minimizing the risk of trapping air within the chamber 250 during exchange. Trapped air within the collection chamber 250 can impact the final fluid volume achieved within the reservoir of the device.

Figure 24B:
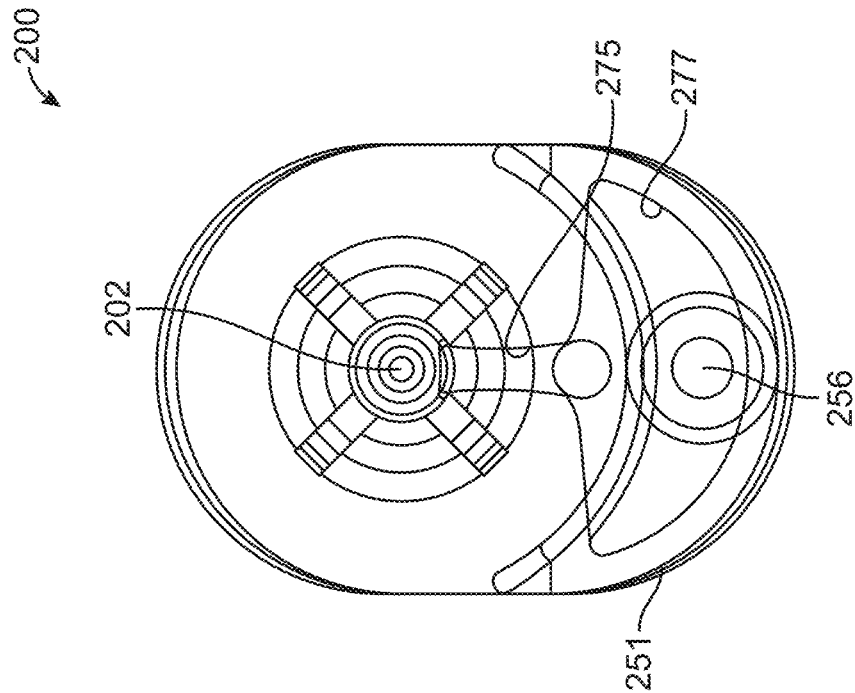
FIGS. 24A-24D illustrate various views of an implementation of an exchange apparatus having an off-set collection chamber.
Figure 24A:
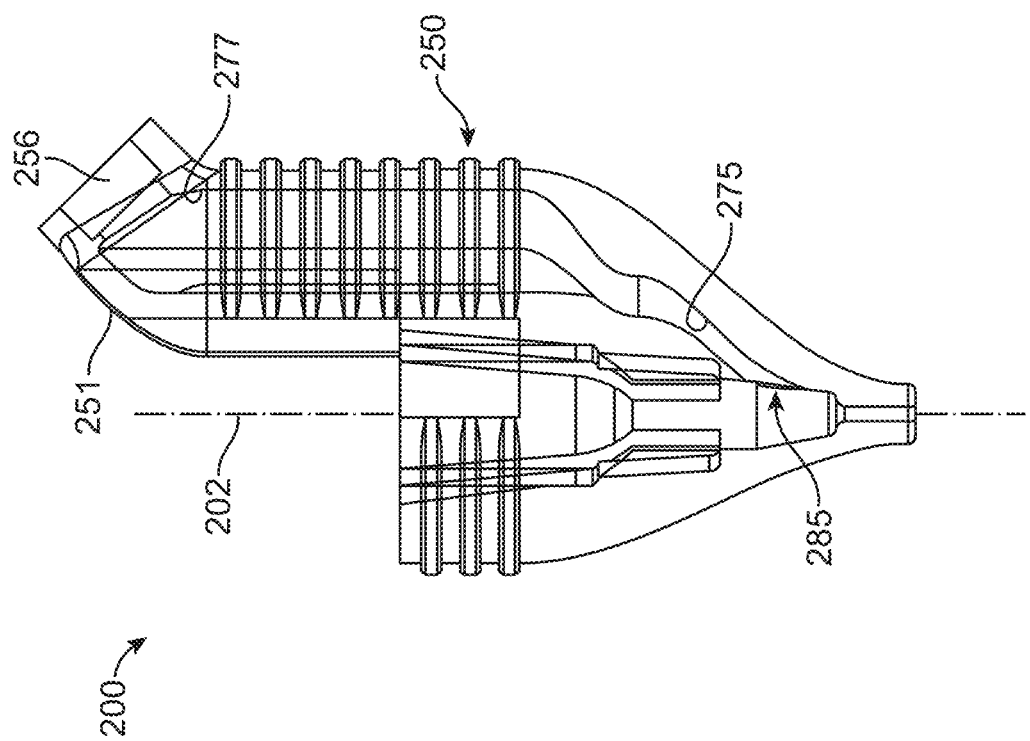
Figure 24D:
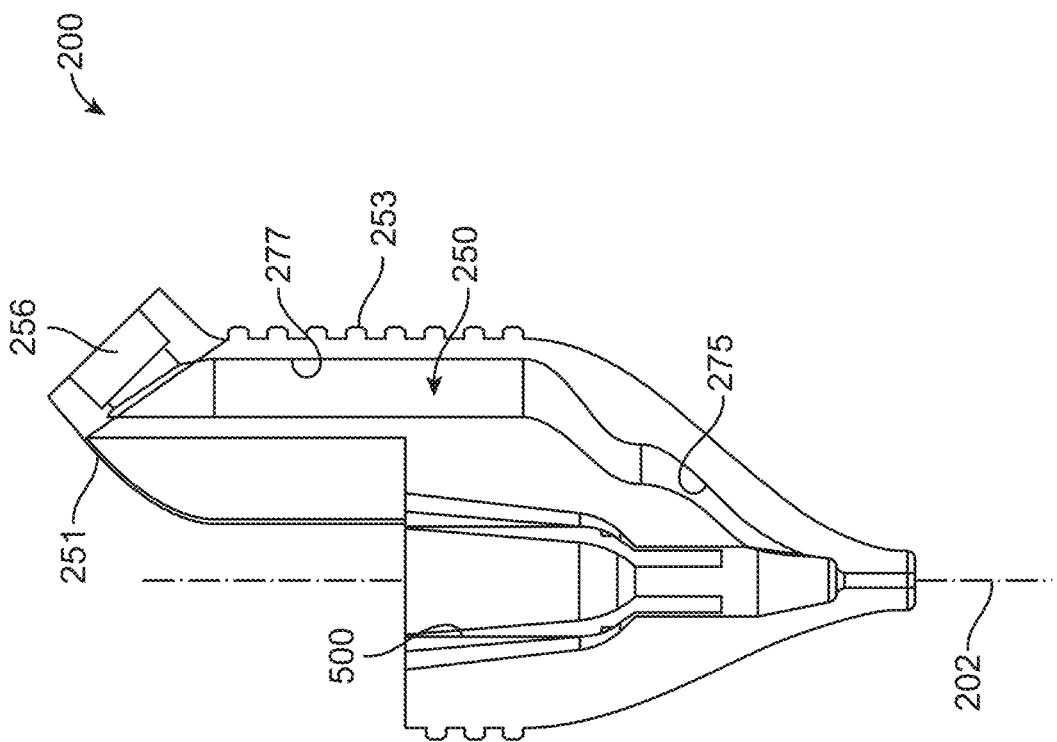
Figure 24C:
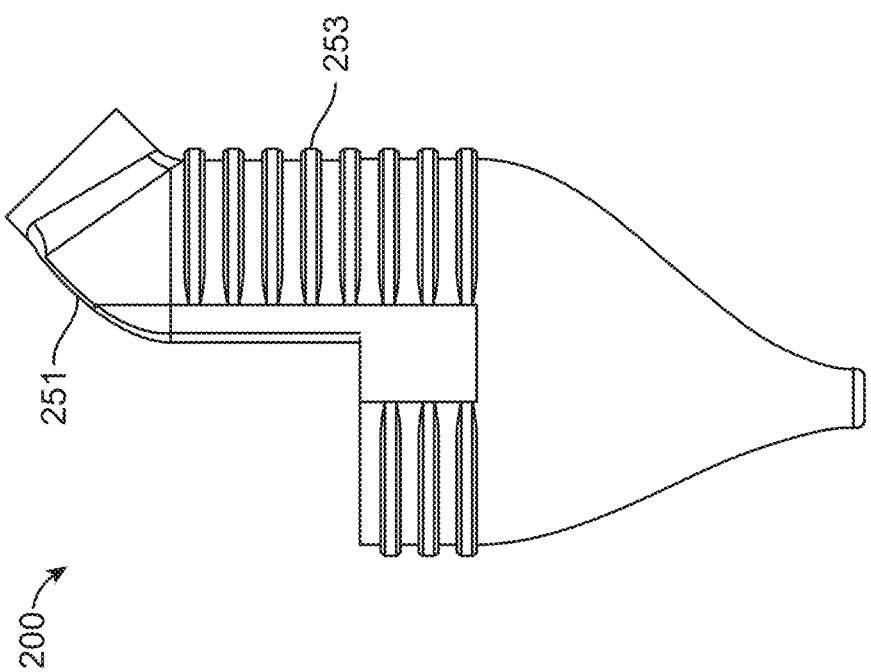

FIGS. 24A-24D illustrate another implementation of an exchange apparatus 200 having an off-set collection chamber 250. FIG. 24A is a transparent side view, FIG. 24B is a transparent top plan view, FIG. 24C is a side view, and FIG. 24D is a side cut-away view. The collection chamber 250 can have a narrow, tubular distal end region 275 that widens or enlarges proximally into a larger diameter proximal end region 277 of the collection chamber 250. The narrow distal end region 275 can be generally tubular for at least a length. Fluid expelled from the reservoir 130 of the device 100 enters the distal end region 275 via the opening 285. The fluid entering the distal end region 275 of the collection chamber 250 through the opening 285 is funneled through the collection chamber 250 towards the porous element 256 mounted at the upper or proximal end of the collection chamber 250. The porous structure 256 can be mounted according to a variety of configurations as described elsewhere herein. As described elsewhere herein, the porous structure 256 is configured to balance the forces of IOP on the pliable reservoir walls of the device preventing collapse after filling thereby preventing payload loss. The inner diameter of the distal end region 275 of the collection chamber 250 can be sized to provide for a uniform and controlled fill pattern that minimizes the risk of trapping air within the chamber 250 during exchange. The off-set configuration of the body 251 within which the collection chamber 250 is housed is streamlined and can wrap around the syringe barrel to minimize overall size for increased visibility of the treatment device during use. The body 251 of the exchange apparatus 200 tapers towards the needle tip (not shown) at an angle relative to the axis 202 of the cannula that improves visibility during use. The needle tip can be concentric or eccentric to the needle luer or the syringe barrel as described elsewhere herein.

Figure 25:
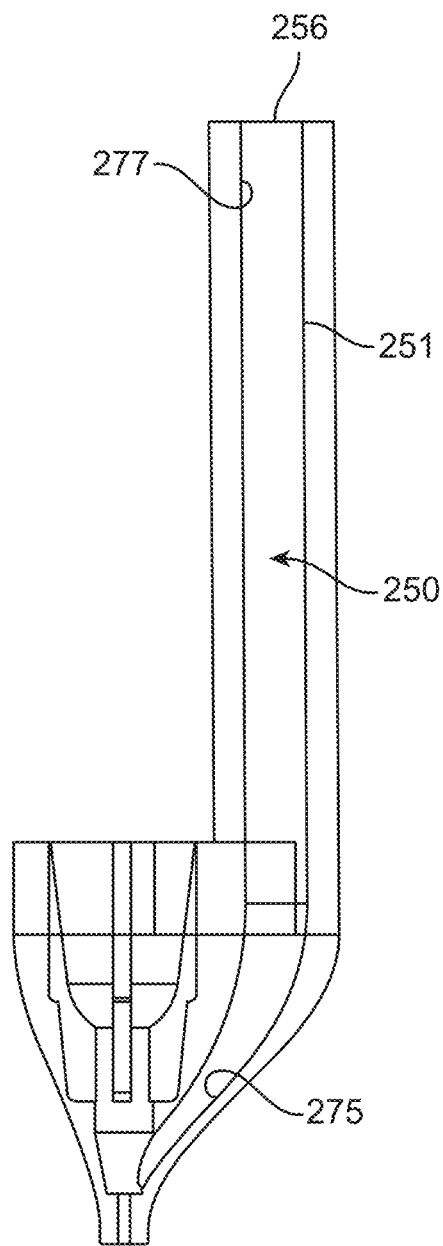
FIG. 25 illustrates an implementation of an exchange apparatus having an offset collection chamber designed for larger capacity.

Again with respect to FIGS. 24A-24D, the body 251 extends a first distance past a region where the needle hub assembly 500 couples with a syringe barrel 300. The body 251 of the collection chamber 250 can be arranged side-by-side with the syringe barrel 300. The size of the collection chamber body 251 can vary. FIG. 25 illustrates an implementation of an exchange apparatus 200 having an offset collection chamber 250 designed for larger capacity, for example a volume of about 200 ul, 300 ul or 400 ul. The overall configuration of the collection chamber 250 in which a distal end region 275 near the opening 258 into the collection chamber 250 is narrow and widens towards the proximal end region 277 directing fluid up to the porous structure 256 near an upper limit of the chamber 250. However, the larger capacity of the collection chamber 250 is provided for by extending a length of the body 251 within which the collection chamber 250 is housed. The longer collection chamber body 251 can align side-by-side with the syringe barrel 300. It should be appreciated that any of a variety of collection chamber volumes is considered herein, particularly for filling another type of implanted drug delivery device that is not limited by implantation within the vitreous.

The treatment devices described herein can be refilled after a period of time. The septum of the treatment device can be penetrated during refill with a refill needle, as described above, or for example such as that described in U.S. Pat. No. 9,033,911 or in U.S. Publication No. 2013/0165860, which are each incorporated by reference herein. The refill needle and the fill needle can be the same type of needle or can be distinct from one another. For example, the fill needle may or may not incorporate features to visualize filling whereas the refill needle does incorporate such features.

The fill needle and/or refill needle used in conjunction with the device implementations having elongated neck regions and/or redundant penetrable barriers as described in U.S. Provisional Application Ser. No. 62/318,582, filed Apr. 5, 2016, which is incorporated herein by reference thereto, may be longer than needles used in conjunction with device implementations having shorter neck regions. In some implementations, such as when redundant barrier systems are incorporated, the needle may include one or more reinforcement structures to accommodate the longer travel through the septum or a concentration of return holes near the distal end of the refill needle in order to refill the system efficiently. For example, to access the reservoir of a device having an elongated upper end region and incorporating, for example, a redundant septum or a penetrable element that does not reside within the proximal portion of the neck a needle may incorporate one or more features to provide for better penetration including, but not limited to a longer length, a reinforcement structure surrounding at least a region of its length, and/or concentration of return fluid holes near the distal end of the needle.

Once the expanded volume of the implanted reservoir is achieved, the device can be refilled at predictable intervals (e.g. every 3, 4, 5, 6 months or as along as every 12 months). However, changing the volume of the expanded device once implanted in the eye may not be desirable (e.g. movement in the eye once implanted may lead to potential trauma to surrounding structures or fluctuations in intraocular pressure) and is thus something to be avoided. The treatment devices described herein once implanted and expanded can maintain a consistent volume such that the outer diameter or contour of the reservoir does not change substantially throughout the use of the device and regardless of fill status. Further, the treatment devices described herein can maintain substantially the same expanded shape. For example, drug passively diffuses through the porous drug delivery element and out of the expanded reservoir over time. Despite this drug release into the eye, the expanded reservoir can remain filled with fluid, for example, fluid that enters the reservoir from the vitreous and drug formulation fluid remaining in the reservoir. The reservoir material can be formed of a substantially non-compliant material that tends to maintain its physical structure regardless of whether the interior of the reservoir is filled with drug. Further, refill of the treatment devices described herein can be performed such that a negative pressure and/or an excessive positive pressure do not build within it.

FIGS. 26A-26C show an implementation of an exchange apparatus 200 having an elongate structure 201 having a needle 270 extending through a removable sheath 280 and a collection chamber 250 that is removable from the exchange needle apparatus 200. As described elsewhere herein, the exchange needle apparatus 200 can include a locking connector 290 near a proximal end configured to couple to a syringe 300. Also as described elsewhere herein, the needle 270 and sheath 280 are configured to inject new material into the device 100 while simultaneously directing pre-existing material from the device 100 into the collection chamber 250 using positive pressure. The needle 270 of the elongate structure 201 can include an inner channel 219 coupled at its proximal end to the syringe 300 or other container holding the therapeutic fluid to be injected into the device. The channel 219 can extend to a distal opening 214 through which the therapeutic fluid can exit the lumen into the device 100. A sheath 280 having one or more openings 236 can surround at least a portion of the needle 270 creating a channel 239 along at least a portion of the outer surface of the needle 270 leading toward the collection chamber 250.

The collection chamber 250 can be defined by an impermeable wall 252 around at least a portion of the chamber 250. A first plug 430 formed of a penetrable barrier material such as an elastomeric septum can be positioned within a proximal opening to the chamber 250. A second plug 420 formed of a penetrable barrier material can be positioned at a distal end of the chamber 250 such that the chamber 250 is sealed on either end by the plugs 430, 420 (see FIG. 26C). At least the needle 270 of the elongate structure 201 can extend through the distal plug 420. The sheath 280 can extend from and be supported by a distal end of the wall 252 such that the sheath 280 remained attached to the wall 252 upon removal of the collection chamber 250 from the exchange apparatus 200. The plug 420 can be placed over the sheath 280 and the needle 270 extending through the sheath 280 prior to removal of the needle 270. The plug 420 can thereby inhibit leakage of the implantable device fluid 262 and sample fluid 264 from the distal opening of the chamber 250. A cap 435 can be positioned over the outer surface of plug 430 (FIG. 26C). The plug 430 and cap 435 can inhibit one or more of evaporation or leakage of the implantable device fluid 262 comprising sample fluid 264.

Figure 27A:
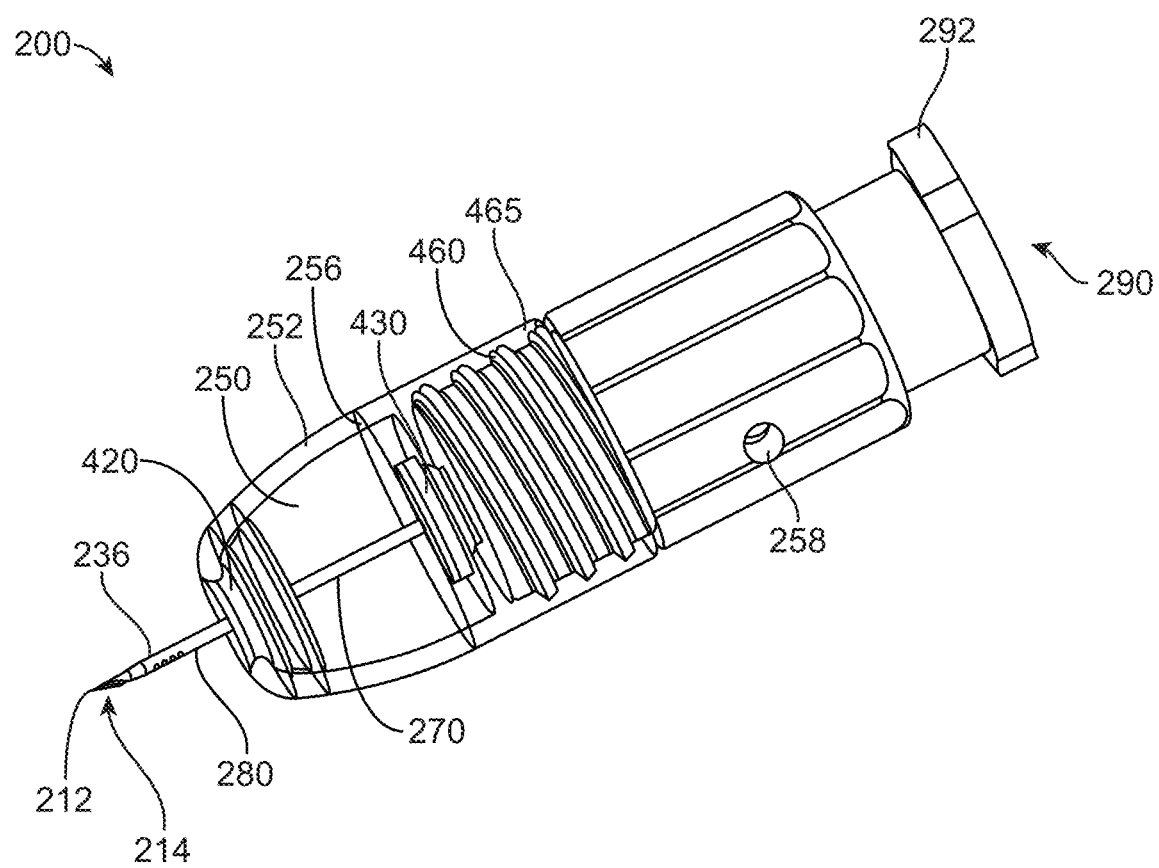
FIGS. 27A-27D are another implementation of an exchange apparatus having a removable collection chamber.
Figure 27B:
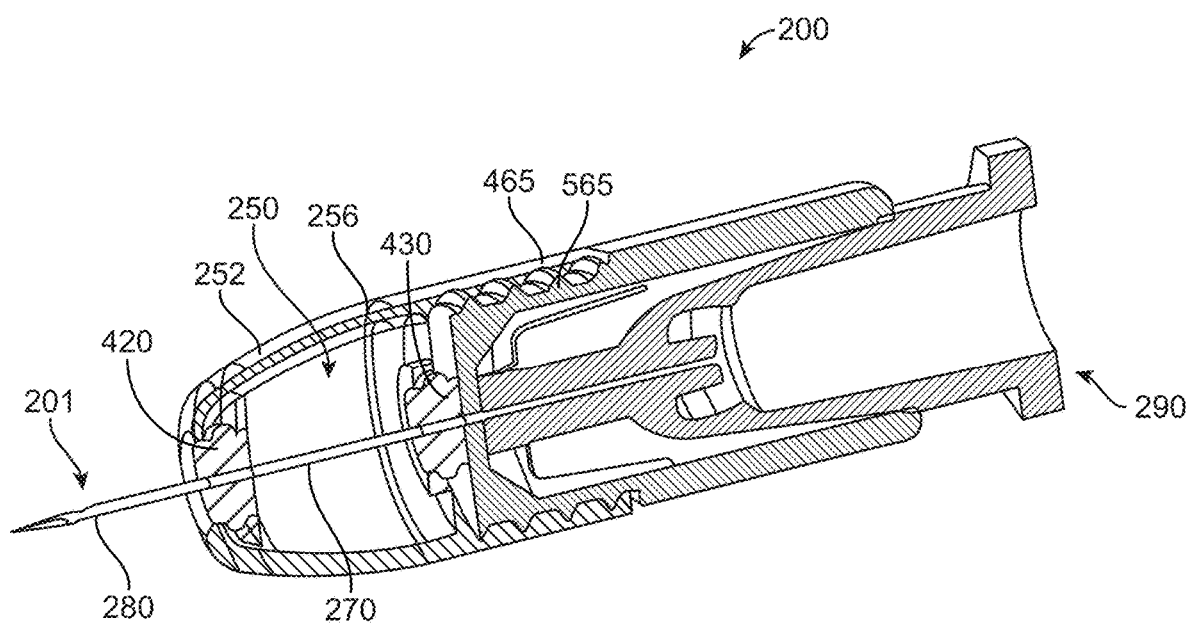
Figure 27C:
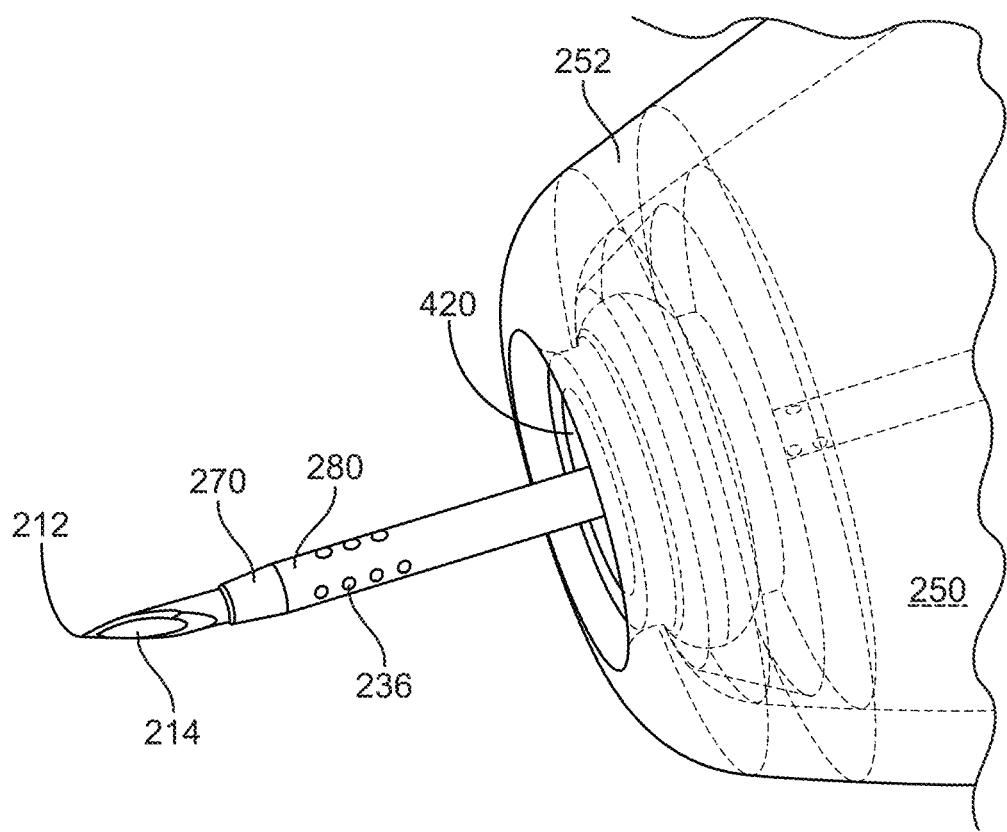

FIGS. 27A-27D illustrate another implementation of an exchange needle apparatus 200 having a collection chamber 250 that is removable from the exchange needle apparatus 200. The collection chamber 250 can be defined by an impermeable wall 252 around at least a portion of the chamber 250. A first plug 430 formed of a penetrable barrier material such as an elastomeric septum can be positioned at a proximal end of the chamber 250 and a second plug 420 can be positioned at a distal end of the chamber 250 such that the chamber 250 is sealed on either end by the plugs 430, 420. At least the needle 270 of the elongate structure 201 can extend through the first and second plugs 430, 420 (see FIG. 27B). As described elsewhere herein, a porous structure 256 can be positioned within the proximal end of the collection chamber 250 forming a proximal cap feature for restricting the venting of the exchange needle apparatus 200 during filling of the expandable reservoir 130. This porous structure 256 can be located distal to the proximal plug 430 such that at least the needle 270 of the elongate structure 201 additionally extends through the porous structure 256. FIG. 27C is a detail view showing the needle 270 of the elongate structure 201 extending through an outer sheath 280 and piercing the distal plug 420. Openings into 236 and from the outer sheath 280 allow the exchanged liquid to drain into the chamber 250.

Figure 27D:
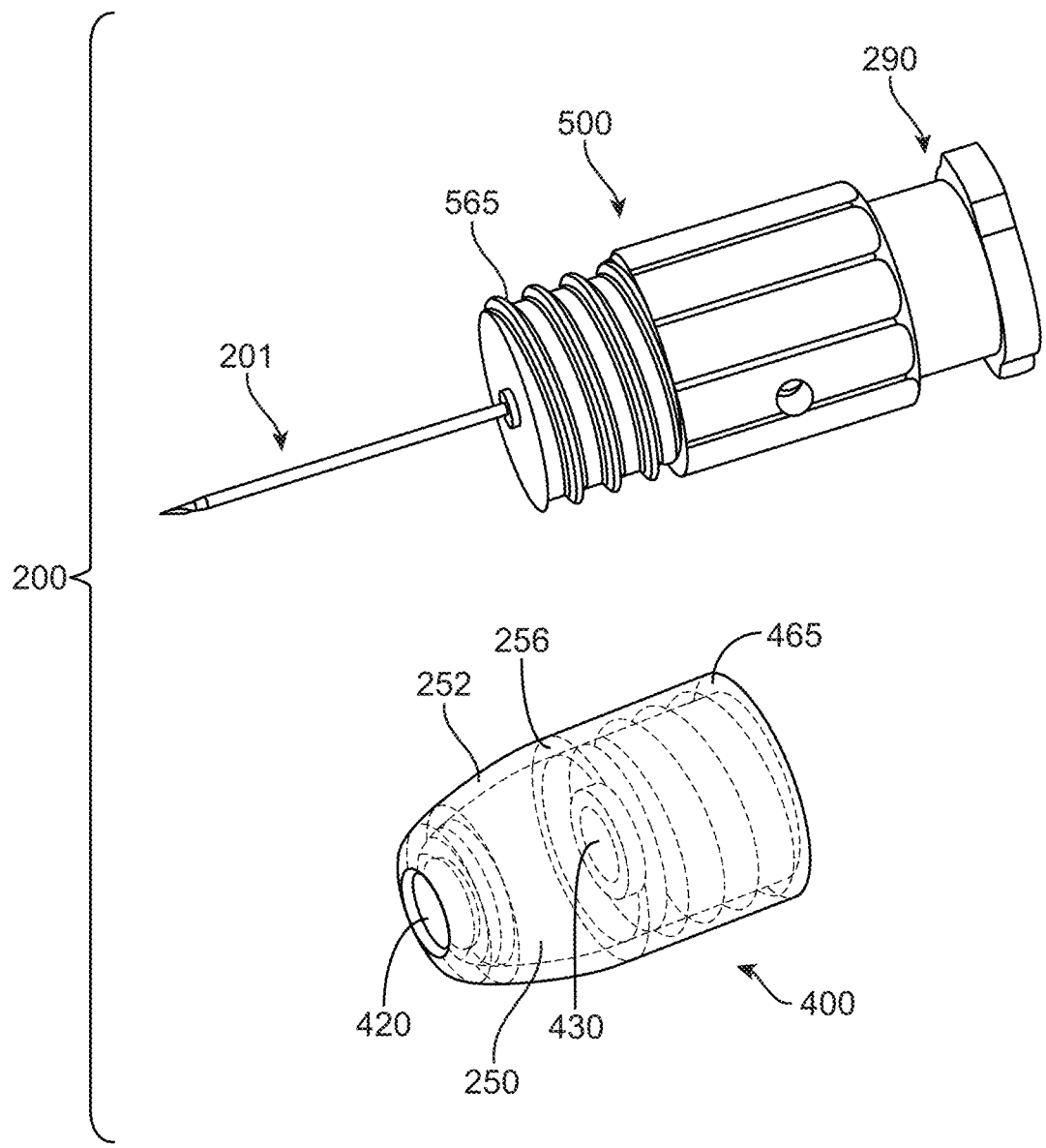

The collection chamber 250 can be removably coupled to the exchange apparatus 200 by any of a variety of mechanisms including annular snap-fit or threaded couplings. In some implementations, the collection chamber 250 can be removed from the exchange apparatus 200 by way of a threaded coupling. FIG. 27D is a view of the separated container 400 having the collection chamber 250 enclosed by two plugs 430, 420 leaving behind the needle hub assembly 500 including the elongate structure 201 and connector 290. Fluid can remain contained within the chamber 250 with both plugs 430, 420 resealed after withdrawal of the elongate structure 201. A distal end region 565 of the needle hub assembly 500 can be threaded and a proximal end region 465 of the sample container 400 can be correspondingly threaded such that the distal end region 565 and the proximal end region 465 couple together in threaded engagement. The thread of the needle hub assembly 500 can be on an outer surface of the distal end region 565 and the thread of the container 400 can be on an inner surface of the proximal end region 465 such that the proximal end region 465 receives the distal end region 565 of the needle hub assembly 500 therein.

The sample container 400 including the sealed collection chamber 250 upon separation from the remainder of the hub assembly 500 (as shown in FIG. 26B and FIG. 27D) can be transported, for example, to a lab facility or other location for further processing. One or both of the plugs 420, 430 can be penetrated in order to withdraw the sample fluid 264 within the chamber 250 such as by piercing the plugs 420, 430 with a needle to recover the fluid within a syringe. Alternatively or additionally, the sample container 400 can include a penetrable structure 259 within another area such as the wall 252 of the chamber 250 that can be penetrated by a needle-type device to draw a sample from the receiver chamber 250. The structure 259 can include one or more re-sealable materials suitable for penetration with a needle such as one or more of rubber or silicone elastomer. The structure 259 can also include one or more materials such as a fabric, a porous fabric, a semipermeable membrane, an air permeable material, a moisture vapor transfer waterproof fabric, a hydrophilic porous material, or a porous material or a porous sintered material. As described elsewhere herein, the wall 252 of the collection chamber 250 can be transparent or translucent such that a volume of material held within the collection chamber 250 is discernable to the user. The sample container 400 can have one or more shapes such as annular, spherical, cubic, ellipsoidal, or oval.

Indications

The treatment devices described herein can be used to treat and/or prevent a variety of other ocular conditions besides glaucoma, including but not limited to dry or wet age-related macular degeneration (AMD), neuroprotection of retinal ganglion cells, cataract or presbyopia prevention, cancers, angiogenesis, neovascularization, choroidal neovascularization (CNV) lesions, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma. Still further conditions that can be treated and/or prevented using the devices and methods described herein, include but are not limited to hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves' disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia.

Therapeutics

Examples of therapeutic agents that may be delivered by the treatment devices described herein and/or are described in the applications incorporated by reference herein are provided below and in Table 1 of U.S. application Ser. No. 14/937,784, published as U.S. 2016/0128867, which is incorporated herein in its entirety.

Therapeutics that can be delivered from the devices described herein include but are not limited to triamcinolone acetonide, bimatoprost or the free acid of bimatoprost, latanoprost or the free acid or salts of the free acid of latanoprost, ranibizumab, travoprost or the free acid or salts of the free acid of travoprost, timolol, levobunalol, brimonidine, dorzolamide, brinzolamide. Additional examples of therapeutic agents that may be delivered by the therapeutic device include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye in the manner described herein are also suitable for use in accordance with embodiments of the devices described herein.

The therapeutic agent can also include one or more of the following: abarelix, abatacept, abciximab, adalimumab, aldesleukin, alefacept, alemtuzumab, alpha-1-proteinase inhibitor, alteplase, anakinra, anistreplase, antihemophilic factor, antithymocyte globulin, aprotinin, arcitumomab, asparaginase, basiliximab, becaplermin, bevacizumab, bivalirudin, botulinum toxin type A, botulinum toxin type B, brolucizumab, capromab, cetrorelix, cetuximab, choriogonadotropin alfa, coagulation factor IX, coagulation factor VIIa, collagenase, corticotropin, cosyntropin, cyclosporine, daclizumab, darbepoetin alfa, defibrotide, denileukin diftitox, desmopressin, dornase alfa, drotrecogin alfa, eculizumab, efalizumab, enfuvirtide, epoetin alfa, eptifibatide, etanercept, exenatide, felypressin, filgrastim, follitropin beta, galsulfase, gemtuzumab ozogamicin, glatiramer acetate, glucagon recombinant, goserelin, human serum albumin, hyaluronidase, ibritumomab, idursulfase, immune globulin, infliximab, insulin glargine recombinant, insulin lyspro recombinant, insulin recombinant, insulin, porcine, interferon alfa-2a, recombinant interferon alfa-2b, recombinant interferon alfa con-1, interferon alfa-n1, interferon alfa-n3, interferon beta-1b, interferon gamma-1b, lepirudin, leuprolide, lutropin alfa, mecasermin, menotropins, muromonab, natalizumab, nesiritide, octreotide, omalizumab, oprelvekin, ospA lipoprotein, oxytocin, palifermin, palivizumab, panitumumab, pegademase bovine, pegaptanib, pegaspargase, pegfilgrastim, peginterferon alfa-2a, peginterferon alfa-2b, pegvisomant, pramlintide, ranibizumab, rasburicase, reteplase, rituximab, salmon calcitonin, sargramostim, secretin, sermorelin, serum albumin iodonated, somatropin recombinant, streptokinase, tenecteplase, teriparatide, thyrotropin alfa, tositumomab, trastuzumab, urofollitropin, urokinase, or vasopressin.

The therapeutic agent can include one or more of compounds that act by binding members of the immunophilin family of cellular proteins. Such compounds are known as "immunophilin binding compounds" Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories). The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent can include one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; proteosome inhibitors such as bortezomib, for injection; ranibuzumab and other antibodies directed to the same target; pegaptanib; vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; 13-cis retinoic acid; ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; verteporfin; snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent can include inhibitors of VEGF receptor kinase; inhibitors of VEGFA, VEGFC, VEGFD, bFGF, PDGF, Ang-1, Ang-2, PDGFR, cKIT, FGF, BDGF, mTOR, $\alpha v\beta 3$, $\alpha v\beta 5$, $\alpha 5\beta 1$ integrin, and alpha2 adrenergic receptor; inhibitors of complement factor B (e.g. TA106), complement factor D (CFD) (lampalizumab/TNX-234), C3 (e.g. APL-2, novel compstatin analogs), C5 (e.g. eculizumab, ARC1905, ALN-CC5), C5a (e.g. JPE-1375), and tubulin; AAV-CD56 The therapeutic agent can also include Complement Factor H (CFH), engineered mini-CFH, or recombinant CFH (rCFH).

The therapeutic agent can include a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as bortezomib, for injection; ranibizumab and other antibodies directed to the same target; pegaptanib; vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; 13-cis retinoic acid; ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; snET2 and other photo sensitizers with photodynamic therapy (PDT); and laser photocoagulation.

Prostaglandin analogues (PGAs) can be used to increase outflow of aqueous through the ciliary body and/or the trabecular meshwork including travaprost (0.004%), bimatoprost (0.03%, 0.01%), tafluprost (0.0015%), and latanoprost (0.005%). Beta blockers can be used to reduce aqueous fluid production by the ciliary body. Drugs in this class include timolol (0.5%). Carbonic anhydrase inhibitors can be used to reduce aqueous fluid production by the ciliary body as well. Drugs in this class include brinzolamide (1%), methazolamide, dorzolamide (2%), and acetazolamide. Alpha antagonists can be used to reduce aqueous fluid production by the ciliary body and increase outflow through the trabecular meshwork. Thus, the drug targets tissues located in both the anterior chamber and the posterior chamber and as such the devices can be implanted in either location to achieve a therapeutic result. Drugs in this class include brimonidine (0.1%, 0.15%) and apraclonidine (0.5%, 1.0%). Commercially available combinations of therapeutics considered herein include brimonidine tartrate/timolol maleate ophthalmic solution, and dorzolamide hydrochloride-timolol maleate ophthalmic solution. Further, other sustained release therapeutics considered herein include subconjunctival latanoprost, intracameral bimatoprost, and intravitreal brimonidine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials Materials Generally, the components of the devices described herein are fabricated of materials that are biocompatible and preferably insoluble in the body fluids and tissues that the device comes into contact with. The materials generally do not cause irritation to the portion of the eye that it contacts. Materials may include, by way of example, various polymers including, for example, silicone elastomers and rubbers, polyolefins, polyurethanes, acrylates, polycarbonates, polyamides, polyimides, polyesters, and polysulfones. One or more components of the devices described herein can be fabricated of a permeable material including, but not limited to, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers. One or more components of the devices described herein can be fabricated of a nonbiodegradable polymer, including but not limited to polymethylmethacrylate, a silicone elastomer, or silicone rubber. Other suitable non-erodible, biocompatible polymers which may be used in fabricating the devices described herein may include polyolefins such as polypropylene and polyethylene, homopolymers, and copolymers of vinyl acetate such as ethylene vinyl acetate copolymer, polyvinylchlorides, homopolymers and copolymers of acrylates such as polyethylmethacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, natural rubber, polyisobutylene, polymethylstyrene and other similar non-erodible biocompatible polymers.

One or more of the components of the devices described herein can be fabricated of a substantially non-compliant material that can be expanded to a particular shape. One or more of the components of the devices described herein can be fabricated of a rigid, non-pliable material. One or more of the components of the devices described herein can be fabricated of a shape memory material and/or superelastic material including, but not limited to shape memory alloys (SMA) like Nitinol (Ni—Ti alloy) and shape memory polymers (SMP) like AB-polymer networks based on oligo(e-caprolactone) dimethacrylates and n-butyl acrylate. Shape memory alloys generally have at least two phases: (1) a martensite phase, which has a relatively low tensile strength and which is stable at relatively low temperatures, and (2) an austenite phase, which has a relatively high tensile strength and which is stable at temperatures higher than the martensite phase. The shape memory characteristics are imparted on the material by heating the material to a temperature above the temperature at which the austenite phase is stable. While the material is heated to this temperature, the device is held in the "memory shape", which is shape that is desired to be "remembered".

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "front," "side," and "back" as well as "anterior," "posterior," "caudal," "cephalad" and the like or used to establish relative frames of reference, and are not intended to limit the use or orientation of any of the devices and/or systems to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for injecting a therapeutic agent into an ocular implant, the implant being at least partially implanted in an eye, the implant further providing at least a first resistance to outflow of therapeutic agent into the eye, the device comprising:
    an injection lumen configured to provide a pathway for injecting the therapeutic agent into the ocular implant;
    an outlet lumen configured to provide a pathway through which pre-existing fluid in the ocular implant exits the ocular implant; and
    a collection chamber fluidly coupled to the outlet lumen and operatively coupled to a first porous structure positioned within an annular element positioned near an upper end of the collection chamber forming a fixed upper limit of the collection chamber, the collection chamber configured to receive the pre-existing fluid that exits the ocular implant via the outlet lumen,
    wherein the first porous structure of the collection chamber provides a first fluid outflow resistance to gas outflow and a second fluid outflow resistance to liquid outflow, wherein the first fluid outflow resistance is lower than the first resistance to outflow of the implant, and the second fluid outflow resistance is greater than a force imparted onto the implant by intraocular pressure of the eye, and
    wherein injection of therapeutic agent into the ocular implant via the injection lumen causes the pre-existing fluid to exit the ocular implant and enter the collection chamber via the outlet lumen and causes a second pre-existing fluid to displace from the collection chamber.

2. The device of claim 1, wherein the implant is expandable once implanted in the eye from a first, collapsed configuration to a second, enlarged configuration.

3. The device of claim 1, wherein the implant comprises a second porous structure that provides the first resistance to outflow.

4. The device of claim 3, wherein the first fluid outflow resistance of the first porous structure of the collection chamber is less than the first resistance provided by the second porous structure of the implant, and the second fluid outflow resistance of the first porous structure of the collection chamber is greater than the first resistance of the implant.

5. The device of claim 1, wherein the second pre-existing fluid is a gas.

6. The device of claim 5, wherein the gas is air.

7. The device of claim 6, wherein the air is under vacuum.

8. The device of claim 1, wherein the second pre-existing fluid is displaced from the collection chamber via a vent.

9. The device of claim 1, wherein the second pre-existing fluid is displaced from the collection chamber via a valve.

10. The device of claim 3, wherein the implant is expandable once implanted in the eye from a first, collapsed configuration to a second, enlarged configuration, wherein the first porous structure of the collection chamber prevents collapse of the implant away from the second, enlarged configuration after filling.

11. The device of claim 3, wherein the first porous structure of the collection chamber is a hydrophobic membrane, a fabric, a porous fabric, a semipermeable membrane, an air permeable material, a moisture vapor transfer waterproof fabric, a hydrophilic porous material, or a porous sintered material.

12. The device of claim 3, wherein the collection chamber is concentric with a longitudinal axis of the injection lumen.

13. A device for injecting a therapeutic agent into an ocular implant, the implant being at least partially implanted in an eye, the implant further providing at least a first resistance to outflow of therapeutic agent into the eye, the device comprising:
    an injection lumen configured to provide a pathway for injecting the therapeutic agent into the ocular implant;
    an outlet lumen configured to provide a pathway through which pre-existing fluid in the ocular implant exits the ocular implant; and
    a collection chamber fluidly coupled to the outlet lumen and operatively coupled to a first porous structure, the collection chamber configured to receive the pre-existing fluid that exits the ocular implant via the outlet lumen,
    wherein the first porous structure of the collection chamber provides a first fluid outflow resistance to gas outflow and a second fluid outflow resistance to liquid outflow, wherein the first fluid outflow resistance is lower than the first resistance to outflow of the implant, and the second fluid outflow resistance is greater than a force imparted onto the implant by intraocular pressure of the eye, and
    wherein injection of therapeutic agent into the ocular implant via the injection lumen causes the pre-existing fluid to exit the ocular implant and enter the collection chamber via the outlet lumen and causes a second pre-existing fluid to displace from the collection chamber, wherein the collection chamber is a coiled tubular structure providing a uniform fill pattern that minimizes trapping of the second pre-existing fluid displaced from the collection chamber.

14. The device of claim 13, wherein the collection chamber is offset relative to a longitudinal axis of the injection lumen.

15. The device of claim 14, wherein the coiled tubular structure extends between an opening into the tubular collection chamber and terminates at the first porous structure.

16. The device of claim 15, wherein the coiled tubular structure has a uniform inner diameter over a length of the coiled tubular structure.

17. The device of claim 15, where the coiled tubular structure has an inner diameter that enlarges proximally to a second inner diameter.

* * * * *